US012624015B2

(12) United States Patent
Salem et al.

(10) Patent No.: US 12,624,015 B2
(45) Date of Patent: May 12, 2026

(54) JNK INHIBITORS AS ANTICANCER AGENTS

(71) Applicant: University of Iowa Research Foundation, Iowa City, IA (US)

(72) Inventors: Aliasger K. Salem, Coralville, IA (US); Somaya Ali Mohammed Elsaid Abdelrahman, Redwood City, CA (US)

(73) Assignee: University of Iowa Research Foundation, Iowa City, IA (US)

( * ) Notice: Subject to any disclaimer, the term of this patent is extended or adjusted under 35 U.S.C. 154(b) by 1027 days.

(21) Appl. No.: 17/622,210

(22) PCT Filed: Jun. 24, 2020

(86) PCT No.: PCT/US2020/039373
§ 371 (c)(1),
(2) Date: Dec. 22, 2021

(87) PCT Pub. No.: WO2020/263989
PCT Pub. Date: Dec. 30, 2020

(65) Prior Publication Data

US 2022/0411398 A1 Dec. 29, 2022

Related U.S. Application Data

(60) Provisional application No. 62/865,659, filed on Jun. 24, 2019.

(51) Int. Cl.

| | |
|---|---|
| ***C07D 333/66*** | (2006.01) |
| ***A61K 9/00*** | (2006.01) |
| ***A61K 9/16*** | (2006.01) |
| ***A61K 9/51*** | (2006.01) |
| ***A61K 31/38*** | (2006.01) |
| ***A61P 35/00*** | (2006.01) |

(52) U.S. Cl.
CPC .......... *C07D 333/66* (2013.01); *A61K 9/0019* (2013.01); *A61K 9/1641* (2013.01); *A61K 9/5161* (2013.01); *A61K 31/38* (2013.01); *A61P 35/00* (2018.01)

(58) Field of Classification Search
CPC .............................. A61K 31/38; C07D 333/80
See application file for complete search history.

(56) References Cited

U.S. PATENT DOCUMENTS

| | | | | |
|---|---|---|---|---|
| 5,434,146 | A | 7/1995 | Labrie et al. | |
| 5,795,582 | A | 8/1998 | Wright | |
| 5,985,601 | A | 11/1999 | Ni et al. | |
| 6,995,284 | B2 | 2/2006 | Dalton et al. | |
| 7,759,520 | B2 | 7/2010 | Dalton et al. | |
| 8,759,402 | B2 | 6/2014 | Gottlieb et al. | |
| 8,853,266 | B2 | 10/2014 | Dalton et al. | |
| 8,962,666 | B2 | 2/2015 | Emans et al. | |
| 9,572,894 | B2 | 2/2017 | Salem et al. | |
| 10,273,476 | B2 | 4/2019 | Hong et al. | |
| 10,314,941 | B2 | 6/2019 | Mckinley et al. | |
| 10,335,498 | B2 | 7/2019 | Elangovan et al. | |
| 10,548,959 | B2 | 2/2020 | Khan et al. | |
| 10,669,543 | B2 | 6/2020 | Hong et al. | |
| 2003/0004564 | A1 | 1/2003 | Elkins et al. | |
| 2004/0143017 | A1 | 7/2004 | Manning et al. | |
| 2004/0224030 | A1 | 11/2004 | Shastri et al. | |
| 2005/0288282 | A1 * | 12/2005 | Delorme .............. | C07D 277/82 548/545 |
| 2007/0154529 | A1 | 7/2007 | Bullerdiek | |
| 2007/0292478 | A1 | 12/2007 | Youri | |
| 2010/0105762 | A1 | 4/2010 | Morishita et al. | |
| 2011/0112654 | A1 | 5/2011 | Faldt | |
| 2011/0143397 | A1 | 6/2011 | Kariko et al. | |
| 2012/0190651 | A1 | 7/2012 | Pari et al. | |
| 2012/0195936 | A1 | 8/2012 | Rudolph et al. | |
| 2013/0123314 | A1 | 5/2013 | Emans et al. | |
| 2013/0243876 | A1 | 9/2013 | Mcdonald et al. | |
| 2013/0259923 | A1 | 10/2013 | Bancel et al. | |
| 2014/0066388 | A1 | 3/2014 | Anderson et al. | |
| 2015/0071904 | A1 | 3/2015 | Collins et al. | |
| 2015/0125517 | A1 | 5/2015 | Mcdonald et al. | |
| 2016/0045439 | A1 * | 2/2016 | Criscione ............. | A61K 9/0019 525/450 |
| 2016/0220698 | A1 | 8/2016 | Elangovan et al. | |
| 2017/0189552 | A1 | 7/2017 | Hasenpusch et al. | |
| 2017/0215409 | A1 | 8/2017 | Chen et al. | |
| 2017/0314020 | A1 | 11/2017 | Hong et al. | |
| 2018/0000736 | A1 | 1/2018 | Martin et al. | |
| 2018/0169298 | A1 | 6/2018 | Mckinley et al. | |
| 2019/0055224 | A1 | 2/2019 | Jetti et al. | |

(Continued)

FOREIGN PATENT DOCUMENTS

| | | | |
|---|---|---|---|
| AU | 2021259858 | B2 | 4/2025 |
| CA | 2618404 | A1 | 2/2007 |

(Continued)

OTHER PUBLICATIONS

Angell "N-(3-Cyano-4,5,6,7-tetrahydro-1-benzothien-2-yl)amides as potent, selective, inhibitors of JNK2 and JNK3" BMCL 2007 17 2007 1296-1301 (Year: 2007).*
Saraiah "One-Pot Synthesis of 2-(Aryl/Alkyl)amino-3-cyanobenzo[b]-thiophenes and Their Hetero-Fused Analogues by Pd-Catalyzed Intramolecular Oxidative C—H Functionalization/Arylthiolation" Eur. J. Org. Chem. 2017, 5679-5688 (Year: 2017).*
Bains, et al. "Encapsulation of the p38 MAPK inhibitor GSK 678361A in nanoparticles for inflammatorybased disease states" J. Interdiscip. Nanomed. Jan. 3, 2016 83-123 (Year: 2016).*
Romiszewski, et al. "Optical properties of thiophene-containing liquid crystalline and hybrid liquid crystalline materials" New J. Chem., 2014,38, 2927 (Year: 2014).*

(Continued)

*Primary Examiner* — Svetlana M Ivanova
(74) *Attorney, Agent, or Firm* — Schwegman Lundberg & Woessner, P.A.

(57) ABSTRACT

Compounds that inhibit JNK, e.g., JNK2 and/or JNK3, such as fused thiophenes, and methods of making and using the compounds are provided.

6 Claims, 65 Drawing Sheets

(56) References Cited

U.S. PATENT DOCUMENTS

| | | | |
|---|---|---|---|
| 2019/0144856 | A1 | 5/2019 | Hong et al. |
| 2020/0078491 | A1 | 3/2020 | Mckinley et al. |
| 2020/0138742 | A1 | 5/2020 | Qin et al. |
| 2020/0222559 | A1 | 7/2020 | Elangovan et al. |
| 2020/0237925 | A1 | 7/2020 | Wei et al. |
| 2020/0289482 | A1 | 9/2020 | Cebotaru |
| 2021/0085827 | A1 | 3/2021 | Mckinley et al. |
| 2021/0308326 | A1 | 10/2021 | Salem et al. |
| 2021/0361578 | A1 | 11/2021 | Salem et al. |
| 2021/0379172 | A1 | 12/2021 | Salem et al. |
| 2022/0241214 | A1 | 8/2022 | Salem et al. |
| 2022/0249399 | A1 | 8/2022 | Salem et al. |
| 2022/0265700 | A1 | 8/2022 | Seol et al. |
| 2023/0001017 | A1 | 1/2023 | Salem et al. |
| 2023/0293678 | A1 | 9/2023 | Salem et al. |
| 2023/0312639 | A1 | 10/2023 | Salem et al. |
| 2024/0100183 | A1 | 3/2024 | Salem et al. |
| 2024/0293322 | A1 | 9/2024 | Sluka et al. |
| 2024/0398710 | A1 | 12/2024 | Salem et al. |
| 2025/0073322 | A1 | 3/2025 | Salem et al. |

FOREIGN PATENT DOCUMENTS

| | | | | |
|---|---|---|---|---|
| CN | 101385851 | A | 3/2009 | |
| CN | 101505787 | A | 8/2009 | |
| CN | 101959529 | A | 1/2011 | |
| CN | 103405787 | A | 11/2013 | |
| CN | 104736569 | A | 6/2015 | |
| CN | 104800164 | A | 7/2015 | |
| CN | 107041875 | A | 8/2017 | |
| CN | 107405388 | A | 11/2017 | |
| CN | 108136070 | A | 6/2018 | |
| CN | 114010640 | A | 2/2022 | |
| CN | 115835886 | A | 3/2023 | |
| EP | 1000541 | A1 | 5/2000 | |
| EP | 1496037 | A | 1/2005 | |
| EP | 2308473 | A1 | 4/2011 | |
| EP | 3170391 | A1 | 5/2017 | |
| IN | 202217067017 | | 8/2023 | |
| JP | 2010029211 | A | 2/2010 | |
| JP | 2011520440 | A | 7/2011 | |
| JP | 2012021005 | A | 2/2012 | |
| JP | 2015508414 | A | 3/2015 | |
| JP | 2017513862 | A | 6/2017 | |
| JP | 2019537599 | | 12/2019 | |
| JP | 2023523931 | A | 6/2023 | |
| JP | 7600264 | B2 | 12/2024 | |
| JP | 2025026505 | A | 2/2025 | |
| NZ | 216159 | A * | 9/1988 | ........... C07D 333/38 |
| WO | WO-9728809 | A1 | 8/1997 | |
| WO | WO-1999058656 | | 11/1999 | |
| WO | WO-02083667 | A2 | 10/2002 | |
| WO | WO-03077919 | A1 | 9/2003 | |
| WO | WO-2005000236 | A2 | 1/2005 | |
| WO | WO-2005058032 | A1 | 6/2005 | |
| WO | WO-2006047279 | A2 | 5/2006 | |
| WO | WO-2007027582 | A2 | 3/2007 | |
| WO | WO-2008124922 | A1 | 10/2008 | |
| WO | WO-2009082437 | A2 | 7/2009 | |
| WO | WO-2009097545 | A1 | 8/2009 | |
| WO | WO-2009109908 | A1 | 9/2009 | |
| WO | WO-2010048418 | A1 | 4/2010 | |
| WO | WO-2010061005 | A1 | 6/2010 | |
| WO | WO-2012020308 | A2 | 2/2012 | |
| WO | WO-2012175357 | A1 | 12/2012 | |
| WO | WO-2013106643 | A2 | 7/2013 | |
| WO | WO-2013171736 | A1 | 11/2013 | |
| WO | WO-2014052640 | A1 | 4/2014 | |
| WO | WO-2014071122 | A1 | 5/2014 | |
| WO | 2014115022 | | 7/2014 | |
| WO | WO-2014134179 | A1 | 9/2014 | |
| WO | WO-2014152940 | A1 | 9/2014 | |
| WO | WO-2015020769 | A2 | 2/2015 | |
| WO | WO-2016061615 | A1 | 4/2016 | |
| WO | WO-2016075154 | A1 | 5/2016 | |
| WO | WO-2016077215 | A2 | 5/2016 | |
| WO | WO-2016086136 | A1 | 6/2016 | |
| WO | WO-2016112176 | A1 | 7/2016 | |
| WO | WO-2016115516 | A1 | 7/2016 | |
| WO | WO-2016115516 | A8 | 7/2016 | |
| WO | WO-2017031214 | A1 | 2/2017 | |
| WO | WO-2017117430 | A1 * | 7/2017 | ........... A61K 31/136 |
| WO | WO-2018031771 | A1 | 2/2018 | |
| WO | WO-2018067545 | A1 | 4/2018 | |
| WO | WO-2018146599 | A1 | 8/2018 | |
| WO | 2019014429 | | 1/2019 | |
| WO | WO-2019010092 | A1 | 1/2019 | |
| WO | WO-2019140003 | A1 | 7/2019 | |
| WO | WO-2019209883 | A1 | 10/2019 | |
| WO | WO-2019222277 | A1 | 11/2019 | |
| WO | WO-2020018818 | A1 | 1/2020 | |
| WO | WO-2020180985 | A1 | 9/2020 | |
| WO | WO-2020203961 | A1 | 10/2020 | |
| WO | WO-2020257658 | A1 | 12/2020 | |
| WO | WO-2020263989 | A1 | 12/2020 | |
| WO | WO-2021086973 | A2 | 5/2021 | |
| WO | WO-2021086973 | A9 | 5/2021 | |
| WO | WO-2021086973 | A3 | 9/2021 | |
| WO | WO-2021217036 | A1 | 10/2021 | |
| WO | WO-2022040564 | A1 | 2/2022 | |
| WO | WO-2022040564 | A9 | 2/2022 | |
| WO | WO-2022125963 | A1 | 6/2022 | |
| WO | WO-2022125963 | A9 | 6/2022 | |
| WO | WO-2022246280 | A1 | 11/2022 | |
| WO | WO-2022271951 | A1 | 12/2022 | |
| WO | WO-2023130022 | A2 | 7/2023 | |
| WO | WO-2023130022 | A3 | 8/2023 | |

OTHER PUBLICATIONS (ÂOne-Pot Synthesis of 2-(Aryl/Alkyl)amino-3-cyanobenzo[b]-thiophenes and Their Hetero-Fused Analogues by Pd-Catalyzed Intramolecular Oxidative CâH Functionalization/Arylthiolationâ Eur. J. Org. Chem. 2017, 5679â5688 (Year: 2017).*

"U.S. Appl. No. 16/426,374, Final Office Action mailed Mar. 26, 2024", 21 pgs.

"U.S. Appl. No. 17/260,754, Non Final Office Action mailed May 22, 2024", 20 pgs.

"U.S. Appl. No. 17/260,754, Response filed Apr. 2, 2024 to Restriction Requirement mailed Feb. 2, 2024", 5 pgs.

"U.S. Appl. No. 17/580,129, Final Office Action mailed Jun. 21, 2024", 24 pgs.

"U.S. Appl. No. 17/580,129, Response filed Apr. 29, 2024 to Non Final Office Action mailed Oct. 27, 2023", 7 pgs.

"Australian Application Serial No. 2021259858, Response filed May 7, 2024 to First Examination Report mailed Jan. 8, 2024", 12 pgs.

"Australian Application Serial No. 2021259858, Second Examiners Report mailed May 17, 2024", 4 pgs.

"Israel Application Serial No. 297486, Response filed Mar. 25, 2024 to Office Action mailed May 28, 2023", with English claims, 17 pgs.

"Japanese Application Serial No. 2022-564329, Notification of Reasons for Refusal mailed Jan. 30, 2024", with machine translation, 10 pgs.

An, et al., "Vitamin D improves the content of TGF-P and IGF-1 in intervertebral disc of diabetic rats", Experimental Biology and Medicine 242.12, (May 24, 2017), 1254-1261.

Fonseca-Santos, et al., "An overview of carboxymethyl derivatives of chitosan: Their use as biomaterials and drug delivery systems", Materials Science and Engineering: C 77, (2017), 1349-1362.

Murai, M, et al., "Current topics on inhibitors of respiratory complex I", Biochimica et Biophysica Acta (BBA)—Bioenergetics, 1857(7), [Online] Retrieved from the internet: <https://doi.Org/10.1016/j.bbabio.2015.11.009>, (2016), 884-891.

Rustenburg, Christine M E, et al., "Osteoarthritis and intervertebral disc degeneration: Quite different, quite similar", JOR Spine, 1(4), e1033, [Online] Retrieved from the internet: <https://doi.org/10.1002/jsp2.1033>, (2018), 10 pgs.

(56) References Cited

OTHER PUBLICATIONS

Shahani, Komal, et al., "Highly Loaded, Sustained-Release Microparticles of Curcumin for Chemoprevention", J Pharm Sci., 100(7), (2011), 2599-2609.
Zhang, et al., "The development of collagen based composite scaffolds for bone regeneration", Bioactive materials 3.1, (2018), 129-138.
"Australian Application Serial No. 2020233397, Response filed Oct. 6, 2023 to First Examination Report mailed Oct. 21, 2022", 20 pgs.
"U.S. Appl. No. 16/426,374, Response filed Dec. 22, 2023 to Non Final Office Action mailed Jun. 23, 2023", 9 pgs.
"U.S. Appl. No. 17/119,384, Corrected Notice of Allowability mailed Jan. 17, 2024", 5 pgs.
"U.S. Appl. No. 17/119,384, Corrected Notice of Allowability mailed Oct. 23, 2023", 2 pgs.
"U.S. Appl. No. 17/221,532, Examiner Interview Summary mailed Dec. 6, 2023", 2 pgs.
"U.S. Appl. No. 17/221,532, Non Final Office Action mailed Oct. 24, 2023", 15 pgs.
"U.S. Appl. No. 17/260,754, Restriction Requirement mailed Feb. 2, 2024", 8 pgs.
"U.S. Appl. No. 17/580,129, Non Final Office Action mailed Oct. 27, 2023", 21 pgs.
"Australian Application Serial No. 2020233397, Response Filed Oct. 18, 2023 to Subsequent Examiners Report mailed Oct. 11, 2023", 15 pgs.
"Australian Application Serial No. 2020233397, Subsequent Examiners Report mailed Oct. 11, 2023", 3 pgs.
"Australian Application Serial No. 2021259858, First Examination Report mailed Jan. 8, 2024", 4 pgs.
"Canadian Application Serial No. 3,132,533, Office Action mailed Oct. 11, 2023", 3 pgs.
"International Application Serial No. PCT/US2022/030375, International Preliminary Report on Patentability mailed Nov. 30, 2023", 11 pgs.
"International Application Serial No. PCT/US2022/034726, International Preliminary Report on Patentability mailed Jan. 4, 2024", 9 pgs.
Kohane, Daniel, "Microparticles and Nanoparticles for Drug Delivery", Biotechnology and Bioengineering, vol. 96, No. 2, (Feb. 1, 2007), 203-209.
Netisingha, H., "Intervertebral Disc Disease in Dogs", University of Illinois College of Veterinary Medicine, vetmed.illinois.edu/pet-health-columns/intervertebral-disc-disease- dogs, (May 6, 2019), 1-5.
Omlor, G., et al., "Injection of a polymerized hyaluronic acid/collagen hydrogel matrix in an in vivo porcine disc degeneration model", European Spine Journal, 21(9), (2012), 1700-1708.
Son, So-Ra, et al., "Platelet-rich plasma encapsulation in hyaluronic acid/gelatin-BCP hydrogel for growth factor delivery in BCP sponge scaffold for bone regeneration", Journal of Biomaterials Applications 29, (2015), 988-1002.
Yang, J. J, et al., "Intervertebral disc needle puncture injury can be repaired using a gelatin- poly (y-glutamic acid) hydrogel: an in vitro bovine biomechanical validation", European Spine Journal, 27(10), (2018), 2631-2638.
"U.S. Appl. No. 16/426,374, Non Final Office Action mailed Jun. 23, 2023", 20 pgs.
"U.S. Appl. No. 17/119,384, Response filed Jun. 21, 2023 to Non Final Office Action mailed Dec. 21, 2022", 13 pgs.
"U.S. Appl. No. 17/221,532, Final Office Action mailed Jun. 22, 2023", 12 pgs.
"U.S. Appl. No. 18/256,593, Preliminary Amendment filed Jun. 2023", 7 pgs.
"Canadian Application Serial No. 3, 132,533, Response Filed May 2023 to Examiners Rule 86(2) Report mailed Jan. 2023", 12 pgs.
"Chinese Application Serial No. 202180044990.7, Voluntary Amendment Filed Jul. 7, 2023", w/ English Claims, 7 pgs.
"European Application Serial No. 20716045.8, Indication of deficiencies in a request under Rule 22 EPC mailed May 16, 2023", 2 pgs.
"European Application Serial No. 20716045.8, Response Filed May 4, 2023 to Indication of deficiencies in a request under Rule 22 EPC mailed Mar. 22, 2023", No Claim Amendments, 5 pgs.
"European Application Serial No. 20716045.8, Response Filed May 31, 2023 to Indication of deficiencies in a request under Rule 22 EPC mailed May 16, 2023", No Amendments to Claims, 3 pgs.
"European Application Serial No. 21724985.3, Response filed May 10, 2023 to Communication Pursuant to Rules 161(1) and 162 EPC mailed Nov. 2023", 8 pgs.
"International Application Serial No. PCT/US2021/062913, International Preliminary Report on Patentability mailed Jun. 22, 2023", 12 pgs.
"International Application Serial No. PCT/US2022/082553, International Search Report mailed Jul. 3, 2023", 8 pgs.
"International Application Serial No. PCT/US2022/082553, Invitation to Pay Additional Fees mailed May 10, 2023", 6 pgs.
"International Application Serial No. PCT/US2022/082553, Written Opinion mailed Jul. 3, 2023", 20 pgs.
"Israel Application Serial No. 297486, Office Action mailed May 28, 2023", w/ English translation, 9 pgs.
Badieyan, Zohreh Sadat, "Concise Review: Application of Chemically Modified mRNA in Cell Fate Conversion and Tissue Engineering", Stem Cells Translational Medicine, 8(8), (Mar. 19, 2019), 833-843.
Briggs, Jon J, et al., "Cystatin E/M suppresses legumain activity and invasion of human melanoma", Bmc Cancer, Biomed Central, London, GB, vol. 10, No. 1, (Jan. 15, 2010), 1-13.
Chen, Jianting, et al., "In vitro evaluation of drug delivery behavior for inhalable amorphous nanoparticle formulations in a human lung epithelial cell model", International Journal of Pharmaceutics 596, 120211, (Jan. 21, 2021), 1-9.
Cho, Do-Yeon, et al., "In-vitro evaluation of a ciprofloxacin- and ivaca or-coated sinus stent against Pseudomonas aeruginosa biofilms", International Forum of Allergy & Rhinology, vol. 9, No. 5, (May 2019), 486-492.
Dalton, James T, et al., "The selective androgen receptor modulator GTx-024 (enobosarm) improves lean body mass and physical function in healthy elderly men and postmenopausal women: results of a double-blind, placebo-controlled phase II trial", J Cachexia Sarcopenia Muscle, 2, (2011), 153-161.
Ellis, B. L, "A survey of ex vivo/in vitro transduction efficiency of mammalian primary cells and cell lines with Nine natural adeno-associated virus (AAV1-9) and one engineered adeno-associated virus serotype", Virology Journal, 10 (74), [Online]. Retrieved from the Internet: <URL: https://doi.Org/10.1186/1>, (2013), 1-10.
Han, Felicity, et al., "Bioerodable PLGA-based microparticles for producing sustained-release drug formulations and strategies for improving drug loading", Front Pharmacol., vol. 7, Article 185, (Jun. 2016), 1-11.
Lagreca, Elena, et al., "Recent advances in the formulation of PLGA microparticles for controlled drug delivery", Progress in Biomaterials, 9, (2020), 153-174.
Lee, H. J, et al., "Targeted delivery of microRNA-145 to metastatic breast cancer by peptide conjugated branched PEI gene carrier", Macromol. Res. 21, [Online]. Retrieved from the Internet: <URL: https://doi.org/10.1007/s13233-013-1161-z>, (2013), 1201-1209.
Lopes-Pacheco, Miquéias, "CFTR Modulators: The Changing Face of Cystic Fibrosis in the Era of Precision Medicine", Frontiers in Pharmacology, vol. 10, Article 1662, (Feb. 2020), 1-29.
Mohler, Michael, et al., "Nonsteroidal Selective Androgen Receptor Modulators (SARMs): Dissociating the Anabolic and Androgenic Activities of the Androgen Receptor for Therapeutic Benefit", J Med Chem., 52(12), (2009), 3597-3617.
Park, Kinam, et al., "Formulation composition, manufacturing process, and characterization of poly(lactide-co-glycolide) microparticles (abstract)", J Control Release, vol. 329, pp. 1150-1161, (2021), 2 pgs.
Park, Kinam, et al., "Injectable, long-acting PLGA formulations: Analyzing PLGA and understanding microparticle formation", Journal of Controlled Release, 304, (2019), 125-134.

(56) References Cited

OTHER PUBLICATIONS

Porsio, Barbara, et al., "Inhalable nano into micro dry powders for ivacaftor delivery: The role of mannitol and cysteamine as mucus-active agents", International Journal of Pharmaceutics 582, 119304, (Apr. 6, 2020), 1-12.
Porsio, Barbara, et al., "Mucus and Cell-Penetrating Nanoparticles Embedded in Nano- into- Micro Formulations for Pulmonary Delivery of Ivacaftor in Patients with Cystic Fibrosis", ACS Appl. Mater. Interfaces, 10, (2018), 165-181.
Sluka, Kathleen, "Unilateral intramuscular injections of acidic saline produce a bilateral, long-lasting hyperalgesia", Muscle & Nerve, 24, (2001), 37-46.
Solomon, Z J, et al., "Selective Androgen Receptor Modulators: Current Knowledge and Clinical Applications", Sex Med Rev, 7(1), pp. 84-94, (2019), 18 pgs.
Song, J., "The candidate tumor suppressor CST6 alters the gene expression profile of human breast carcinoma cells: Down-regulation of the potent mitogenic, motogenic, and angiogenic factor autotaxin", Biochemical and Biophysical Research Communications, Elsevier, Amsterdam NL, vol. 340, No. 1, XP024924027, (Feb. 3, 2006), 175-182.
Taylor, Jessica D, "Zein: Novel Natural Polymer for Nanoparticle- and Film-Mediated Gene Delivery (thesis)", Biological Systems Engineering-Dissertations, Theses, and Student Research. 36., [Online]. Retrieved from the Internet: <URL: https://digitalcommons.unl.edu/biosysengdiss/36>, (2013), 130 pgs.
White, Hillary, et al., "A novel use for testosterone to treat central sensitization of chronic pain in fibromyalgia patients", International Immunopharmacology, vol. 27, Issue 2, [Online]. Retrieved from the Internet: <URL: http://accurateclinic.com/wp-content/uploads/2016/02/A-novel-use-for-testosterone-to-treat-central-sensitization-of-chronic-pain-in-fibromyalgia-patients-2015.pdf>, (2015), 244-248.
White, Hillary, et al., "Treatment of pain in fibromyalgia patients with testosterone gel: Pharmacokinetics and clinical response", International Immunopharmacology, vol. 27, Issue 2, (2015), 249-256.
Zhu, Chune, et al., "Inhalable Nanocomposite Microparticles with Enhanced Dissolution and Superior Aerosol Performance", Mol. Pharmaceutics, 17, (2020), 3270-3280.
U.S. Appl. No. 18/644,608, filed Apr. 24, 2024, MEK1/2Z Inhibitor-Loaded Microparticle Formulation.
U.S. Appl. No. 18/572,054, filed Dec. 19, 2023, Sustained Release Formulations Comprising a Selective Androgen Receptor Modulator.
"U.S. Appl. No. 14/983,021, Advisory Action mailed Sep. 18, 2017", 3 pgs.
"U.S. Appl. No. 14/983,021, Advisory Action mailed Nov. 7, 2018", 3 pgs.
"U.S. Appl. No. 14/983,021, Final Office Action mailed Jun. 2, 2017", 15 pgs.
"U.S. Appl. No. 14/983,021, Final Office Action mailed Jun. 14, 2018", 13 pgs.
"U.S. Appl. No. 14/983,021, Non Final Office Action mailed Feb. 8, 2017", 14 pgs.
"U.S. Appl. No. 14/983,021, Non Final Office Action mailed Nov. 3, 2017", 13 pgs.
"U.S. Appl. No. 14/983,021, Notice of Allowance mailed Feb. 25, 2019", 9 pgs.
"U.S. Appl. No. 14/983,021, Response filed Apr. 3, 2018 to Non Final Office Action mailed Nov. 3, 2017", 11 pgs.
"U.S. Appl. No. 14/983,021, Response filed May 4, 2017 to Non Final Office Action mailed Feb. 8, 2017", 10 pgs.
"U.S. Appl. No. 14/983,021, Response filed Sep. 5, 2017 to Final Office Action mailed Jun. 2, 2017", 7 pgs.
"U.S. Appl. No. 14/983,021, Response filed Oct. 15, 2018 to Final Office Action mailed Jun. 14, 2018", 7 pgs.
"U.S. Appl. No. 14/983,021, Response filed Nov. 15, 2016 to Restriction Requirement mailed Oct. 4, 2016", 6 pgs.
"U.S. Appl. No. 14/983,021, Restriction Requirement mailed Oct. 4, 2016", 8 pgs.
"U.S. Appl. No. 15/541,737, Advisory Action mailed Dec. 4, 2019", 4 pgs.
"U.S. Appl. No. 15/541,737, Examiner Interview Summary mailed Oct. 3, 2022", 2 pgs.
"U.S. Appl. No. 15/541,737, Final Office Action mailed Apr. 1, 2021", 9 pgs.
"U.S. Appl. No. 15/541,737, Final Office Action mailed May 23, 2019", 11 pgs.
"U.S. Appl. No. 15/541,737, Final Office Action mailed Oct. 31, 2022", 13 pgs.
"U.S. Appl. No. 15/541,737, Non Final Office Action mailed Feb. 14, 2022", 14 pgs.
"U.S. Appl. No. 15/541,737, Non Final Office Action mailed Sep. 14, 2020", 14 pgs.
"U.S. Appl. No. 15/541,737, Non Final Office Action mailed Oct. 5, 2018", 7 pgs.
"U.S. Appl. No. 15/541,737, Response filed Feb. 5, 2019 to Non Final Office Action mailed Oct. 5, 2018", 6 pgs.
"U.S. Appl. No. 15/541,737, Response filed Jul. 7, 2022 to Non Final Office Action mailed Feb. 14, 2022", 7 pgs.
"U.S. Appl. No. 15/541,737, Response filed Sep. 1, 2021 to Final Office Action mailed Apr. 1, 2021", 7 pgs.
"U.S. Appl. No. 15/541,737, Response filed Oct. 22, 2019 to Final Office Action mailed May 23, 2019", 8 pgs.
"U.S. Appl. No. 15/541,737, Response filed Dec. 14, 2020 to Non Final Office Action mailed Sep. 14, 2020", 6 pgs.
"U.S. Appl. No. 15/541,737, Response Filed Aug. 2018 to Restriction Requirement mailed Jun. 11, 2018", 6 pgs.
"U.S. Appl. No. 15/541,737, Restriction Requirement mailed Jun. 11, 2018", 8 pgs.
"U.S. Appl. No. 15/543,816, Non Final Office Action mailed Sep. 3, 2019", 8 pgs.
"U.S. Appl. No. 15/543,816, Notice of Allowance mailed Dec. 20, 2019", 7 pgs.
"U.S. Appl. No. 15/543,816, PTO Response to Rule 312 Communication mailed May 11, 2020", 2 pgs.
"U.S. Appl. No. 15/543,816, Response filed Jun. 10, 2019 to Restriction Requirement mailed Apr. 10, 2019", 7 pgs.
"U.S. Appl. No. 15/543,816, Response Filed Dec. 2, 2019 to Non Final Office Action mailed Sep. 3, 2019", 7 pgs.
"U.S. Appl. No. 15/543,816, Restriction Requirement mailed Apr. 10, 2019", 7 pgs.
"U.S. Appl. No. 15/895,518, Corrected Notice of Allowability mailed Jan. 25, 2019", 2 pgs.
"U.S. Appl. No. 15/895,518, Non Final Office Action mailed Jun. 6, 2018", 28 pgs.
"U.S. Appl. No. 15/895,518, Notice of Allowance mailed Jan. 9, 2019", 7 pgs.
"U.S. Appl. No. 15/895,518, Response filed Sep. 6, 2018 to Non Final Office Action mailed", 8 pgs.
"U.S. Appl. No. 16/385,595, Non Final Office Action mailed Feb. 3, 2020", 22 pgs.
"U.S. Appl. No. 16/426,374, Advisory Action mailed Sep. 22, 2022", 3 pgs.
"U.S. Appl. No. 16/426,374, Final Office Action mailed Jun. 3, 2022", 11 pgs.
"U.S. Appl. No. 16/426,374, Non Final Office Action mailed Oct. 14, 2021", 14 pgs.
"U.S. Appl. No. 16/426,374, Preliminary Amendment filed Jan. 31, 2020", 7 pgs.
"U.S. Appl. No. 16/426,374, Response filed Feb. 14, 2022 to Non Final Office Action mailed Oct. 14, 2021", 8 pgs.
"U.S. Appl. No. 16/426,374, Response filed Aug. 3, 2022 to Final Office Action mailed Jun. 3, 2022", 7 pgs.
"U.S. Appl. No. 16/426,374, Response filed Oct. 3, 2022 to Advisory Action mailed Sep. 22, 2022", 7 pgs.
"U.S. Appl. No. 16/872,923, Non Final Office Action mailed Jan. 6, 2022", 14 pgs.
"U.S. Appl. No. 16/872,923, Preliminary Amendment filed Dec. 16, 2020", 4 pgs.

(56) References Cited

OTHER PUBLICATIONS

"U.S. Appl. No. 16/872,923, Response filed May 6, 2022 to Non Final Office Action mailed Jan. 6, 2022", 8 pgs.
"U.S. Appl. No. 16/872,923, Response filed Nov. 23, 2021 to Restriction Requirement mailed Sep. 28, 2021", 5 pgs.
"U.S. Appl. No. 16/872,923, Restriction Requirement mailed Sep. 28, 2021", 8 pgs.
"U.S. Appl. No. 16/385,595, Preliminary Amendment filed Nov. 26, 2019", 4 pgs.
"U.S. Appl. No. 16/385,595, Supplemental Preliminary Amendment Filed Jan. 24, 2020", 5 pgs.
"U.S. Appl. No. 17/119,384, Response filed Oct. 5, 2022 to Restriction Requirement mailed Sep. 13, 2022", 4 pgs.
"U.S. Appl. No. 17/119,384, Restriction Requirement mailed Sep. 13, 2022", 7 pgs.
"U.S. Appl. No. 17/221,532, Non Final Office Action mailed Dec. 6, 2022", 12 pgs.
"U.S. Appl. No. 17/221,532, Response filed Oct. 5, 2022 to Restriction Requirement mailed Sep. 6, 2022", 4 pgs.
"U.S. Appl. No. 17/221,532, Restriction Requirement mailed Sep. 6, 2022", 9 pgs.
"U.S. Appl. No. 17/260,754, Preliminary Amendment filed Jan. 15, 2021", 6 pgs.
"U.S. Appl. No. 17/436,042, Preliminary Amendment filed Sep. 2, 2021", 7 pgs.
"Application Serial No. 17/620<391, Preliminary Amendment filed Dec. 17, 2021", 6 pgs.
"U.S. Appl. No. 17/920,645, Preliminary Amendment filed Oct. 21, 2022", 6 pgs.
"Australian Application Serial No. 2020233397, First Examination Report mailed Oct. 21, 2022", 4 pgs.
"Chinese Application Serial No. 201680014723.4, Office Action mailed Jun. 1, 2020", w/ English Claims, 8 pgs.
"Chinese Application Serial No. 201680056186.X, Office Action mailed Feb. 22, 2021", with English translation, 16 pgs.
"Chinese Application Serial No. 201680056186.X, Office Action mailed Apr. 22, 2020", w/ English Translation, 21 pgs.
"Chinese Application Serial No. 201680056186.X, Office Action mailed Nov. 16, 2020", with English Translation, 19 pgs.
"Chinese Application Serial No. 201680056186.X, Response filed Jan. 29, 2021 to Office Action mailed Nov. 16, 2020", with English claims, 13 pgs.
"Chinese Application Serial No. 201680056186.X, Response filed Jul. 7, 2021 to Office Action mailed Feb. 22, 2021", w/ English claims, 14 pgs.
"Chinese Application Serial No. 201680056186.X, Response filed Aug. 5, 2021 to Telephone Consultation on Jul. 30, 2021", with English claims, 10 pgs.
"Chinese Application Serial No. 201680056186.X, Response filed Aug. 17, 2020 to Office Action mailed Apr. 22, 2020", w/ English Claims, 7 pgs.
"Chinese Application Serial No. 201680056186.X, Voluntary Amendment Filed Oct. 8, 2018", w/ English Claims, 13 pgs.
"Database WPI Week 201425 Thomson Scientific. London. GB; AN 2014-B65239", (2013), 2 pgs.
"European Application Serial No. 16703375.2, Communication Pursuant to Article 94(3) EPC mailed May 13, 2020", 3 pgs.
"European Application Serial No. 16703375.2, Communication Pursuant to Article 94(3) EPC mailed Dec. 3, 2018", 4 pgs.
"European Application serial No. 16703375.2, Response filed Mar. 12, 2018 to Communication pursuant to Rules 161(1) and 162 EPC mailed Sep. 1, 2017", 11 pgs.
"European Application Serial No. 16703375.2, Resposne Filed Sep. 23, 2019 to Communication Pursuant to Article 94(3) EPC mailed Dec. 3, 2018", 10 pgs.
"European Application Serial No. 16738004.7, Communication Pursuant to Article 94(3) EPC mailed Jul. 19, 2019", 3 pgs.
"European Application Serial No. 16738004.7, Extended European Search Report mailed Oct. 9, 2018", 5 pgs.
"European Application Serial No. 16738004.7, Partial Supplementary European Search Report mailed Jul. 3, 2018", 15 pgs.
"European Application Serial No. 16738004.7, Response Filed May 3, 2019 to Extended European Search Report mailed Oct. 9, 2018", 8 pgs.
"European Application Serial No. 16738004.7, Response filed Nov. 27, 2019 to Communication Pursuant to Article 94(3) EPC mailed Jul. 19, 2019", 78 pgs.
"European Application Serial No. 16738004.7, Response filed Dec. 11, 2017 to Communicaiton Pursuant to Rules 161(2) and 162 EPC mailed Aug. 31, 2017", 7 pgs.
"European Application Serial No. 16757452.4, Communication pursuant to Article 94(3) EPC mailed Mar. 14, 2019", 6 pgs.
"European Application Serial No. 16757452.4, Communication Pursuant to Article 94(3) EPC mailed Mar. 23, 2020", 7 pgs.
"European Application Serial No. 16757452.4, Response filed Aug. 3, 2020 to Communication Pursuant to Article 94(3) EPC mailed Mar. 23, 2020", 9 pgs.
"European Application Serial No. 16757452.4, Response filed Sep. 24, 2019 to Communication pursuant to Article 94(3) EPC mailed Mar. 14, 2019", 10 pgs.
"European Application Serial No. 16757452.4, Response filed Oct. 8, 2018 to Communication Pursuant to Rules 161(1) and 162 EPC mailed Mar. 29, 2018", 14 pgs.
"European Application Serial No. 20716045.8, Response Filed Apr. 19, 2022 to Communication Pursuant to Rules 161(2) and 162 EPC mailed Oct. 15, 2021", 13 pgs.
"Gen Bank Accession No. AAA977434", (Sep. 4, 2018), 2 pgs.
"International Application Serial No. PCT/US2016/012456, International Preliminary Report on Patentability mailed Jul. 20, 2017", 8 pgs.
"International Application Serial No. PCT/US2016/012456, International Search Report mailed Apr. 14, 2016", 6 pgs.
"International Application Serial No. PCT/US2016/012456, Written Opinion mailed Apr. 14, 2016", 7 pgs.
"International Application Serial No. PCT/US2016/013695, International Preliminary Report on Patentability mailed Jul. 27, 2017", 11 pgs.
"International Application Serial No. PCT/US2016/013695, International Search Report mailed Apr. 29, 2016", 3 pgs.
"International Application Serial No. PCT/US2016/013695, Written Opinion mailed Apr. 29, 2016", 3 pgs.
"International Application Serial No. PCT/US2016/047360, International Search Report mailed Nov. 21, 2016", 4 pgs.
"International Application Serial No. PCT/US2016/047360, Supplimentary International Search Report mailed Nov. 30, 2017", 37 pgs.
"International Application Serial No. PCT/US2016/047360, Written Opinion mailed Nov. 21, 2016", 8 pgs.
"International Application Serial No. PCT/US2017/046294, International Preliminary Report on Patentability mailed Feb. 21, 2019", 8 pgs.
"International Application Serial No. PCT/US2017/046294, International Search Report mailed Nov. 21, 2017", 6 pgs.
"International Application Serial No. PCT/US2017/046294, Written Opinion mailed Nov. 21, 2017", 8 pgs.
"International Application Serial No. PCT/US2019/042445, International Preliminary Report on Patentability mailed Jan. 28, 2021", 7 pgs.
"International Application Serial No. PCT/US2019/042445, International Search Report mailed Oct. 23, 2019", 4 pgs.
"International Application Serial No. PCT/US2019/042445, Written Opinion mailed Oct. 23, 2019", 5 pgs.
"International Application Serial No. PCT/US2020/020985, International Preliminary Report on Patentability mailed Sep. 16, 2021", 9 pgs.
"International Application Serial No. PCT/US2020/020985, International Search Report mailed Jun. 22, 2020", 4 pgs.
"International Application Serial No. PCT/US2020/020985, Written Opinion mailed Jun. 22, 2020", 7 pgs.
"International Application Serial No. PCT/US2020/038747, International Preliminary Report on Patentability mailed Dec. 30, 2021", 9 pgs.

(56) References Cited

OTHER PUBLICATIONS

"International Application Serial No. PCT/US2020/038747, International Search Report mailed Oct. 20, 2020", 5 pgs.
"International Application Serial No. PCT/US2020/038747, Written Opinion mailed Oct. 20, 2020", 7 pgs.
"International Application Serial No. PCT/US2020/039373, International Preliminary Report on Patentability mailed Jan. 6, 2022", 15 pgs.
"International Application Serial No. PCT/US2020/057750, International Preliminary Report on Patentability mailed May 12, 2022", 9 pgs.
"International Application Serial No. PCT/US2020/057750, International Search Report mailed Jun. 22, 2021", 7 pgs.
"International Application Serial No. PCT/US2020/057750, Written Opinion mailed Jun. 22, 2021", 7 pgs.
"International Application Serial No. PCT/US2021/028900, International Preliminary Report on Patentability mailed Nov. 3, 2022", 7 pgs.
"International Application Serial No. PCT/US2021/028900, International Search Report mailed Jul. 26, 2021", 7 pgs.
"International Application Serial No. PCT/US2021/028900, Written Opinion mailed Jul. 26, 2021", 5 pgs.
"International Application Serial No. PCT/US2021/046962, International Search Report mailed Jan. 18, 2022", 5 pgs.
"International Application Serial No. PCT/US2021/046962, Written Opinion mailed Jan. 18, 2022", 7 pgs.
"International Application Serial No. PCT/US2021/062913, International Search Report mailed Apr. 19, 2022", 6 pgs.
"International Application Serial No. PCT/US2021/062913, Written Opinion mailed Apr. 19, 2022", 10 pgs.
"International Application Serial No. PCT/US2022/030375, International Search Report mailed Sep. 7, 2022", 7 pgs.
"International Application Serial No. PCT/US2022/030375, Written Opinion mailed Sep. 7, 2022", 9 pgs.
"International Application Serial No. PCT/US2022/034726, International Search Report mailed Oct. 12, 2022", 5 pgs.
"International Application Serial No. PCT/US2022/034726, Written Opinion mailed Oct. 12, 2022", 7 pgs.
"International Application Serial No. PCTUS2016047360 International Preliminary Report on Patentability mailed Mar. 1, 2018", 10 pgs.
"UniProKKB/Swiss-Prot: P10600.1", (Sep. 4, 2018), 6 pgs.
"Visufarma VisudrOp Souzione Oftalmica 10 Falconi Da 0,50ml", Copyright © 2019 Farmacia Loreto Gallo S.R.L., (Mar. 7, 2013), 15 pgs.
Abbas, Aiman, "Formulating Poly(Lactide-co-Glycolide) Particles for Plasmid DNA Delivery", J Pharm Sci, 97(7), (2008), 14 pgs.
Ahmed, K K, et al., "Surface engineering tumor cells with adjuvant-loaded particles for use as cancer vaccines (abstract)", J Control Release, 248, 1-9, (2017), 1 pg.
Aro, Hannu T, et al., "Local delivery of a selective androgen receptor modulator failed as an anabolic agent in a rat bone marrow ablation model", Acta Orthopaedica, vol. 86, [Online]. Retrieved from the Internet: <URL: https://www.ncbi.nlm.nih.gov/pmc/articles/PMC4750778/pdf/iort-86-51.pdf>, (Jan. 1, 2015), 751-759.
Badwaik, V., et al., "Efficient pDNA Delivery Using Cationic 2-Hydroxypropyl-β-Cyclodextrin Pluronic-Based Polyrotaxanes (Abstract)", Macromol Biosci.; 16(1):63-73, (Jan. 2016), 1 pg.
Bahadur, A, et al., "NaCl-triggered self-assembly of hydrophilic poloxamine block copolymers (Abstract)", Int J Pharm .; 494(1):453-62, (Oct. 15, 2015), 1 pg.
Behnoush, Khorsand, et al., "Regeneration of Bone Using Nanoplex Delivery of FGF-2 And BMP-2 Genes in Diaphyseal Long Bone Radial Defects in a Diabetic Rabbit Model", Journal of Controlled Release, Elsevier, Amsterdam, NL, vol. 248, (Jan. 7, 2017), 53-59.
Bian, Liming, et al., "Enhanced MSC chondrogenesis following delivery of TGF-β3 from alginate microspheres within hyaluronic acid hydrogels in vitro and in vivo", Biomaterials, 32(27), (2011), 10 pgs.
Bolin, C A, "Effect of vaccination with a pentavalent leptospiral vaccine containing Leptospira interrogans serovar hardjo type hardjo-bovis on type hardjo-bovis infection of cattle (abstract)", Am J Vet Res, 50, (12), 2004-8., (1989), 1 pg.
Bolin, C A, "Effect of vaccination with a pentavalent leptospiral vaccine on Leptospira interrogans serovar hardjo type hardjo-bovis infection of pregnant cattle (abstract)", Am J Vet Res, 50, (1), 161-5., (1989), 1 pg.
Brouillette, M J, et al., "Strain-Dependent Oxidant Release in Articular Cartilage Originates from Mitochondria", Biomech Model Mechanobiol. 13(3), (Jun. 2014), 565-572.
Brouillette, Marc, "Mechanical Stimulation of Cartilage Induces Mitochondrial Reactive Oxygen Species Production Mediating Metabolic Responses", A thesis submitted in partial fulfillment of the requirements for Doctor of Philosophy degree in Biomedical Engineering in the Graduate College of the University of Iowa, (May 2015), 124 pgs.
Brouillette, Marc James, "Static Compressive Stress Induces Mitochondrial Oxidant Production in Articular Cartilage (Thesis)", A thesis submitted in partial fulfillment of the requirements for the Master of Science degree in Biomedical Engineering in the Graduate College of the University of Iowa, (May 2012), 51 pgs.
Brunori, M., et al., "Nitric oxide and the respiratory enzyme (Abstract)", Biochim Biophys Acta, 1757(9-10), (Sep.-Oct. 2006), 1 pg.
Cao, H, et al., "The Pitx2:miR-200c/141:noggin pathway regulates Bmp signaling and ameloblast differentiation", Development. vol 140. No. 16, (Jul. 17, 2013), 3348-3359.
Chim, Harvey, et al., "Stromal-cell-derived Factor (SDF) 1-alpha in Combination With BMP-2 and TGF-pi Induces Site-Directed Cell Homing and Osteogenic and Chondrogenic Differentiation for Tissue Engineering Without the Requirement for Cell Seeding", Cell Tissue Res, (2012), 6 pgs.
Cochran, "Inflammation and Bone Loss in Periodontal Disease", J Periodontal, col. 79, No. 8, (Aug. 2008), 1569-1576.
Coleman, M, "Complex I inhibition after intra-articular fracture prevents rapid progression of osteoarthritis in a porcine model (Abstract with graphs)", 63rd Annual Meeting of the Orthopaedic Research Society, San Diego, California, (2017), 1 pg.
Coleman, M, et al., "Complex I Inhibition after Intra-articular Fracture Prevents Rapid Progression of Osteoarthritis in a Porcine Model (Poster)", 63rd Annual Meeting of the Orthopaedic Research Society, San Diego, California, (2017), 1 pg.
Coleman, M, et al., "Injurious Loading of Articular Cartilage Compromises Chondrocyte Respiratory Function (Abstract)", Arthritis Rheumatol, 68(3, (2016), 2 pgs.
Coleman, M, et al., "Intraarticular Administration of N-Acetylcysteine Alleviates Acute Oxidative Stress Following Intraarticular Fracture (Abstract)", Oberly Symposium, Iowa City, IA, (2015), 1 pg.
Coleman, M, "Intraarticular Administration of N-Acetylcysteine and Glycyrrhizin Alleviates Acute Oxidative Stress Following Intraarticular Fracture (Abstract)", Orthopaedic Research Societ Annual Meetin , Las Vegas, Nevada, 2015 , 1 pg.
Coleman, M, "Intraarticular Administration of N-Acetylcysteine and Glycyrrhizin Alleviates Acute Oxidative Stress Following Intraarticular Fracture (Abstract)", Orthopaedic Research Society Annual Meeting, Las Vegas, Nevada, (2015), 1 pg.
Coleman, M, "Intraarticular Administration of N-Acetylcysteine and Glycyrrhizin Alleviates Acute Oxidative Stress Following Intraarticular Fracture (Poster)", Orthopaedic Research Society Annual Meeting, Las Vegas, Nevada, (2015), 1 pg.
Coleman, M, "Intraarticular Administration of N-Acetylcysteine Prevents Progression of Post-Traumatic Osteoarthritis in a Large Animal Model of Intraarticular Fracture (Abstract)", Society for Free Radical Biology and Medicine, Boston, Massachusetts, (2015), 1 pg.
Coleman, M, et al., "N-Acetylcysteine Prevents Acute Chondrocyte Injury and Dysfunction Associated with Osteoarthritic Progression after Intraarticular Fracture (Poster)", Military Health System Research Symposium, Fort Lauderdale, Florida, (2015), 1 pg.

(56) References Cited

OTHER PUBLICATIONS

Coleman, M, "Osteoarthritis in Porcine Intraarticular Fracture Model Reveals Mitochondrial Features Similar to Human Disease (Abstract)", Annual Meeting of the Orthopaedic Research Society, Orlando, Florida, (2016), 1 pg.
Coleman, M, "Osteoarthritis in Porcine Intraarticular Fracture Model Reveals Mitochondrial Features Similar to Human Disease (Poster)", Annual Meeting of the Orthopaedic Research Society, Orlando, Florida, (2016), 1 pg.
Coleman, M, et al., "Overloading Healthy Articular Cartilage Induces Mitochondrial Dysfunction Reminiscent of Late Stage Osteoarthritis (Abstract)", Orthopaedic Research Society Annual Meeting, New Orleans, Louisiana, (2014), 1 pg.
Coleman, M, et al., "Overloading Healthy Articular Cartilage Induces Mitochondrial Dysfunction Reminiscent of Late Stage Osteoarthritis (Poster)", Orthopaedic Research Society Annual Meeting, New Orleans, Louisiana, (2014), 1 pg.
Coleman, M, et al., "Targeting mitochondrial responses to intra-articular fracture to prevent posttraumatic osteoarthritis", Science Translational Medicine, 10, Issue 427, (Feb. 2018), 15 pgs.
Coleman, Mitchell, et al., "Complex I Inhibition after Intra-articular Fracture Prevents Rapid Progression of Osteoarthritis in a Porcine Model (Abstract)", OARSI, (2017), 1 pg.
Coleman, Mitchell, et al., "Differential Effects of Superoxide Dismutase Mimetics after Mechanical Overload of Articular Cartilage", Anti-oxidants 6(4), (2017), 10 pgs.
Coleman, Mitchell, et al., "Loading of Articular Cartilage Compromises Chondrocyte Respiratory Function", Arthritis Rheumatol, 68(3), (Mar. 2016), 662-671.
Coleman, Mitchell, "Mitochondrial Responses to Intraarticular Fracture are a Disease-Modifying Target for Post-Traumatic Osteoarthritis Prevention", Nature Medicine, (Mar. 2017), 17 pgs.
Coleman, Mitchell, et al., "N-Acetylcysteine Prevents Acute Chondrocyte Injury and Dysfunction Associated with Osteoarthritic Progression after Intraarticular Fracture (Abstract)", Military Health System Research Symposium, Fort Lauderdale, Florida, (2015), 1 pg.
Coleman, Mitchell, "Three Critical Considerations for Translating Redox Therapies: Location, Location, Location (Presentation)", (2017), 55 pgs.
Compton, Jocelyn, et al., "Sirtuin-1 Augments Chondrogenic Progenitor Cell Activity in an Acute Cartilage Injury Model (Poster)", ORS, (2018), 1 pg.
Crawford, Jeffrey, et al., "Study Design and Rationale for the Phase 3 Clinical Development Program of Enobosarm, a Selective Androgen Receptor Modulator, for the Prevention and Treatment of Muscle Wasting in Cancer Patients (POWER Trials)", Curr Oncol Rep 18: 37, (2016), 11 pgs.
Deleon, Chelsea, et al., "A novel GPER antagonist protects against the formation of estrogen-induced cholesterol gallstones in female mice", Journal of Lipid Research vol. 61, (2020), 767-777.
Diekman, Brian, et al., "Cartilage tissue engineering using differentiated and puri?ed induced pluripotent stem cells", Proc. Nat. Acad. Sci., 109, No. 47, (2012), 19172-19177.
Dimozi, A, et al., "Oxidative Stress Inhibits the Proliferation, Induces Premature Senescence and Promotes a Catabolic Phenotype in Human Nucleus Pulposus Intervertebral Disc Cells", European Cells and Materials vol. 30, (2015), 89-103.
D'Mello, Sheetal, et al., "Bone regeneration using gene-activated matrices", AAPS J., 19(1), (Jan. 2017), 23 pgs.
Dowthwaite, Gary P, et al., "The surface of articular cartilage contains a progenitor cell population", Journal of Cell Science vol. 117, The Company of Biologists, 2004 UK, (2004), 889-897.
Dudley, David, et al., "A synthetic inhibitor of the mitogen-activated protein kinase cascade", Proceedings of the National Academy of Sciences of the United States of America, 92(17), (Aug. 1995), 7686-7689.
Elangovan, et al., "DNA Delivery Strategies to Promote Periodontal Regeneration", J. Biomater. Appl., 25:3, (2010), 11 pgs.
Elangovan, Satheesh, et al., "The enhancement of bone regeneration by gene activated matrix encoding for platelet derived growth factor", Biomaterials, vol. 35, Issue 2, (2014), 737-747.
Ellis, W A, "Leptospirosis, its control, past, present and future", Cattle Practice, 7, (1), (1999), 2 pgs.
Erdinest, Nir, et al., "Anti-Inflammatory Effects of Alpha Linolenic Acid on Human Corneal Epithelial Cells", Investigative Ophthalmology & Visual Science, vol. 53, No. 8, (Jul. 2012), 4396-4406.
Erdmann, Laura, "Synthesis and degradation characteristics of salicylic acid-derived poly(anhydrid-esters)", Biomaterials, 21(19), (Oct. 2000), 1941-1946.
Esquenazi, Salomon, et al., "Topical Combination of NGF and DHA Increases Rabbit Corneal Nerve Regeneration after Photorefractive Keratectomy", Investigative Ophthalmology & Visual Science, vol. 46, No. 9, (Sep. 2005), 3121-3127.
Fakhari, A, et al., "Applications and emerging trends of hyaluronic acid in tissue engineering, as a dermal filler and in osteoarthritis treatment (Abstract)", Acta Biomater, 9:7081, (2013), 1 pg.
Flannery, Carl, et al., "Prevention of Cartilage Degeneration in a Rat Model of Osteoarthritis by Intraarticular Treatment with Recombinant Lubricin", Arthritis Rheum, 60(3), (2009), 11 pgs.
Fredenberg, Susanne, et al., "The mechanisms of drug release in poly(lactic-co-glycolic acid)-based drug delivery systems—A review", International Journal of Pharmaceutics, Elsevier, NL, vol. 415, No. 1, (May 9, 2011), 34-52.
Gai, Dongzheng, et al., "CST6 suppresses osteolytic bone disease in multiple myeloma by blocking osteoclast differentiation", The Journal of Clinical Investigation 132(18), (Sep. 15, 2022), 1-15.
Gao, Wenqing, et al., "Selective Androgen Receptor Modulator Treatment Improves Muscle Strength and Body Composition and Prevents Bone Loss in Orchidectomized Rats", Endocrinology. 146(11), (Nov. 2005), 4887-4897.
Glinka, Y., et al., "Nature of inhibition of mitochondrial respiratory complex I by 6-Hydroxydopamine (Abstract)", J Neurochem. 66(5), (May 1996), 1 pg.
Goetz, Jessica, et al., "Time-Dependent Loss of Mitochondrial Function Precedes Progressive Histologic Cartilage Degeneration in a Rabbit Meniscal Destabilization Model", J Orthop Res., 35(3), (2017), 16 pgs.
Goodwin, Wendy, et al., "Rotenone Prevents Impact-Induced Chondrocyte Death", Journal of Orthopaedic Research 28(8), (2010), 1057-1063.
Hao, S., et al., "Mitochondrion-Targeted Peptide SS-31 Inhibited Oxidized Low-Density Lipoproteins-Induced Foam Cell Formation through both ROS Scavenging and Inhibition of Cholesterol Influx in RAW264.7 Cells (Abstract)", Molecules.; 20(12):21287-97, (Dec. 1, 2015), 1 pg.
Harvey, Chim, et al., "Stromal-cel 1-derived factor (SDF) Ialpha in combination with BMP-2 and TGF-fl induces site-directed cell homing and osteogenic and chondrogenic differentiation for tissue engineering Stromal-cel 1-derived factor (SDF) Ialpha in combination with BMP-2 an", Cell and Tissue Research vol. 350, No. 1, (Jun. 12, 2012), 89-94.
Humphries, Brock, et al., "The microRNA-200 family: small molecules with novel roles in cancer development, progression and therapy", Oncotarget, www.impactjournals.com/oncotarget/, vol. 6, No. 9, (2015), 27 pgs.
Intra, Janjira, et al., "Rational design, fabrication, characterization and in vitro testing of biodegradable microparticles that generate targeted and sustained transgene expression in HepG2 liver cells", Journal of Drug Targeting, 19(6), (2011), 41 pgs.
James, Ad, et al., "The Plasma Membrane Calcium Pump in Pancreatic Cancer Cells Exhibiting the Warburg Effect Relies on Glycolytic ATP (Abstract)", J Biol Chem.; 290(41):24760-71, (Oct. 2015), 1 pg.
Jay, Gregory, et al., "Prevention of cartilage degeneration and restoration of chondroprotection by lubricin tribosupplementation in the rat following anterior cruciate ligament transection", Arthritis & Rheumatism, vol. 62, No. 8, (Aug. 2010), 2382-2391.
Jiao, Lu, et al., "Click Chemistry Functionalized Polymeric Nanoparticles Target Corneal Epithelial Cells through RGD-Cell Surface Receptors", Bioconjugate Chemistry, vol. 20, No. 1, (Jan. 21, 2009), 87-94.

(56) References Cited

OTHER PUBLICATIONS

Jubeck, Brian, et al., "Promotion of Articular Cartilage Matrix Vesicle Mineralization by Type I Collagen", Arthritis Rheum. 58(9), (2008), 2809-2817.
Kerkhofs, S., et al., "Self-Assembly of Pluronic F127-Silica Spherical Core-Shell Nanoparticles in Cubic Close-Packed Structures (Abstract)", Chem Mater.; 27(15):5161-5169, (Aug. 11, 2015), 1 pg.
Khorsand, Behnoush, et al., "A Comparative Study of the Bone Regenerative Effect of Chemically Modified RNA Encoding BMP-2 or BMP-9", The AAPS Journal, vol. 19, No. 2, (Mar. 2017), 438-446.
Kim, Jin-Hong, et al., "Matrix Cross-Linking-Mediated Mechanotransduction Promotes Posttraumatic Osteoarthritis", Proceedings of the National Academy of Sciences, vol. 112, No. 30, Retrieved from the Internet: <URL: https://www.pnas.org/content/pnas/112/30/9424.full.pdf>, (Jul. 28, 2015), 9424-9429.
Kim, T, et al., "Analgesic Effect of Intra-Articular Injection of Temperature-Responsive Hydrogel Containing Bupivacaine on Osteoarthritic Pain in Rats", Biomed Res Int., vol. 2015, Article ID 812949, (2015), 10 pgs.
Kitaori, Toshiyuki, et al., "Stromal Cell-Derived Factor 1/CXCR4 Signaling Is Critical for the Recruitment of Mesenchymal Stem Cells to the Fracture Site During Skeletal Repair in a Mouse Model", Arthritis & Rheumatism, vol. 60, No. 3,, (2009), 813-823.
Koh, Minsoo, et al., "A novel metformin derivative, HL010183, inhibits proliferation and invasion of triple-negative breast cancer cells (Abstract)", vol. 21, Issue 8, (2013), 2 pgs.
Kormann, Michael S. D., et al., "Expression of therapeutic proteins after delivery of chemically modified mRNA in mice", Nature Biotech., 29:154, (2011), 6 pgs.
Korpal, Manav, et al., "The miR-200 Family Inhibits Epithelial-Mesenchymal Transition and Cancer Cell Migration by Direct Targeting of E-cadherin Transcriptional Repressors ZEB1 and ZEB2", Accelerated Publication, The Journal of Biological Chemistry, v. 283, No. 22, May 30, 2008., (May 30, 2008), 14910-14914.
Krishnan, Yamini, "Cartilage Diseases", Matrix Biology, vol. 71-72, (Oct. 1, 2018), 51-69.
L, Perraud, "Accumulation of Free ADP-ribose from Mitochondria Mediates Oxidative Stress-induced Gating of TRPM2 Cation Channels", Journal of Biological Chemistry, vol. 280, No. 7, (Feb. 18, 2005), 6138-6148.
Lacey, et al., "Proinflammatory Cytokines Inhibit Osteogenic Differentiation from Stem Cells: Implications for Bone Repair During Inflammation", Osteoarthritis and Cartilage, vol. 17, (2009), 735-742.
Lee, Changkyu, et al., "Treatment of bleomycin-induced pulmonary fibrosis by inhaled tacrolimus-loaded chitosan-coated polylactic-co-glycolic acid nanoparticles", Biomedicine and Pharmacotherapy Elsevier, FR, vol. 78, XP029423841, ISSN 0753-3322 DOI: 10.1016/J BIOPHA.2016.01.027, (Feb. 2, 2016), 226-233.
Lee, Jin Whan, et al., "Intradiscal drug delivery system for the treatment of low back pain", J Biomed Mater Res A., 92(1), (2009), 378-385.
Lesnak, Joseph, et al., "Select Androgen Receptor Modulator Microparticle Formulation Reverses Muscle Hyperalgesia in Mouse Model of Widespread Muscle Pain", Journal of Pain, Saunders, Philadelphia, PA, US, vol. 23, No. 5, (May 1, 2022), 20 pg.
Liu, et al., "Design and Development of Three-Dimensional Scaffolds For Tissue Engineering", Trans IChemE, Part A, Chemical Engineering Research and Design, (2007), 1051-1064.
Liu, Qin, et al., "Targeted delivery of miR-200c/DOC to inhibit cancer stem cells and cancer cells by the gelatinases-stimuli nanoparticles", Biomaterials. Elsevier Science Publishers Bv. Barking. GB. vol. 34. No. 29, (Jun. 24, 2013), 7191-7203.
Liu, Shirley X.L., et al., "Feasibility of Insulin Eyedrops for Human Use", Journal of Ocular Pharmacology, vol. 10, No. 3, (1994), 587-590.
Lu, Anh S., et al., "Proteolytic Targeting Chimeras with Specificity for Plasma Membrane and Intracellular Estrogen Receptors", Molecular Pharmaceutics 18(3), (2021), 1455-1469.
Lynn, G M, et al., "Impact of Polymer-TLR-7/8 Agonist (Adjuvant) Morphology on the Potency and Mechanism of CD8 T Cell Induction (abstract)", Biomacromolecules, 20, (2), 854-870., (2019), 1 pg.
Martin, James, "Blocking Acute Oxidative Insult to Chondrocytes Prevents Post-Traumatic Osteoarthritis in a Porcine Model of Tibial Plafond Fracture (Abstract of Presentation)", Extremity and War Injuries XI Conference, Washington DC, (2016), 1pg.
Martin, James A, "Intra-Articular Lubricin Gene Therepy for Post-Traumatic Arthritis", Retrieved from the Internet: <URL: https://apps.dtic.mi1/sti/pdfS/AD1011691.pdf> [retrieved on Jun. 1, 2021], (Sep. 1, 2015), 122 pgs.
Martin, James, et al., "N-Acetylcysteine Inhibits Post-Impact Chondrocyte Death in Osteochondral Explants", Journal of Bone and Joint Surgery, vol. 91-A, No. 8, (2009), 1890-1897.
Mendelson, Avital, et al., "Chondrogenesis by chemotactic homing of synovium, bone marrow, and adipose stem cells in vitro", J. FASEB, 25, [Online]. Retrieved from the Internet: <URL: https://www.ncbi.nlm.nih.gov/pmc/articles/PMC3177570/, (2011), 3496-3504.
Mendelson, Avital, et al., "Engineered Nasal Cartilage by Cell Homing: A Model for Augmentative and Reconstructive Rhinoplasty", Plast Reconstr Surg. 133(6), (Jun. 2014), 1344-1353.
Mitchell, A, et al., "(Abstract only) Development of a guided bone regeneration device using salicylic acid-poly(anhydride-ester) polymers and osteoconductive scaffolds.", J Biomed Mater Res A. 102(3), (2014), 1 pg.
Mohammed, M Mohammed, et al., "Evaluation of the Clinical use of Metformin or Pioglitazone in Combination with Meloxicam in Patients with Knee Osteoarthritis; using Knee Injury and Osteoarthritis outcome Score", Iraqi J Pharm Sci, vol. 23, No. 2, (Jan. 14, 2015), 13-26.
Moioli, Eduardo K., et al., "Chondrogenesis of Mesenchymal Stem Cells by Controlled Delivery of Transforming Growth Factor-33", Conf Proc IEEE Eng Med Biol Soc., (2006), 2647-2650.
Moncada, PS, "Nitric Oxide and Oxygen: Actions and Interactions in Health And Disease (Abstract)", Redox Biol.; 5:421, (Aug. 2015), 1 pg.
Morris, Angie S, et al., "Cationic CaMKII Inhibiting Nanoparticles Prevent Allergic Asthma", Molecular Pharmaceutics, vol. 14, No. 6, XP002775413, ISSN 1543-8384, (Jun. 2017), 2166-2175.
Müller, M., et al., "Nanostructured Pluronic hydrogels as bioinks for 3D bioprinting (Abstract)", Biofabrication.; 7(3), (Aug. 2015), 1 pg.
Mustafa, Naziroglu, "New Molecular Mechanisms on the Activation of TRPM2 Channels by Oxidative Stress and ADP-Ribose", Neurochemical Research, Kluwer Academic Publishers-Plenum Publishers, NE vol. 32, No. 11, (Jun. 12, 2007), 1990-2001.
Naguib, Youssef W., et al., "An injectable microparticle formulation for the sustained release of the specific MEK inhibitor PD98059: in vitro evaluation and pharmacokinetics", Drug Delivery and Translational Research, (2020), 182-191.
Naguib, Youssef W., et al., "An injectable microparticle formulation provides long-term inhibition of hypothalamic ERK 1 2 activity and sympathetic excitation in rats with heart failure", Mol Pharm. 17(9), (Sep. 8, 2020), 3643-3648.
Naguib, Youssef W, et al., "Solubilized ubiquinol for preserving corneal function", Biomaterials, Elsevier, Amsterdam, NL, vol. 275,, (May 1, 2021), 14 pgs.
Novakofski, KD, et al., "Joint-dependent response to impact and implications for post-traumatic (Abstract)", Osteoarthritis Cartilage: 23(7):1130-7, (Jul. 2015), 2 pgs.
Oh, K S, et al., "Preclinical studies of ropivacaine extended-release from a temperature responsive hydrogel for prolonged relief of pain at the surgical wound", Int J Pharm, (2019), 225-230.
Pan, Y, et al., "Amino-Modified Polymer Nanoparticles as Adjuvants to Activate the Complement System and to Improve Vaccine Efficacy in Vivo (abstract)", Biomacromolecules, 20, (9), 3575-3583, (2019), 1 pg.
Park, Sang-Hyug, et al., "Tissue-engineered Cartilage Using Fibrin/Hyaluronan Composite Gel and its In Vivo Implantation", Artificial Organs, vol. 29, No. 10, (2005), 838-860.

(56) References Cited

OTHER PUBLICATIONS

Qiu, Weimin, et al., "miR-141-3p inhibits human stromal (mesenchymal) stem cell proliferation and differentiation", Biochimica et Biophysica Acta. Molecular Cell Research, vol. 1843. No. 9., (Sep. 1, 2014), 2114-2121.
Rayner, S.A., et al., "Distribution of integrins alpha v beta 5, alpha v beta 3 and alpha v in normal human cornea: possible implications in clinical and therapeutic adenoviral infection", Eye 12 (Pt 2), (1998), 273-277.
Reddy, T Sanjeeva, et al., "Endothelial cell damage in human and rabbit corneas stored in K-Sol without antioxidants", British Journal of Ophthalmology, 73, (1989), 803-808.
Reimondez-Troitino, Sonia, et al., "Polymeric nanocapsules: a potential New therapy for corneal wound healing", Drug Delivery and Translational Research, Springer, Germany, vol. 6, No. 6, (Jul. 8, 2016), 708-721.
Rey-Rico, Ana, et al., "PEO-PPO-PEO Carriers for rAAV-Mediated Transduction of Human Articular Chondrocytes in Vitro and in a Human Osteochondral Defect Model", Applied Materials & Interfaces, vol. 8, No. 32, (Aug. 3, 2016), 20600-20613.
Rodriguez-Gonzalez, A, et al., "Targeting steroid hormone receptors for ubiquitination and degradation in breast and prostate cancer", Oncogene, vol. 27, No. 57, (Dec. 4, 2008), 19 pgs.
Roma, Mi, et al., "Tetronic® 904-containing polymeric micelles overcome the overexpression of ABCG2 in the blood-brain barrier of rats and boost the penetration of the antiretroviral efavirenz into the CNS (Abstract)", Nanomedicine (Lond).; 10(15):2325-37, (2015), 1 pg.
Ruan, M. Z. C, et al., "Proteoglycan 4 Expression Protects Against the Development of Osteoarthritis", Science Translational Medicine, vol. 5, No. 176, (Mar. 13, 2013), 16 pgs.
Sahoo, Ranjan Ku., et al., "Nonionic Surfactant Vesicles in Ocular Delivery: Innovative Approaches and Perspectives", BioMed Research International, vol. 2014, Article ID 263604, (Jun. 3, 2014), 12 pgs.
Salem, Aliasger K., et al., "Multifunctional nanorods for gene delivery", Nature Materials, vol. 2, (Oct. 2003), 668-671.
Sandez-Macho, I., et al., "Interaction of poloxamine block copolymers with lipid membranes: Role of copolymer structure and membrane cholesterol content (Abstract)", Colloids Surf B Biointerfaces; 133:270-7, (Sep. 2015), 1 pg.
Sauter, Ellen, et al., "Cytoskeletal Dissolution Blocks Oxidant Release and Cell Death in Injured Cartilage", Journal of Orthopaedic Research, 30(4), (2012), 593-598.
Schantz, Jan-Thorsten, et al., "Cell guidance in tissue engineering: SDF-1 mediates site-directed homing of mesenchymal stem cells within three-dimensional polycaprolactone scaffolds. (Abstract)", Tissue Eng. 13(11), [Online]. Retrieved from the Internet: <URL:https://www.ncbi.nlm.nih.gov/pubmed/17961003, (2007), 1 pg.
Seol, D, et al., "Biocompatibility and preclinical feasibility tests of a temperature-sensitive hydrogel for the purpose of surgical wound pain control and cartilage repair", J Biomed Mater Res Part B: Appl Biomater., 101B(8), (Nov. 10, 2013), 1508-15.
Seol, D, et al., "Locally targeted delivery of a micron-size radiation therapy source using temperature-sensitive hydrogel", Int J Radiat Oncol Biol Phys., 88(5), pp. 1142-1147, (2014), 12 pgs.
Sharma, S., et al., "Investigating the role of Pluronic-g-Cationic polyelectrolyte as functional stabilizer for nanocrystals: Impact on Paclitaxel oral bioavailability and tumor growth (Abstract)", Acta Biomater.; 26:169-83, (Oct. 2015), 2 pgs.
Shen, Weiliang, et al., "Intra-Articular Injection of Human Meniscus Stem/Progenitor Cells Promotes Meniscus Regeneration and Ameliorates Osteoarthritis Through Stromal Cell-Derived Factor-1/CXCR4-Mediated Homing", Stem Cells Transl. Med, 3, (2014), 387-394.
Shen, Weiliang, et al., "The effect of incorporation of exogenous stromal cell-derived factor-1 alpha within a knitted silk-collagen sponge scaffold on tendon regeneration (Abstract)", vol. 31, Issue 28, (2010), 1 pg.
Sigaeva, N, et al., "Chemical modification of hyaluronic acid and its application medicine (with machine translation)", vol. 17. No. 3. Herald of Bashkir University, (2012), 1220-1241.
Singh, S R, et al., "Intravenous transferrin, RGD peptide and dual-targeted nanoparticles enhance anti-VEGF intraceptor gene delivery to laser-induced CNV", Gene Therapy, Nature Publishing Group, London, GB, vol. 16, No. 5, (Feb. 5, 2009), 645-659.
Skeie, Jessica M., et al., "Ubiquinol Supplementation of Donor Tissue Enhances Corneal Endothelial Cell Mitochondrial Respiration", Cornea, vol. 39, No. 10, (Oct. 2020), 1285-1290.
Sogame, Yoshihisa, "A comparison of uptake of metformin and phenformin mediated by hOCT1 in human hepatocytes (Abstract)", Biopharm. Drug Dispos., 30:476, (2009), 2 pgs.
Sonada, R B, et al., "Efficacy of leptospiral commercial vaccines on the protection against an autochtonous strain recovered in Brazil (abstract)", Braz J Microbiol, 49, (2), 347-350., (2018), 1 pg.
Sukegawa, Atsushi, et al., "Repair of Rabbit Osteochondral Defects by an Acellular Technique with an Ultrapurified Alginate Gel Containing Stromal Cell-Derived Factor-1 (Abstract)", Tissue Eng. Part A, vol. 18, No. 9-10, [Online]. Retrieved from the Internet: <URL: https://www.liebertpub.com/doi/pdf/10.1089/ten.tea.2011.0380, (2012), 2 pgs.
Suliman, S O, et al., "Polymeric Particles as Cancer Vaccine Vectors", American Pharmaceutical Review, 22, (3), (2019), 5 pgs.
Suzuki, Satoshi, et al., "Excessive reactive oxygen species are therapeutic targets for intervertebral disc degeneration", Arthritis Research & Therapy, 17:316, (2015), 17 pgs.
Tachibana, Atsuko, "Development of Novel Corneal Storage Medium: First Report. Examinations of Rabbit Cornea", Jpn J Ophthalmol 46, (2002), 377-383.
Tahara, et al., "Establishing chitosan coated PLGA nanosphere platform loaded with wide variety of nucleic acid by complexation with cationic compound for gene delivery", International Journal of Pharmaceutics Elsevier Amsterdam NL, ISSN 0378-5173, XP022550511, (Feb. 21, 2008), 210-216.
Takeuchi, et al., "Mucoadhesive nanoparticulate systems for peptide drug Delivery", Advanced Drug Delivery Rev Elsevier Amsterdam NL, vol. 47 no. 1, XP008117909, ISSN 0169-409X DOI: 10 1016/S0169-409X0000120-4, (Mar. 23, 2001), 39-54.
Tam, Hok, et al., "In Vitro Model of Full-Thickness Cartilage Defect Healing", Orthopaedic Research Society, 25, (2007), 1136-1144.
Theodoropoulos, John, et al., "Integration of Tissue-engineered Cartilage with Host Cartilage: An In Vitro Model", Clinical Orthopaedics and Related Res., 469, (2011), 2785-2795.
Thevenot, Paul, et al., "The effect of incorporation of SDF-1alpha into PLGA scaffolds on stem cell recruitment and the inflammatory response", Biomaterials, 31(14), (2010), 3997-4008.
Todd, O McKinley, et al., "Mitochondrial Based Treatments that Prevent Post-Traumatic Osteoarthritis in a Translational Large Animal Intraarticular Fracture Survival Model Principal Investigator: Distribution Statement: Approved for Public Release; Distribution Uniimited", [Online] retrieved from the Internet: <URL: http ://www.dti c.mi 1/get-tr-doc/pdf? Loc ation=U2&doc=GetTRDoc.pdf&AD=ADA592443>, (Jan. 28, 2014), 11 pgs.
Verma, R, et al., "Whole-cell inactivated leptospirosis vaccine: future prospects (abstract)", Hum Vaccin Immunother, 9, (4), 763-5., (2013), 1 pg.
Wafa, E I, et al., "The effect of polyanhydride chemistry in particle-based cancer vaccines on the magnitude of the anti-tumor immune response (abstract)", Acta Biomater, 50, 417-427, (2017), 1 pg.
Wei, et al., "Inhibition of Brain Mitogen-Activated Protein Kinase Signaling Reduces Central Endoplasmic Reticulum Stress and Inflammation and Sympathetic Nerve Activity in Heart Failure Rats", Hypertension, vol. 67, issue 1, (Jan. 2016), 229-236.
Wei, Shun-Guang, et al., "Angiotensin II-triggered p44/42 mitogen-activated protein kinase mediates sympathetic excitation in heart failure rats", Hypertension, 52(2), (2008), 12 pgs.
Wei, Shun-Guang, et al., "Mitogen-activated protein kinases mediate upregulation of hypothalamic angiotensin II type 1 receptors in heart failure rats", Hypertension, 52(4), (2008), 12 pgs.

(56) References Cited

OTHER PUBLICATIONS

Wendlandt, et al., "The role of MicroRNAs miR-200b and miR-200c in TLR4 signaling and NF-iB activation", Innate Immunity, vol. 18, No. 6, (2012), 846-855.
Weng, Yu-Hua, et al., "Nanomicelle-Assisted Targeted Ocular Delivery with Enhanced Antiinflammatory Efficacy In Vivo", Advanced Science, vol. 5, No. 1, (Nov. 10, 2017), 1700455.
Wolff, K, "Mechanical Stress and ATP Synthesis are Coupled by Mitochondrial Oxidants in Articular Cartilage (Abstract)", J Orthop Res 31(2), (2013), 191-196.
Wolff, Katherine, et al., "Mechanical Stress and ATP Synthesis are Coupled by Mitochondrial Oxidants in Articular Cartilage", Journal of Orthopaedic Research, 31(2), (2013), 191-196.
Yongchao, Chu, et al., "Topical ocular delivery to laser-induced choroidal neovascularization by dual internalizing RGD and TAT peptide-modified nanoparticles", International Journal of Nanomedicine, vol. 12, (Feb. 1, 2017), 1353-1368.
Yu, Yang, et al., "Early interference with p44/42 mitogen-activated protein kinase signaling in hypothalamic paraventricular nucleus attenuates angiotensin II-induced hypertension", Hypertension, vol. 61, Issue 4, (Apr. 2013), 13 pgs.
Yu, Yang, et al., "ERK1/2 Mapk signaling in hypothalamic paraventricular nucleus contributes to sympathetic excitation in rats with heart failure after myocardial infarction", American journal of physiology Heart and circulatory physiology, 310(6) H732-H739, (2016), 14 pgs.
Yu, Yin, et al., "Use of Recombinant Human Stromal Cell-Derived Factor 1a-Loaded Fibrin/Hyaluronic Acid Hydrogel Networks to Achieve Functional Repair of Full-Thickness Bovine Articular Cartilage Via Homing of Chondrogenic Progenitor Cells", Arthritis & Rheumatology, vol. 67, No. 5, (May 2015), 1274-1285.
Yu Seok, Youn, et al., "Long-acting inhalable chitosan-coated poly(lactic-co-glycolic acid) nanoparticles containing hydrophobically modified exendin-4 for treating type 2 diabetes", International Journal of Nanomedicine, XP055402101, (Aug. 1, 2013), 9 pgs.
Zhang, W., et al., "Involvement of ROS-mediated mitochondrial dysfunction and SIRT3 down-regulation in tris(2-chloroethyl)phosphate-induced cell cycle arrest (Abstract)", Toxicol Res (Camb).; 5(2):461-470, (Dec. 14, 2015), 1 pg.
Zhang, Wei, et al., "The use of type 1 collagen scaffold containing stromal cell-derived factor-1 to create a matrix environment conducive to partial-thickness cartilage defects repair (Abstract)", Biomaterials, 34:713, [Online]. Retrieved from the Internet: <URL: https://www.sciencedirect.com/science/article/pii/S0142961212011489, (2013), 2 pgs.
Zhang, X, et al., "Comparative study of poly (lactic-co-glycolic acid)-poly ethyleneimine- plasmid DNA microparticles prepared using double emulsion methods (abstract)", J Microencapsul, 25(1), (2008), 2 pgs.
Zhou, Q, et al., "Ibandronate promotes osteogenic differentiation of periodontal ligament stem cells by regulating the expression of microRNA", Biochemical and Biophysical Research Communications. Elsevier. Amsterdam. NL. vol. 404. No. 1, (Jan. 7, 2011), 127-132.
Zimmerman, A D, et al., "Immunity in heifers 12 months after vaccination with a multivalent vaccine containing a United States Leptospira borgpetersenii serovar Hardjo isolate (abstract)", J Am Vet Med Assoc, 242, (11), 1573-7., (2013), 1 pg.
Zuerner, R L, et al., "A Leptospira borgpetersenii serovar Hardjo vaccine induces a Th1 response, activates NK cells, and reduces renal colonization (abstract)", Clin Vaccine Immunol, 18, (4), 684-91., (2011), 1 pg.
"U.S. Appl. No. 17/119,384, Notice of Allowance mailed Sep. 8, 2023", 12 pgs.
"U.S. Appl. No. 17/221,532, Advisory Action mailed Sep. 8, 2023", 3 pgs.
"U.S. Appl. No. 17/221,532, Response filed Aug. 22, 2023 to Final Office Action mailed Jun. 22, 2023", 6 pgs.
"European Application Serial No. 20716045.8, Communication Pursuant to Article 94(3) EPC mailed Aug. 8, 2023", 4 pgs.
U.S. Appl. No. 14/983,021 U.S. Pat. No. 10,335,498, filed Dec. 29, 2015, RNA Based Biomaterial for Tissue Engineering Applications.
U.S. Appl. No. 16/426,374, filed May 30, 2019, RNA Based Biomaterial for Tissue Engineering Applications.
U.S. Appl. No. 15/541,737, filed Jul. 6, 2017, RNA Based Biomaterial for Tissue Engineering Applications.
U.S. Appl. No. 15/543,816 U.S. Pat. No. 10,669,543, filed Jul. 14, 2017, Methods to Prevent or Treat Periodontitis or Peri-Implantitis.
U.S. Appl. No. 15/192,135, filed Jun. 24, 2016, Poly(Lactic-Co-Glycolic Acid) Particles Vaccine to Protect Against House Dust Mite Allergy.
U.S. Appl. No. 17/620,391, filed Dec. 17, 2021, Nanoparticles Comprising Quinone W Methides and Compositions for Use.
U.S. Appl. No. 17/436,042, filed Sep. 2, 2021, Composition Comprising an Anti-Oxidant to Preserve Corneal Tissue.
U.S. Appl. No. 17/260,754, filed Jan. 15, 2021, Implants to Induce Bone Regeneration and Uses Thereof.
U.S. Appl. No. 17/772,450, filed Apr. 27, 2022, Formulation for Delivery of Lubricin Gene.
U.S. Appl. No. 17/119,384, filed Dec. 11, 2020, Poly(Diamino Sulfide) Particle-Based Vaccine.
U.S. Appl. No. 17/920,645, filed Oct. 21, 2022, GPER Proteolytic Targeting Chimeras.
U.S. Appl. No. 17/221,532, filed Apr. 2, 2021, MEK1/2 Inhibitor-Loaded Microparticle Formulation.
U.S. Appl. No. 17/580,129, filed Jan. 20, 2022, Methods to Prevent, Inhibit or Treat Intervertebral Disc Degeneration.
"A Guide Book for Particle Size Analysis", Ed. Horiba Instruments, Inc., (2017), 34 pgs.
"U.S. Appl. No. 17/119,384, Non Final Office Action mailed Dec. 21, 2022", 12 pgs.
"U.S. Appl. No. 17/221,532, Response filed Mar. 6, 2023 to Non Final Office Action mailed Dec. 6, 2022", 6 pgs.
"U.S. Appl. No. 18/042,276, Preliminary Amendment filed Feb. 20, 2023", 7 pgs.
"Canadian Application Serial No. 3,132,533, Examiners Rule 86(2) Report mailed Jan. 18, 2023", 4 pgs.
"European Application Serial No. 20716045.8, Indication of deficiencies in a request under Rule 22 EPC mailed Mar. 22, 2023", 2 pgs.
"International Application Serial No. PCT/US2021/046962, International Preliminary Report on Patentability mailed Mar. 2, 2023", 9 pgs.
"Japanese Application Serial No. 2022-564329, Voluntary Amendment Filed Dec. 7, 2022", W/ English Claims, 12 pgs.
"Leptavoid-H (Intervet/MSD)", MSD Animal Health Republic of Ireland, [Online]. Retrieved from the Internet: <URL: https://www.msd-animal-health.ie/products/leptavoid-h/>, (Accessed Apr. 3, 2023), 1 pg.
"Leptospira Hardjo Bacterin—Material Safety Data Sheet, Version 2.0", Pfizer Animal Health. QC Supply, [Online]. Retrieved from the Internet: <URL: https://www.qcsupply.com/media/product_attachments/attachment_file/5/4/540623MSDS.pd f>, (Revision date Oct. 23, 2009), 1-9.
"Spirovac (Zoetis/Pfizer)", Pfizer Animal Health. QC Supply, [Online]. Retrieved from the Internet: <URL: https://www.qcsupply.com/spirovac-pfizer.html>, (Accessed Apr. 3, 2023), 2 pgs.
Ahmed, K K, et al., "Development and Evaluation of Biodegradable Particles Coloaded with Antigen and the Toll-Like Receptor Agonist, Pentaerythritol Lipid A, as a Cancer Vaccine", Journal of Pharmaceutical Sciences, 105, (2016), 1173-1179.
Ahmed, K K, et al., "Surface engineering tumor cells with adjuvant-loaded particles for use as cancer vaccines", J Control Release, 248, (2017), 1-20.
Bolin, C A, et al., "Effect of vaccination with a pentavalent leptospiral vaccine containing Leptospira interrogans serovar hardjo type hardjo-bovis on type hardjo-bovis infection of cattle", Am J Vet Res, 50(12), (1989), 2004-2008.
Bolin, C A, "Effect of vaccination with a pentavalent leptospiral vaccine on Leptospira interrogans serovar hardjo type hardjo-bovis infection of pregnant cattle", Am J Vet Res, 50 (1), (1989), 161-165.
Carcaboso, A M, et al., "Potent, long lasting systemic antibody levels and mixed Th1/Th2 immune response after nasal immuniza-

(56) References Cited

OTHER PUBLICATIONS tion with malaria antigen loaded PLGA microparticles", Vaccine 22, [Online]. Retrieved from the Internet: <URL: https://doi.org/10.1016/j.vaccine.2003.10.020>, (2004), 1423-1432.
Ganda, Ingrid, et al., "Dendrimer-conjugated Peptide Vaccine Enhances Clearance of Chlamydia Trachomatis Genital Infection", Int J Pharm., 527(1-2), pp. 79-91., [Online]. Retrieved from the Internet: < URL: https://doi.org/10.1016/j.ijpharm.2017.05.045>, (Jul. 15, 2017), 30 pgs.
Geary, Sean, et al., "Diaminosulfide based polymer microparticles as cancer vaccine delivery systems", J Control Release, 220, pp. 682-690, (2015), 23 pgs.
Mutlu, Hatice, et al., "Making the Best of Polymers with Sulfur-Nitrogen Bonds: From Sources to Innovative Materials", Macromol. Rapid Commun., 41, 2000181, (2020), 1-23.
Pan, Y, et al., "Amino-Modifed Polymer Nanoparticles as Adjuvants to Activate the Complement System and to Improve Vaccine Efficacy in Vivo", Biomacromolecules, 20, (2019), 3575-3583.
Rodríguez-Fonseca, Alberto, et al., "In silico search, chemical characterization and immunogenic evaluation of amino-terminated G4-PAMAM-HIV peptide complexes using three-dimensional models of the HIV-1 gp120 protein", Colloids and Surfaces B: Biointerfaces 177, [Online]. Retrieved from the Internet: < URL: https://doi.org/10.1016/j.colsurfb.2019.01.034>, (2019), 77-93.
Sonada, R B, "Efficacy of leptospiral commercial vaccines on the protection against an autochtonous strain recovered in Brazil", Braz J Microbiol, 49(2), (2018), 347-350.
Teixeira, Aline, et al., "Adjuvanted leptospiral vaccines: Challenges and future development of new leptospirosis vaccines", Vaccine, 37, (2019), 3961-3973.
Verma, R, et al., "Whole-cell inactivated leptospirosis vaccine: future prospects", Hum Vaccin Immunother, 9(4), (2013), 763-765.
Wafa, Emad, et al., "Pentaerythritol-based lipid A bolsters the antitumor efficacy of a polyanhydride particle-based cancer vaccine", Nanomedicine, 21: 102055, (2019), 1-25.
Wafa, Emad, et al., "The Effect of Polyanhydride Chemistry in Particle-based Cancer Vaccines on the Magnitude of the Antitumor Immune Response", Acta Biomater., 50, pp. 417-427, (2017), 28 pgs.
Zimmerman, Alicia, et al., "Immunity in heifers 12 months after vaccination with a multivalent vaccine containing a United States Leptospira borgpetersenii serovar Hardjo isolate", J Am Vet Med Assoc, 242, (11), (2013), 1573-1577.
Zuerner, R L, et al., "A Leptospira borgpetersenii serovar Hardjo vaccine induces a Th1 response, activates NK cells, and reduces renal colonization", Clin Vaccine Immunol, 18(4), (2011), 684-691.
"International Application Serial No. PCT/US2020/039373, International Search Report mailed Oct. 16, 2020", 7 pgs.
"International Application Serial No. PCT/US2020/039373, Invitation to Pay Additional Fees mailed Aug. 24, 2020", 17 pgs.
"International Application Serial No. PCT/US2020/039373, Written Opinion mailed Oct. 16, 2020", 13 pgs.
"One-Pot Synthesis of 2-(Aryl/Alkyl)amino-3-cyanobenzo[ b ]thiophenes and Their Hetero-Fused Analogues by Pd-Catalyzed Intramolecular Oxidative C—H Functionalization/Arylthiolation", European Journal of Organic Chemistry, vol. 2017, No. 37, (Oct. 9, 2017), 5679-5688.
Acharya, Anand, et al., "One-Pot Synthesis of Functionalized Benzo[b]thiophenes and Their Hetero-Fused Analogues via Intramolecular Copper-Catalyzed S-Arylation of In Situ Generated Enethiolates", The Journal of Organic Chemistry, vol. 80, No. 5, (Feb. 17, 2015), 2884-2892.
Angell, et al., "N-(3-Cyano-4,5,6,7-tetrahydro-1-benzothien-2-yl)amides as potent, selective, inhibitors of JNK2 and JNK3", Bioorganic & Medicinal Chemistry Letters, vol. 17, No. 5, (Feb. 14, 2007), 1296-1301.
Bandyopadhyay, Debashruti, et al., "Nickel catalyzed site selective C—H functionalization of [alpha]-aryl-thioamides", Organic & Biomolecular Chemistry, vol. 16, No. 35, (Jan. 1, 2018), 6405-6409.
"U.S. Appl. No. 17/260,754, Response filed Nov. 22, 2024 to Non Final Office Action mailed May 22, 2024", 9 pgs.
"U.S. Appl. No. 17/436,042, Restriction Requirement mailed Nov. 21, 2024", 7 pgs.
"U.S. Appl. No. 17/620,391, Restriction Requirement mailed Jul. 3, 2024", 7 pgs.
"U.S. Appl. No. 18/644,608, Preliminary Amendment filed Aug. 15, 2024", 5 pgs.
"U.S. Appl. No. 18/724,851, Preliminary Amendment filed Jun. 27, 2024", 6 pgs.
"European Application Serial No. 22731392.1, Response filed Jul. 18, 2024 to Communication pursuant to Rules 161(1) and 162 EPC mailed Jan. 25, 2024", 19 pgs.
"International Application Serial No. PCT/US2022/082553, International Preliminary Report on Patentability mailed Jul. 11, 2024", 22 pgs.
"Japanese Application Serial No. 2022-564329, Response Filed Jul. 24, 2024 to Notification of Reasons for Refusal mailed Jan. 30, 2024", w/ English Claims, 7 pgs.
"U.S. Appl. No. 17/260,754, Final Office Action mailed Feb. 25, 2025", 16 pgs.
"U.S. Appl. No. 17/436,042, Response filed Jan. 21, 2025 to Restriction Requirement mailed Nov. 21, 2024", 7 pgs.
"U.S. Appl. No. 17/580,129, Non Final Office Action mailed Mar. 24, 2025", 15 pgs.
"U.S. Appl. No. 17/580,129, Response filed Dec. 23, 2024 to Final Office Action mailed Jun. 21, 2024", 9 pgs.
"Australian Application Serial No. 2021259858, Response Filed Nov. 25, 2024 to Second Examiners Report mailed May 17, 2024", w/ Amended Claims, 14 pgs.
"Chinese Application Serial No. 202180044990.7, Office Action mailed Feb. 28, 2025", W/English Translation, 20 pgs.
"Japanese Application Serial No. 2024-210846, Voluntary Amendment Filed Jan. 20, 2025", w/ English Claims, 5 pgs.
"Korean Application Serial No. 10-2022-7040856, Notice of Preliminary Rejection mailed Dec. 20, 2024", 8 pgs.
Adams, Michael, et al., "The internal mechanical functioning of intervertebral discs and articular cartilage, and its relevance to matrix biology", Matrix Biology, 28, (2009), 384-389.
Brodin, Harald, "Paths of Nutrition in Articular Cartilage and Intervertebral Discs", Acta Orthopaedica Scandinavica, 24:1-4,, (1954), 177-183.
Buckwalter, J, et al., "Articular Cartilage and Intervertebral Disc Proteoglycans Differ in Structure: An Electron Microscopic Study", Journal of Orthopaedic Research, vol. 7, No. 1, (1989), 146-151.
Kim, Seoyeon, et al., "Merits of sponge-like PLGA microspheres as long-acting injectables of hydrophobic drug", Journal of Biomaterials Science, Polymer Edition vol. 30, No. 18 1725-1743, (2019), 20 pgs.
Kim, Yuyoung, et al., "How to circumvent untoward drug crystallization during emulsion-templated microencapsulation process", Journal of Applied Polymer Science, (2016). 11 pgs.
Mwale, F, et al., "Distinction Between the Extracellular Matrix of the Nucleus Pulposus and Hyaline Cartilage: A Requisite for Tissue Engineering of Intervertebral Disc", European Cells and Materials, vol. 8, (2004), 58-64.
Temofeew, N. A, "An alternative solution to spinal fusion: Utilizing poloxamer 407 to regenerate the nucleus pulpolsus in the intervertebral disc", ProQuest Dissertations & Theses, (2016).
Tice, Thomas R, et al., "Preparation of Injectable Controlled-Release Microcapsules by a Solvent-Evaporation Process", Journal of Controlled Release 2 343-352, (1985), 10 pgs.
Xueyun, Ma, et al., "Advances in Pathway Researches of G Protein Coupled Estrogen Receptor 1 as a New Estrogen Receptor", Medical Journal of Wuhan University, vol. 39, No. 04, (Jul. 31, 2018), 683-688.
Zheng, D, et al., "Metformin-hydrogel with glucose responsiveness for chronic inflammatory suppression", Chemical Engineering Journal, 428, (2021).
"U.S. Appl. No. 17/772,450, Restriction Requirement mailed May 1, 2025", 12 pgs.
"U.S. Appl. No. 17/436,042, Non Final Office Action mailed May 2, 2025", 9 pgs.

(56) References Cited

OTHER PUBLICATIONS

"Canadian Application Serial No. 3176547 , Voluntary Amendment Filed Apr. 23, 2025", 5 pgs.
"U.S. Appl. No. 17/920,645, Restriction Requirement mailed May 20, 2025", 12 pgs.
"Korean Application Serial No. 10-2022-7040856, Response filed Jun. 19, 2025 to Notice of Preliminary Rejection mailed Dec. 20, 2024", W English Claims, 22 pgs.
"Japanese Application Serial No. 2024-210846, Notification of Reasons for Rejection mailed Jul. 1, 2025", W English Translation, 6 pgs.
"New Zealand Application Serial No. 794317, First Examiner Report mailed Jul. 4, 2025", 3 pgs.
"U.S. Appl. No. 17/920,645, Response filed Jul. 21, 2025 to Restriction Requirement mailed May 20, 2025", 6 pgs.
"U.S. Appl. No. 17/260,754, Response filed Aug. 25, 2025 to Final Office Action mailed Feb. 25, 2025", 10 pgs.
"U.S. Appl. No. 17/920,645, Non Final Office Action mailed Sep. 4, 2025", 23 pgs.
"U.S. Appl. No. 17/580,129, Response filed Sep. 2025 to Non Final Office Action mailed Mar. 24, 2025", 7 pgs.
"Israel Application Serial No. 297486, Office Action mailed Sep. 18, 2025", 4 pgs.
"U.S. Appl. No. 17/580, 129, Final Office Action mailed Oct. 29, 2025", 15 pgs.
"U.S. Appl. No. 18/572,054, Restriction Requirement mailed Oct. 30, 2025", 10 pgs.
"Chinese Application Serial No. 202180044990.7, Response filed Oct. 28, 2025 to Office Action mailed Feb. 28, 2025", W English Claims, 15 pgs.
"U.S. Appl. No. 17/436,042, Response filed Nov. 3, 2025 to Non Final Office Action mailed May 2, 2025", 8 pgs.
"U.S. Appl. No. 17/772,450, Response filed Nov. 3, 2025 to Restriction Requirement mailed May 1, 2025", 7 pgs.
Atluri, Keerthi, "Nanoplex-Mediated Co-delivery of Fibroblast Growth Factor and Bone Morphogenetic Protein Genes Promotes Osteogenesis in Human Adipocyte-Derived Mesenchymal Stem Cells", Mol Pharm 128, 3032-42, 2015, 29 pgs.
Boyce, T, "Allograft bone the influence of processing on safety and performance", Orthopedic Clinics 304 1999 571-581, 1999.
Chakka, Jaidev L, "Polydopamine functionalized VEGF gene-activated 3D printed scaffolds for bone regeneration", RSC Advances, 11, 13282, 2021, 10 pgs.
Churcher, I, "Protac-Induced Protein Degradation in Drug Discovery Breaking the Rules or Just Making New Ones?", J. Med. Chem, 61 pp. 444-452, 2017, 9 pgs.
D'Angelo, Rosa, "Inhibition of osteoclast activity by complement regulation with DF3016A, a novel small-molecular-weight C5aR inhibitor", Biomedicine and Pharmacotherapy 123, 109764, 2020, 9 pgs.
Evans, C H, "Orthopedic gene therapy-lost in translation?", Journal of cellular physiology 2272 2012 416-420, 2012, 12 pgs.
Evans, C H, "Gene therapy for bone healing", Expert reviews in molecular medicine 12 2010, 2010, 22 pgs.
Giannoudis, H, "Bone substitutes an update", Injury 363 2005 S20-S27, 2005, 8 pgs.
Guo, Jiachao, "Perk controls bone homeostasis through the regulation of osteoclast differentiation and function", Cell Death Dis 1110, 847, 2020, 16 pgs.
Itoh, Y, "Design, synthesis and biological evaluation of nuclear receptor-degradation inducers", Bioorganic and Medicinal Chemistry, 9 pp. 6768-6778, 2011, 11 pgs.
Laird, N Z, "Gene- and RNAi-activated scaffolds for bone tissue engineeringCurrent progress and future directions", Adv Drug Deliv Rev 174 2021 613-627, 2021, 31 pgs.
Lee, Donghyun, "Inhibition of Osteoclast Differentiation and Bone Resorption by Bisphosphonate-conjugated Gold Nanoparticles", Sci Rep 6, 27336, 2016, 11 pgs.
Moussa, Nabil Takahiro, "Maxillofacial Bone Grafting Materials", Dent Clin North Am Apr. 2020 642473-490. doi 10.1016 j.cden. 2019.12.011, Feb. 1, 2020, 18 pgs.
Sun, Xiuyun, "A chemical approach for global protein knockdownfrom mice to non-human primates", Cell Discovery, vol. 5, Article No. 10, 2019, 13 pgs.
Tannoury, Chadi A, "Complications with the use of bone morphogenetic protein 2 BMP-2 in spine surgery", Spine J Mar. 2014 1143552-9. doi 10.1016 j.spinee.2013.08.060. Epub Jan. 8, 2014., Mar. 2014, 8 pgs.
Wang, Xin-Fang, "Colony-stimulating factor 1 receptor inhibition prevents against lipopolysaccharide-induced osteoporosis by inhibiting osteoclast formation", Biomedicine and Pharmacotherapy 115, 108916, 2019, 5 pgs.
Woo, E J, "Adverse events reported after the use of recombinant human bone morphogenetic protein 2", Journal of oral and maxillofacial surgery 704 2012 765-767, 2012, 3 pgs.
Yeon, Jeong-Tae, "Idelalisib inhibits osteoclast differentiation and pre-osteoclast migration by blocking the PI3Kd-Akt-c-Fos NFATc1 signaling cascade", Arch Pharm Res 428 pp. 712-721, 2019, 10 pgs.
Zeng, "Proteolysis targeting chimera PROTAC in drug discovery paradigm Recent progress and future challenges", European Journal of Medicinal Chemistry, vol. 210, 112981, 2021, 23 pgs.

* cited by examiner

| Cpd No. | n | R | Cpd No. | n | R |
|---|---|---|---|---|---|
| 2a | 1 | 2-I | 10a | 1 | 2-F |
| 2b | 2 | 2-I | 10b | 2 | 2-F |
| 3a | 1 | 2-Br | 11a | 1 | 2-$C_{10}H_7$ |
| 3b | 2 | 2-Br | 11b | 2 | 2-$C_{10}H_7$ |
| 4a | 1 | 3-Br | 12a | 1 | $C_6H_5$ |
| 4b | 2 | 3-Br | 12b | 2 | $C_6H_5$ |
| 5a | 1 | 4-Br | 13a | 1 | 2-Br$C_6H_4$ |
| 5b | 2 | 4-Br | 13b | 2 | 2-Br$C_6H_4$ |
| 6a | 1 | 2-I | 14a | 1 | 4-$CH_3C_6H_4$ |
| 6b | 2 | 2-I | 14b | 2 | 4-$CH_3C_6H_4$ |
| 7a | 1 | 2-Br | 15a | 1 | 4-$OCH_3C_6H_4$ |
| 7b | 2 | 2-Br | 15b | 2 | 4-$OCH_3C_6H_4$ |
| 8a | 1 | 3-Br | 16a | 1 | 4-n-$C_4H_9C_6H_4$ |
| 8b | 2 | 3-Br | 16b | 2 | 4-n-$C_4H_9C_6H_4$ |
| 9a | 1 | 4-Br | 17a | 1 | $C_6H_5CH_2$ |
| 9b | 2 | 4-Br | 17b | 2 | $C_6H_5CH_2$ |

Figure 1. Synthesis of benzamides 2a,b-5a,b, benzylamines 6a,b-11a,b and ureas 12a,b-17a,b

Figure 2. Formula (I)

X= CO; $CH_2$,CONH; $CONHCH_2$

R= 2-I; 2-Br; 3-Br; 4-Br; 2-F; $C_{10}H_7$; $C_6H_5$; 2-$BrC_6H_4$; 4-$CH_3C_6H_4$; 4-$OCH_3C_6H_4$; 4-n-$C_4H_9C_6H_4$; $C_6H_5CH_2$

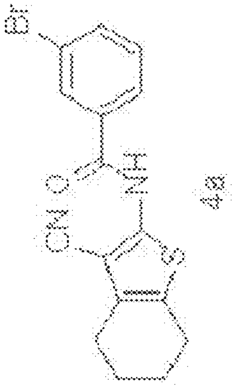
4a
4a (NSC: 813478)
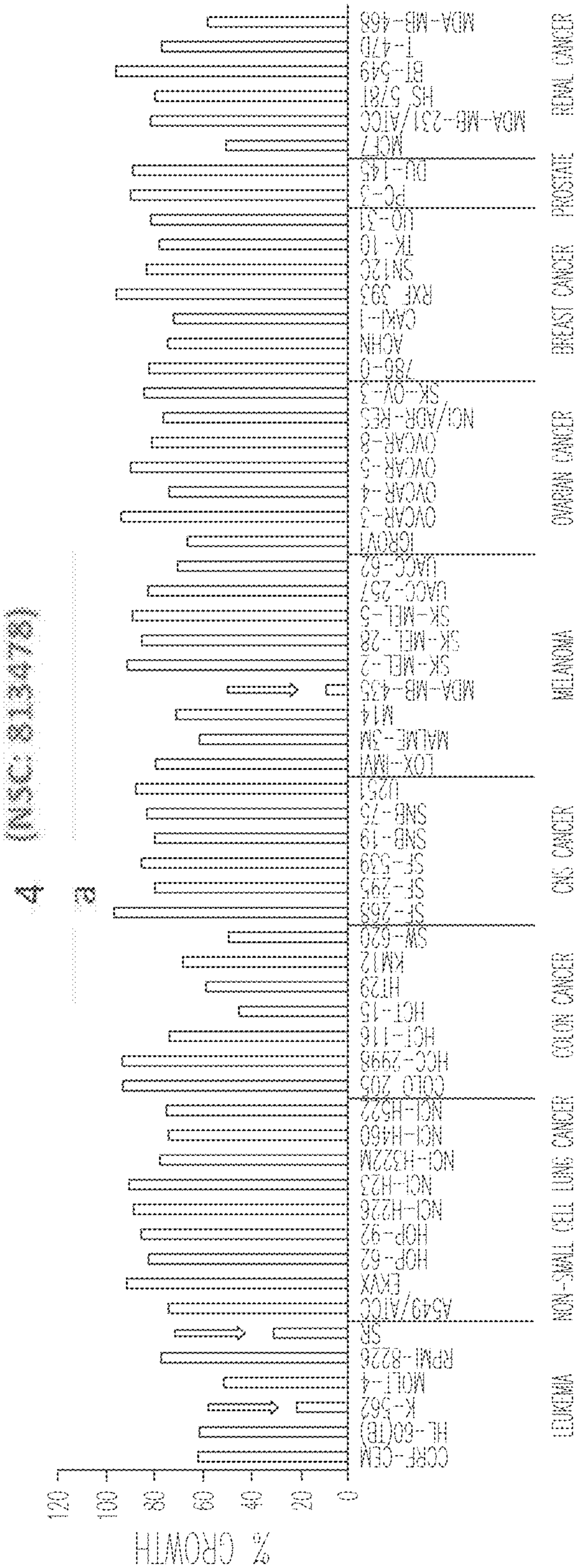
Fig. 3

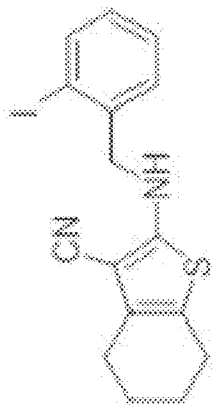
6a
6a (NSC: 813479)
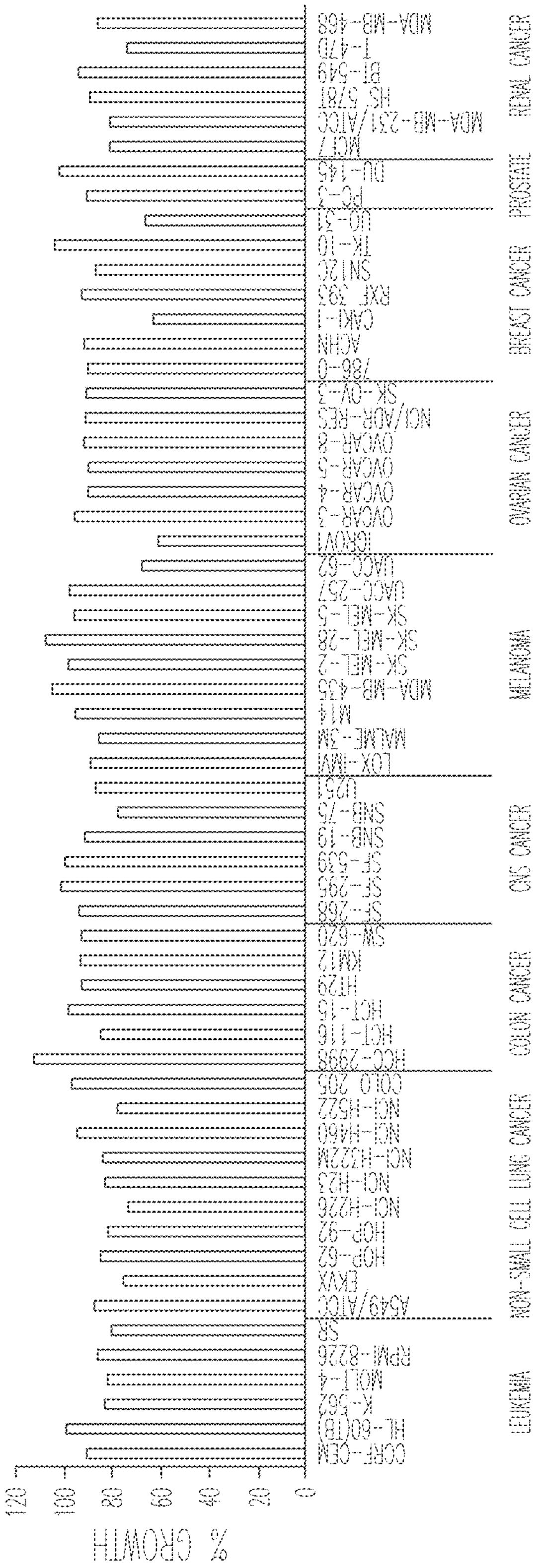
Fig. 4

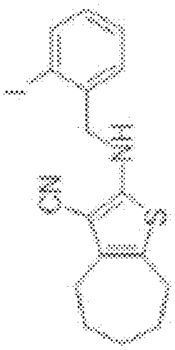
6b
6b (NSC 813480)
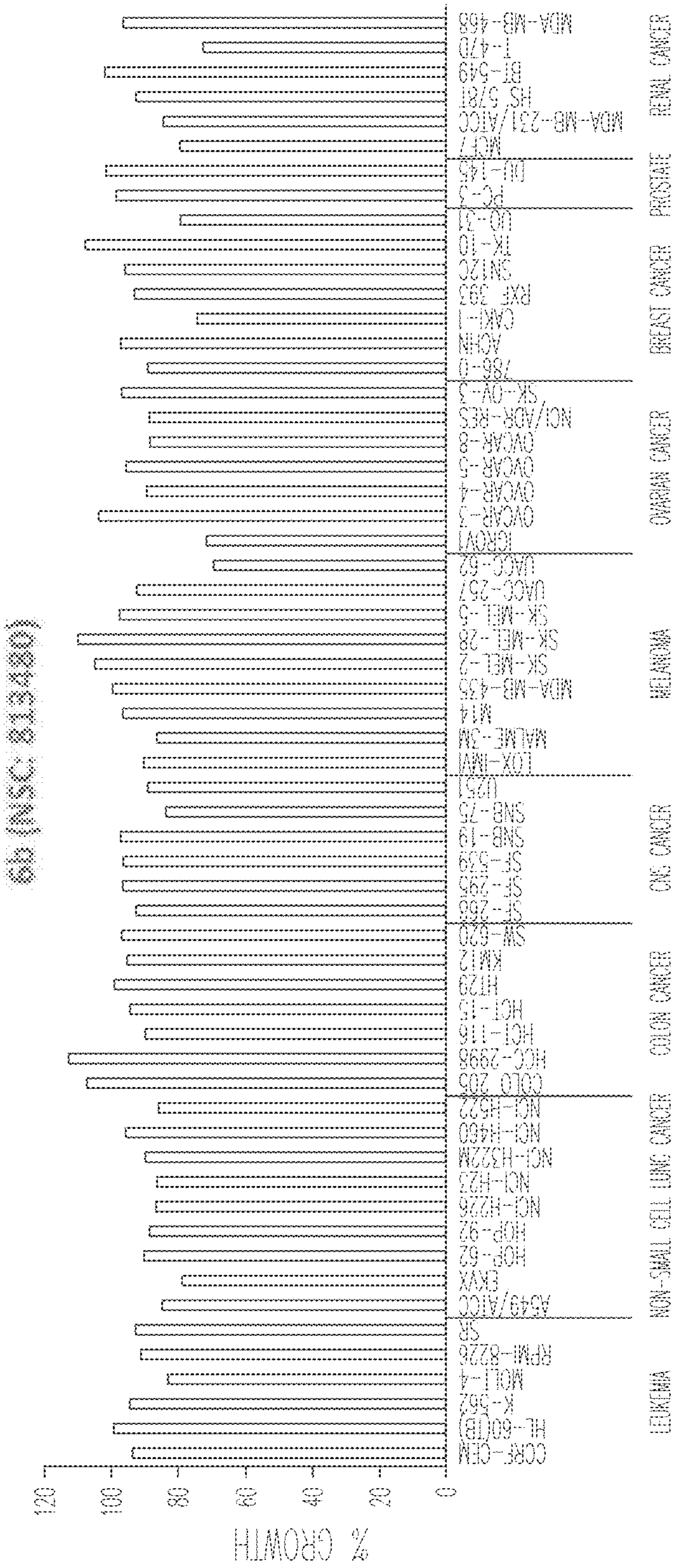
*Fig. 5*

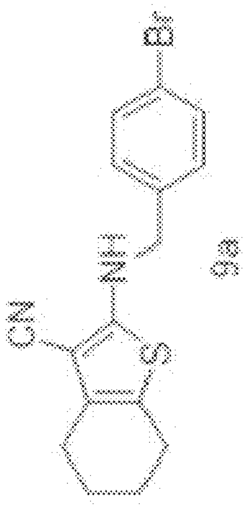
9a
9a (NSC: 814543)
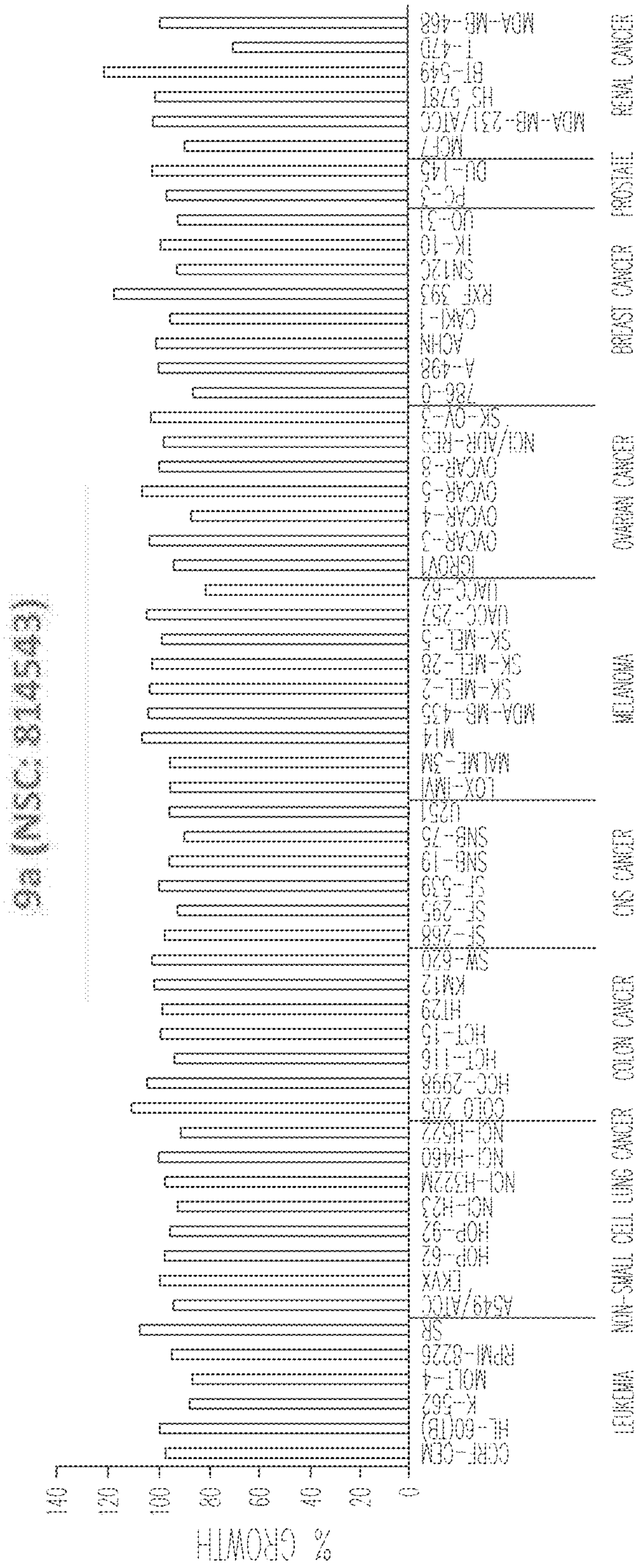
Fig. 6

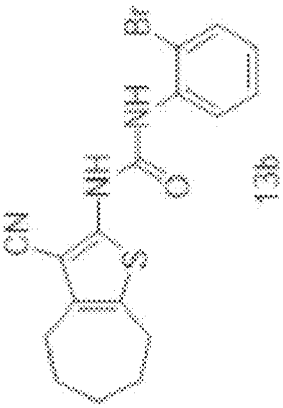
13b
13b (NSC: 813477)
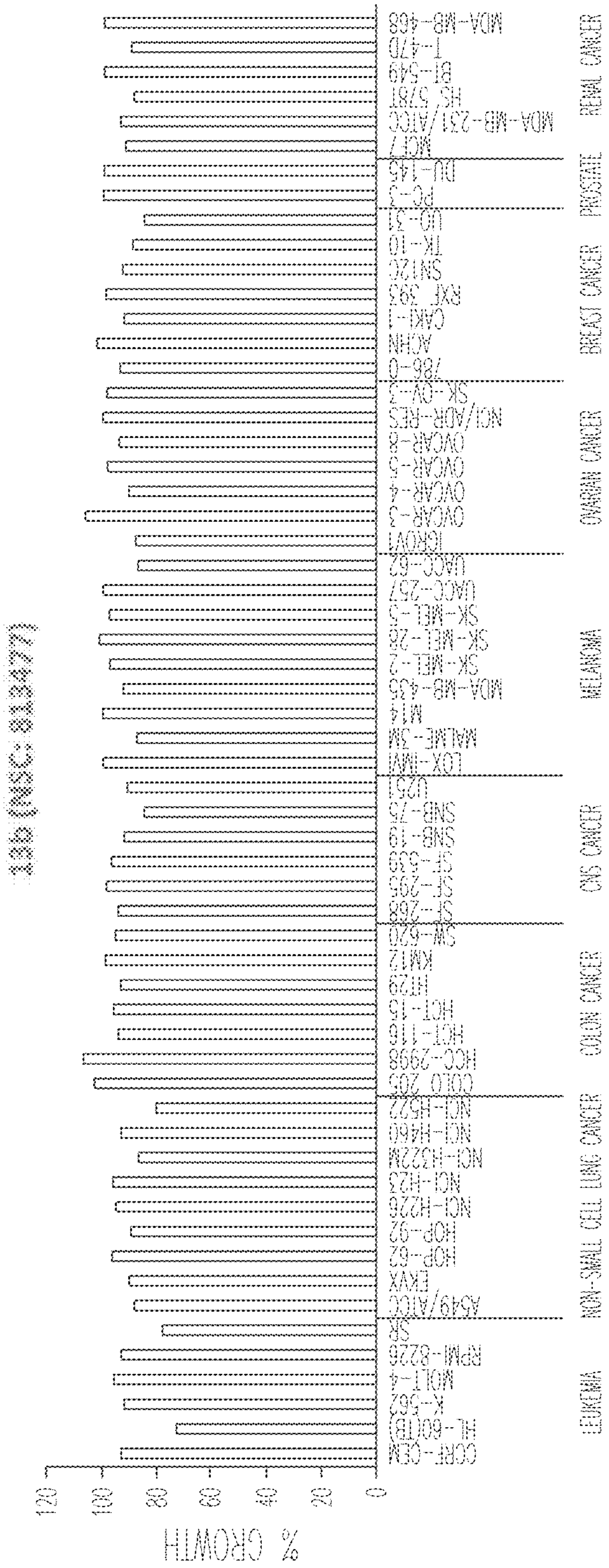
Fig. 7

Figure 8
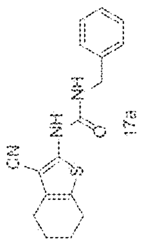
17a
17a (NSC: 813475)
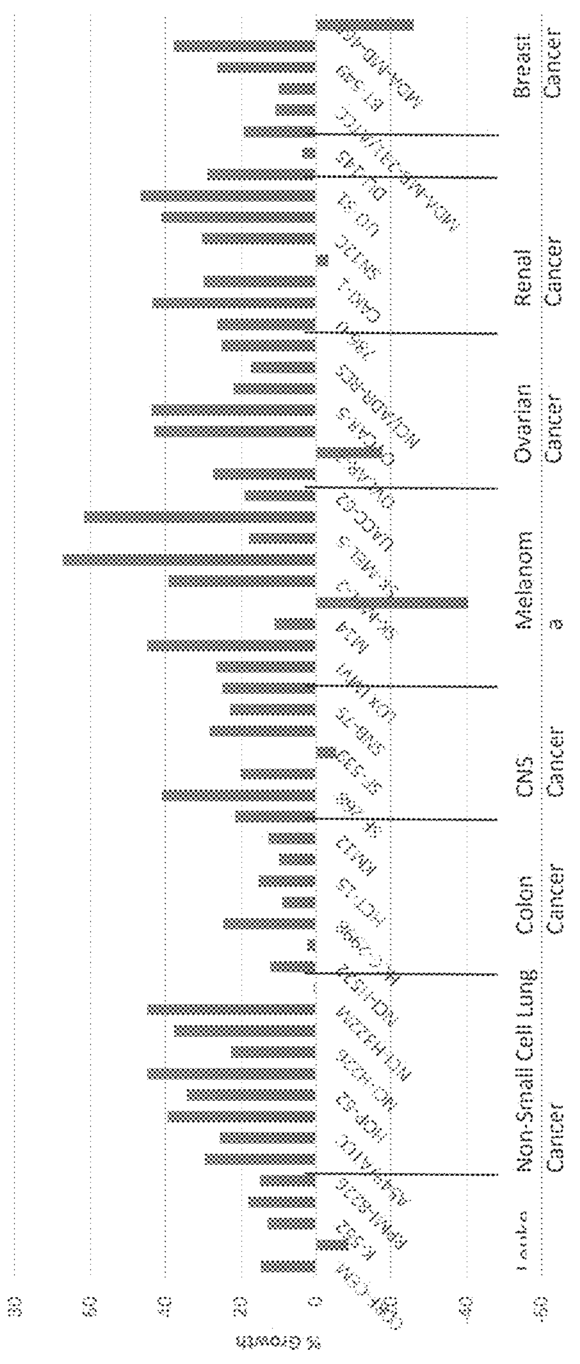

Figure 9

| Cell Lines | $GI_{50}$ values (μM) | Cell Lines | $GI_{50}$ values (μM) |
|---|---|---|---|
| Leukemia | | Melanoma | |
| CCRF-CEM | 0.40738 | M14 | 0.4073 |
| HL-60(TB) | 0.36307 | MDA-MB-435 | 0.1949 |
| K-562 | 0.41687 | SK-MEL-2 | 0.9120 |
| MOLT-4 | 0.46773 | SK-MEL-28 | 1.318256 |
| RPMI-8226 | 0.3981 | SK-MEL-5 | 0.4168 |
| SR | 0.3630 | UACC-257 | >100 |
| Non-Small Cell Lung Cancer | | UACC-62 | 0.3715 |
| A549/ATCC | 0.8128 | Ovarian Cancer | |
| EKVX | 1.6218 | IGROV1 | 0.6760 |
| HOP-62 | 0.7762 | OVCAR-3 | 0.3388 |
| HOP-92 | 0.5370 | OVCAR-4 | 0.9120 |
| NCI-H226 | 0.7585 | OVCAR-5 | 2.754 |
| NCI-H23 | 0.4073 | OVCAR-8 | 2.5703 |
| NCI-H322M | 0.7244 | NCI/ADR-RES | 0.3715 |
| NCI-H460 | 0.3630 | SK-OV-3 | 0.9120 |
| NCI-H522 | 0.3311 | Renal Cancer | |
| Colon Cancer | | 786-0 | 0.6918 |
| COLO 205 | 0.6025 | A498 | 0.1995 |
| HCC-2998 | 1.2882 | ACHN | 0.6606 |
| HCT-116 | 0.5370 | CAKI-1 | 0.8709 |
| HCT-15 | 0.4265 | RXF 393 | 0.3235 |
| HT29 | 0.3801 | SN 12C | 0.6456 |
| KM12 | 0.4073 | TK-10 | 0.1698 |
| SW-620 | 0.3467 | UO-31 | 0.6309 |
| CNS Cancer | | Prostate Cancer | |
| SF-268 | 1.2882 | PC-3 | 0.4365 |
| SF-295 | 0.3890 | DU-145 | 0.7413 |
| SF-539 | 0.3090 | Breast Cancer | |
| SNB-19 | 0.5888 | MCF-7 | 0.3548 |
| SNB-75 | 0.3090 | MDA-MB-231/ATCC | 2.0892 |
| U251 | 0.5888 | HS 578T | 0.4073 |
| Melanoma | | BT-549 | 1.0964 |
| LOX IMVI | 0.5888 | T-47D | ND |
| MALME-3M | 0.4365 | MDA-MB-468 | 0.3630 |

| | Time | | | | Mean Optical Densities | | | | Log10 Concentration |
|---|---|---|---|---|---|---|---|---|---|
| Panel/Cell Line | Zero | Ctrl | -8.0 | -7.0 | -6.0 | -5.0 | -4.0 | | -8.0 |
| Leukemia | | | | | | | | | |
| CCRF-CEM | 0.392 | 2.373 | 2.345 | 2.292 | 0.792 | 0.734 | 0.715 | | 99 |
| HL-60(TB) | 0.974 | 3.338 | 3.357 | 3.336 | 1.244 | 0.998 | 0.894 | | 101 |
| K-562 | 0.262 | 2.721 | 2.665 | 2.641 | 0.791 | 0.586 | 0.518 | | 98 |
| MOLT-4 | 0.579 | 3.077 | 3.145 | 3.049 | 1.224 | 0.983 | 0.927 | | 103 |
| RPMI-8226 | 0.482 | 1.536 | 1.535 | 1.517 | 0.678 | 0.590 | 0.606 | | 100 |
| SR | 0.465 | 2.143 | 2.006 | 1.763 | 0.948 | 0.795 | 0.842 | | 92 |
| Non-Small Cell Lung Cancer | | | | | | | | | |
| A549/ATCC | 0.507 | 2.607 | 2.531 | 2.490 | 1.468 | 0.999 | 0.900 | | 96 |
| EKVX | 0.867 | 2.561 | 2.484 | 2.440 | 1.820 | 1.327 | 1.210 | | 95 |
| HOP-62 | 0.661 | 2.551 | 2.492 | 2.419 | 1.506 | 1.324 | 0.832 | | 97 |
| HOP-92 | 1.406 | 2.017 | 1.955 | 1.859 | 1.658 | 1.535 | 1.298 | | 90 |
| NCI-H226 | 0.905 | 1.591 | 1.521 | 1.571 | 1.203 | 0.942 | 0.744 | | 90 |
| NCI-H23 | 0.679 | 2.377 | 2.312 | 2.314 | 1.032 | 0.652 | 0.617 | | 96 |
| NCI-H322M | 0.822 | 2.227 | 2.123 | 2.134 | 1.428 | 1.318 | 1.181 | | 93 |
| NCI-H460 | 0.316 | 2.951 | 3.022 | 2.951 | 0.609 | 0.385 | 0.320 | | 103 |
| NCI-H522 | 0.843 | 2.245 | 2.069 | 1.843 | 1.265 | 0.989 | 1.039 | | 87 |

Fig. 11A

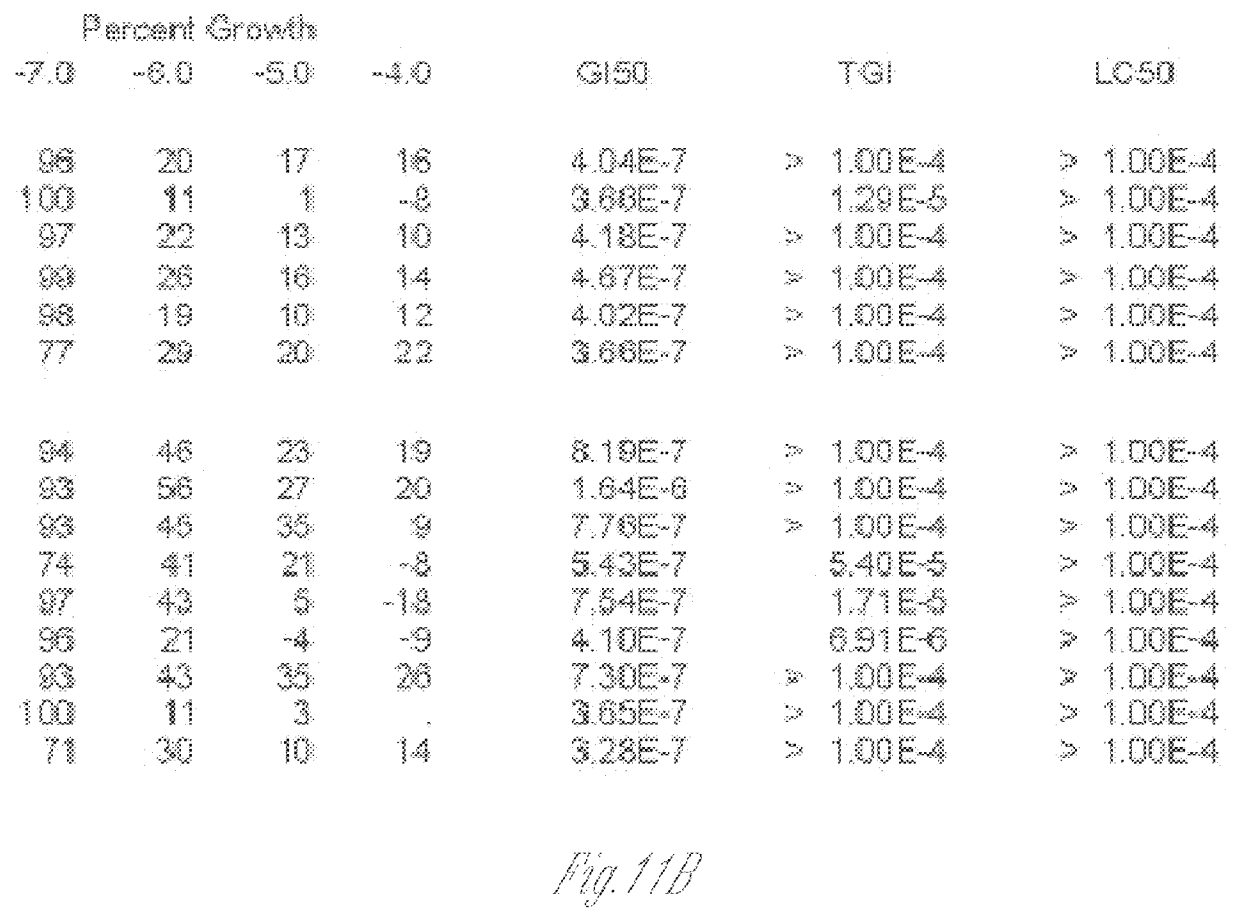

| Percent Growth | | | | | | |
|---|---|---|---|---|---|---|
| -7.0 | -6.0 | -5.0 | -4.0 | GI50 | TGI | LC50 |
| 96 | 20 | 17 | 16 | 4.04E-7 | > 1.00E-4 | > 1.00E-4 |
| 100 | 11 | 1 | -8 | 3.66E-7 | 1.29E-5 | > 1.00E-4 |
| 97 | 22 | 13 | 10 | 4.18E-7 | > 1.00E-4 | > 1.00E-4 |
| 99 | 26 | 16 | 14 | 4.67E-7 | > 1.00E-4 | > 1.00E-4 |
| 98 | 19 | 10 | 12 | 4.02E-7 | > 1.00E-4 | > 1.00E-4 |
| 77 | 29 | 20 | 22 | 3.66E-7 | > 1.00E-4 | > 1.00E-4 |
| | | | | | | |
| 94 | 46 | 23 | 19 | 8.19E-7 | > 1.00E-4 | > 1.00E-4 |
| 93 | 56 | 27 | 20 | 1.64E-6 | > 1.00E-4 | > 1.00E-4 |
| 93 | 46 | 35 | 9 | 7.76E-7 | > 1.00E-4 | > 1.00E-4 |
| 74 | 41 | 21 | -8 | 5.43E-7 | 5.40E-5 | > 1.00E-4 |
| 97 | 43 | 5 | -18 | 7.54E-7 | 1.71E-5 | > 1.00E-4 |
| 96 | 21 | -4 | -9 | 4.10E-7 | 6.91E-6 | > 1.00E-4 |
| 93 | 43 | 35 | 26 | 7.30E-7 | > 1.00E-4 | > 1.00E-4 |
| 100 | 11 | 3 | . | 3.65E-7 | > 1.00E-4 | > 1.00E-4 |
| 71 | 30 | 10 | 14 | 3.28E-7 | > 1.00E-4 | > 1.00E-4 |

*Fig. 11B*

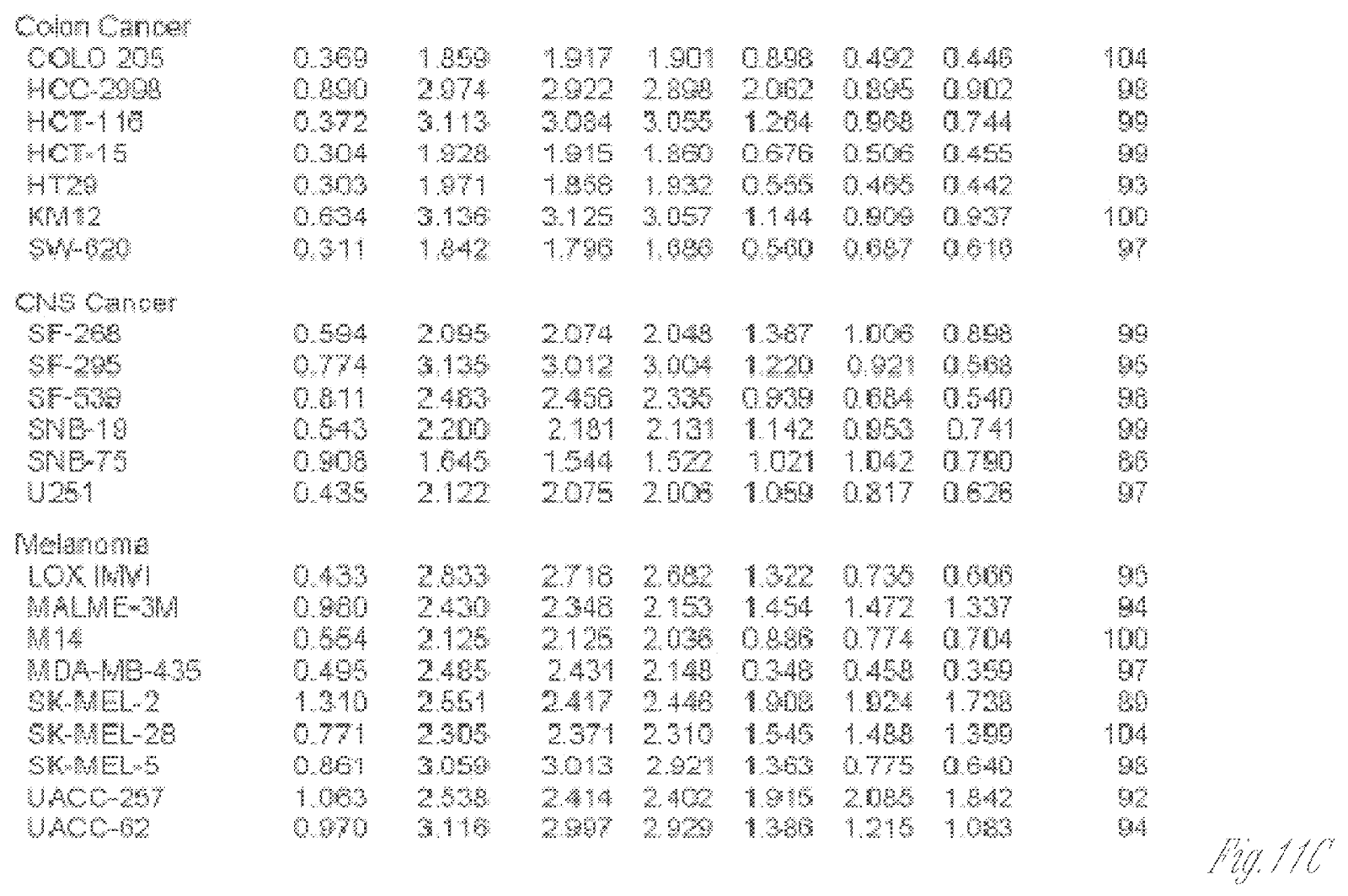

| | | | | | | | | |
|---|---|---|---|---|---|---|---|---|
| Colon Cancer | | | | | | | | |
| COLO 205 | 0.369 | 1.859 | 1.917 | 1.901 | 0.898 | 0.492 | 0.446 | 104 |
| HCC-2998 | 0.890 | 2.974 | 2.922 | 2.898 | 2.062 | 0.895 | 0.902 | 98 |
| HCT-116 | 0.372 | 3.113 | 3.084 | 3.055 | 1.264 | 0.968 | 0.744 | 99 |
| HCT-15 | 0.304 | 1.928 | 1.915 | 1.860 | 0.676 | 0.506 | 0.455 | 99 |
| HT29 | 0.303 | 1.971 | 1.868 | 1.932 | 0.565 | 0.465 | 0.442 | 93 |
| KM12 | 0.634 | 3.136 | 3.125 | 3.057 | 1.144 | 0.909 | 0.937 | 100 |
| SW-620 | 0.311 | 1.842 | 1.796 | 1.686 | 0.560 | 0.687 | 0.616 | 97 |
| CNS Cancer | | | | | | | | |
| SF-268 | 0.594 | 2.095 | 2.074 | 2.048 | 1.367 | 1.006 | 0.898 | 99 |
| SF-295 | 0.774 | 3.135 | 3.012 | 3.004 | 1.220 | 0.921 | 0.568 | 95 |
| SF-539 | 0.811 | 2.463 | 2.458 | 2.335 | 0.939 | 0.684 | 0.540 | 98 |
| SNB-19 | 0.543 | 2.200 | 2.181 | 2.131 | 1.142 | 0.953 | 0.741 | 99 |
| SNB-75 | 0.908 | 1.645 | 1.544 | 1.522 | 1.021 | 1.042 | 0.790 | 86 |
| U251 | 0.435 | 2.122 | 2.075 | 2.006 | 1.059 | 0.817 | 0.626 | 97 |
| Melanoma | | | | | | | | |
| LOX IMVI | 0.433 | 2.833 | 2.718 | 2.682 | 1.322 | 0.735 | 0.606 | 96 |
| MALME-3M | 0.980 | 2.430 | 2.348 | 2.153 | 1.454 | 1.472 | 1.337 | 94 |
| M14 | 0.554 | 2.125 | 2.125 | 2.036 | 0.886 | 0.774 | 0.704 | 100 |
| MDA-MB-435 | 0.495 | 2.485 | 2.431 | 2.148 | 0.348 | 0.458 | 0.359 | 97 |
| SK-MEL-2 | 1.310 | 2.551 | 2.417 | 2.446 | 1.908 | 1.924 | 1.738 | 89 |
| SK-MEL-28 | 0.771 | 2.305 | 2.371 | 2.310 | 1.546 | 1.488 | 1.399 | 104 |
| SK-MEL-5 | 0.861 | 3.059 | 3.013 | 2.921 | 1.363 | 0.775 | 0.640 | 98 |
| UACC-257 | 1.063 | 2.538 | 2.414 | 2.402 | 1.915 | 2.085 | 1.842 | 92 |
| UACC-62 | 0.970 | 3.116 | 2.997 | 2.929 | 1.386 | 1.215 | 1.083 | 94 |

Fig. 11C

| | | | | | | |
|---|---|---|---|---|---|---|
| 103 | 35 | 8 | 5 | 6.09E-7 | > 1.00E-4 | > 1.00E-4 |
| 96 | 56 | . | 1 | 1.29E-6 | > 1.00E-4 | > 1.00E-4 |
| 98 | 33 | 22 | 14 | 5.41E-7 | > 1.00E-4 | > 1.00E-4 |
| 96 | 23 | 12 | 9 | 4.25E-7 | > 1.00E-4 | > 1.00E-4 |
| 98 | 15 | 10 | 8 | 3.78E-7 | > 1.00E-4 | > 1.00E-4 |
| 97 | 20 | 11 | 12 | 4.10E-7 | > 1.00E-4 | > 1.00E-4 |
| 90 | 16 | 25 | 20 | 3.47E-7 | > 1.00E-4 | > 1.00E-4 |
| 97 | 53 | 27 | 20 | 1.29E-6 | > 1.00E-4 | > 1.00E-4 |
| 94 | 19 | 6 | -27 | 3.87E-7 | 1.56E-5 | > 1.00E-4 |
| 91 | 8 | -16 | -33 | 3.11E-7 | 2.13E-6 | > 1.00E-4 |
| 86 | 36 | 25 | 12 | 5.86E-7 | > 1.00E-4 | > 1.00E-4 |
| 83 | 15 | 18 | -13 | 3.09E-7 | 3.81E-5 | > 1.00E-4 |
| 93 | 37 | 23 | 11 | 5.86E-7 | > 1.00E-4 | > 1.00E-4 |
| 94 | 37 | 13 | 10 | 5.91E-7 | > 1.00E-4 | > 1.00E-4 |
| 81 | 33 | 34 | 25 | 4.37E-7 | > 1.00E-4 | > 1.00E-4 |
| 94 | 21 | 14 | 10 | 4.03E-7 | > 1.00E-4 | > 1.00E-4 |
| 83 | -30 | -7 | -27 | 1.96E-7 | 5.44E-7 | > 1.00E-4 |
| 92 | 48 | 49 | 34 | 9.08E-7 | > 1.00E-4 | > 1.00E-4 |
| 100 | 50 | 47 | 41 | 1.33E-6 | > 1.00E-4 | > 1.00E-4 |
| 94 | 23 | -10 | -26 | 4.14E-7 | 4.95E-6 | > 1.00E-4 |
| 91 | 58 | 69 | 53 | > 1.00E-4 | > 1.00E-4 | > 1.00E-4 |
| 91 | 19 | 11 | 5 | 3.76E-7 | > 1.00E-4 | > 1.00E-4 |

Fig. 11D

| | | | | | | | | |
|---|---|---|---|---|---|---|---|---|
| Ovarian Cancer | | | | | | | | |
| IGROV1 | 0.414 | 1.995 | 1.947 | 1.865 | 1.068 | 0.696 | 0.551 | 97 |
| OVCAR-3 | 0.638 | 2.228 | 2.268 | 2.218 | 0.730 | 0.516 | 0.374 | 103 |
| OVCAR-4 | 0.611 | 1.644 | 1.642 | 1.561 | 1.109 | 0.953 | 0.879 | 100 |
| OVCAR-5 | 0.651 | 1.647 | 1.604 | 1.558 | 1.278 | 0.986 | 0.833 | 96 |
| OVCAR-8 | 0.632 | 2.797 | 2.780 | 2.795 | 2.007 | 1.301 | 1.237 | 99 |
| NCI/ADR-RES | 0.679 | 2.423 | 2.388 | 2.313 | 0.986 | 0.693 | 0.605 | 98 |
| SK-OV-3 | 0.685 | 1.990 | 2.006 | 1.951 | 1.311 | 1.266 | 1.014 | 101 |
| Renal Cancer | | | | | | | | |
| 786-0 | 0.683 | 2.755 | 2.665 | 2.616 | 1.545 | 1.147 | 0.975 | 96 |
| A498 | 2.179 | 2.898 | 2.742 | 2.730 | 1.947 | 1.697 | 1.507 | 78 |
| ACHN | 0.404 | 1.808 | 1.847 | 1.809 | 0.953 | 0.749 | 0.670 | 103 |
| CAKI-1 | 1.158 | 3.276 | 3.203 | 3.208 | 2.157 | 2.029 | 1.973 | 97 |
| RXF 393 | 0.939 | 1.527 | 1.537 | 1.477 | 0.995 | 0.844 | 0.540 | 102 |
| SN12C | 0.616 | 2.603 | 2.603 | 2.525 | 1.395 | 1.041 | 0.832 | 100 |
| TK-10 | 0.880 | 2.144 | 2.008 | 1.975 | 1.804 | 1.582 | 1.281 | 89 |
| UO-31 | 0.563 | 1.808 | 1.686 | 1.688 | 1.061 | 1.025 | 1.103 | 90 |
| Prostate Cancer | | | | | | | | |
| PC-3 | 0.477 | 2.188 | 2.241 | 2.153 | 0.879 | 0.860 | 0.733 | 103 |
| DU-145 | 0.452 | 1.858 | 1.924 | 1.848 | 1.056 | 0.513 | 0.458 | 105 |
| Breast Cancer | | | | | | | | |
| MCF7 | 0.544 | 2.760 | 2.574 | 2.539 | 0.921 | 0.823 | 0.863 | 92 |
| MDA-MB-231/ATCC | 0.715 | 1.678 | 1.680 | 1.617 | 1.330 | 0.914 | 0.720 | 101 |
| HS 578T | 1.078 | 2.101 | 2.104 | 2.071 | 1.277 | 1.298 | 1.203 | 100 |
| BT-549 | 1.125 | 2.371 | 2.316 | 2.234 | 1.764 | 1.354 | 1.298 | 96 |
| T-47D | 0.600 | 1.844 | 1.809 | 1.697 | 1.054 | 1.236 | 1.126 | 97 |
| MDA-MB-468 | 0.586 | 1.415 | 1.371 | 1.337 | 0.734 | 0.620 | 0.514 | 95 |

Fig. 11E

Figure 11F:
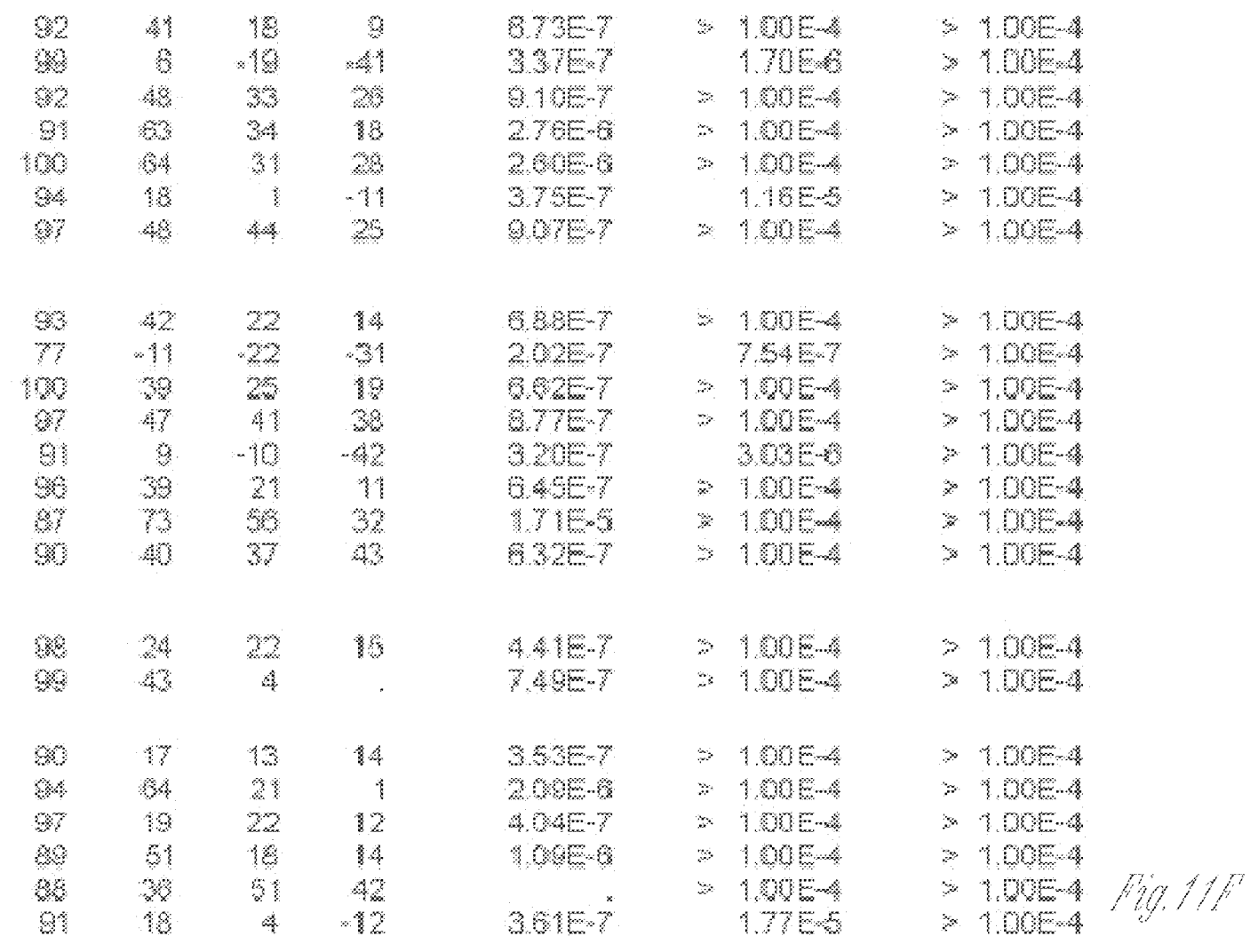

| | | | | | | |
|---|---|---|---|---|---|---|
| 92 | 41 | 18 | 9 | 8.73E-7 | > 1.00E-4 | > 1.00E-4 |
| 99 | 6 | -19 | -41 | 3.37E-7 | 1.70E-6 | > 1.00E-4 |
| 92 | 48 | 33 | 26 | 9.10E-7 | > 1.00E-4 | > 1.00E-4 |
| 91 | 63 | 34 | 18 | 2.76E-6 | > 1.00E-4 | > 1.00E-4 |
| 100 | 64 | 31 | 28 | 2.60E-6 | > 1.00E-4 | > 1.00E-4 |
| 94 | 18 | 1 | -11 | 3.75E-7 | 1.16E-5 | > 1.00E-4 |
| 97 | 48 | 44 | 25 | 9.07E-7 | > 1.00E-4 | > 1.00E-4 |
| | | | | | | |
| 93 | 42 | 22 | 14 | 6.88E-7 | > 1.00E-4 | > 1.00E-4 |
| 77 | -11 | -22 | -31 | 2.02E-7 | 7.54E-7 | > 1.00E-4 |
| 100 | 39 | 25 | 19 | 6.62E-7 | > 1.00E-4 | > 1.00E-4 |
| 97 | 47 | 41 | 38 | 8.77E-7 | > 1.00E-4 | > 1.00E-4 |
| 91 | 9 | -10 | -42 | 3.20E-7 | 3.03E-8 | > 1.00E-4 |
| 96 | 39 | 21 | 11 | 6.45E-7 | > 1.00E-4 | > 1.00E-4 |
| 87 | 73 | 56 | 32 | 1.71E-5 | > 1.00E-4 | > 1.00E-4 |
| 90 | 40 | 37 | 43 | 6.32E-7 | > 1.00E-4 | > 1.00E-4 |
| | | | | | | |
| 98 | 24 | 22 | 15 | 4.41E-7 | > 1.00E-4 | > 1.00E-4 |
| 99 | 43 | 4 | . | 7.49E-7 | > 1.00E-4 | > 1.00E-4 |
| | | | | | | |
| 90 | 17 | 13 | 14 | 3.53E-7 | > 1.00E-4 | > 1.00E-4 |
| 94 | 64 | 21 | 1 | 2.09E-6 | > 1.00E-4 | > 1.00E-4 |
| 97 | 19 | 22 | 12 | 4.04E-7 | > 1.00E-4 | > 1.00E-4 |
| 89 | 51 | 18 | 14 | 1.09E-6 | > 1.00E-4 | > 1.00E-4 |
| 88 | 39 | 51 | 42 | . | > 1.00E-4 | > 1.00E-4 |
| 91 | 18 | 4 | -12 | 3.61E-7 | 1.77E-5 | > 1.00E-4 |

| Cell Lines | $GI_{50}$ values (μM) | Cell Lines | $GI_{50}$ values (μM) |
|---|---|---|---|
| Leukemia | | Melanoma | |
| CCRF-CEM | 0.35 | M14 | 0.392 |
| HL-60(TB) | 0.29 | MDA-MB-435 | 1.72 |
| K-562 | 0.356 | SK-MEL-2 | 0.789 |
| MOLT-4 | 0.393 | SK-MEL-28 | 1.86 |
| RPMI-8226 | 0.362 | SK-MEL-5 | 0.368 |
| SR | 0.329 | UACC-257 | 1.91 |
| Non-Small Cell Lung Cancer | | UACC-62 | 0.493 |
| A549/ATCC | 0.609 | Ovarian Cancer | |
| EKVX | 0.406 | IGROV1 | 0.652 |
| HOP-62 | 0.611 | OVCAR-3 | 0.345 |
| HOP-92 | 0.337 | OVCAR-4 | 0.865 |
| NCI-H226 | 0.712 | OVCAR-5 | 1.85 |
| NCI-H23 | 0.453 | OVCAR-8 | 1.27 |
| NCI-H322M | 0.436 | NCI/ADR-RES | 0.394 |
| NCI-H460 | 0.298 | SK-OV-3 | 0.653 |
| NCI-H522 | 0.500 | Renal Cancer | |
| Colon Cancer | | 786-0 | 0.563 |
| COLO 205 | 0.487 | A498 | 0.176 |
| HCC-2998 | 1.56 | ACHN | 0.631 |
| HCT-116 | 0.538 | CAKI-1 | 0.629 |
| HCT-15 | 0.400 | RXF 393 | 0.262 |
| HT29 | 0.400 | SN 12C | 0.627 |
| KM12 | 0.427 | TK-10 | 0.592 |
| SW-620 | 0.383 | UO-31 | 0.581 |
| CNS Cancer | | Prostate Cancer | |
| SF-268 | 1.22 | PC-3 | 0.388 |
| SF-295 | 0.338 | DU-145 | 0.514 |
| SF-539 | 0.290 | Breast Cancer | |
| SNB-19 | 0.560 | MCF-7 | 0.332 |
| SNB-75 | 0.252 | MDA-MB-231/ATCC | 0.770 |
| U251 | 0.457 | HS 578T | 0.314 |
| Melanoma | | BT-549 | 0.717 |
| LOX IMVI | 0.579 | T-47D | 0.325 |
| MALME-3M | 0.414 | MDA-MB-468 | 0.296 |

| | Time | | Log10 Concentration | | | | | |
|---|---|---|---|---|---|---|---|---|
| | | | Mean Optical Densities | | | | | |
| Panel/Cell Line | Zero | Ctrl | -8.0 | -7.0 | -6.0 | -5.0 | -4.0 | -8.0 |
| Leukemia | | | | | | | | |
| CCRF-CEM | 0.392 | 2.230 | 2.073 | 2.151 | 0.608 | 0.571 | 0.451 | 91 |
| HL-60(TB) | 0.974 | 3.353 | 3.338 | 3.356 | 0.905 | 0.755 | 0.811 | 99 |
| K-562 | 0.262 | 2.607 | 2.572 | 2.517 | 0.555 | 0.414 | 0.375 | 98 |
| MOLT-4 | 0.579 | 2.862 | 2.887 | 2.782 | 0.995 | 0.751 | 0.758 | 101 |
| RPMI-8226 | 0.482 | 1.400 | 1.314 | 1.443 | 0.545 | 0.450 | 0.444 | 91 |
| SR | 0.465 | 2.008 | 1.811 | 1.646 | 0.854 | 0.635 | 0.624 | 87 |
| Non-Small Cell Lung Cancer | | | | | | | | |
| A549/ATCC | 0.507 | 2.655 | 2.567 | 2.567 | 1.310 | 0.665 | 0.763 | 96 |
| EKVX | 0.867 | 2.682 | 2.543 | 2.309 | 1.431 | 1.156 | 1.183 | 92 |
| HOP-62 | 0.661 | 2.495 | 2.382 | 2.439 | 1.344 | 1.179 | 0.724 | 94 |
| HOP-92 | 1.408 | 1.916 | 1.788 | 1.819 | 1.520 | 1.355 | 1.158 | 75 |
| NCI-H226 | 0.905 | 1.540 | 1.493 | 1.643 | 1.150 | 0.875 | 0.708 | 93 |
| NCI-H23 | 0.679 | 2.425 | 2.334 | 2.377 | 1.120 | 0.902 | 0.609 | 95 |
| NCI-H322M | 0.822 | 2.228 | 2.072 | 1.918 | 1.303 | 1.232 | 1.096 | 89 |
| NCI-H460 | 0.316 | 2.706 | 2.752 | 2.416 | 0.510 | 0.317 | 0.213 | 102 |
| NCI-H522 | 0.843 | 2.413 | 2.269 | 2.309 | 1.335 | 0.874 | 0.668 | 92 |

*Fig. 15A*

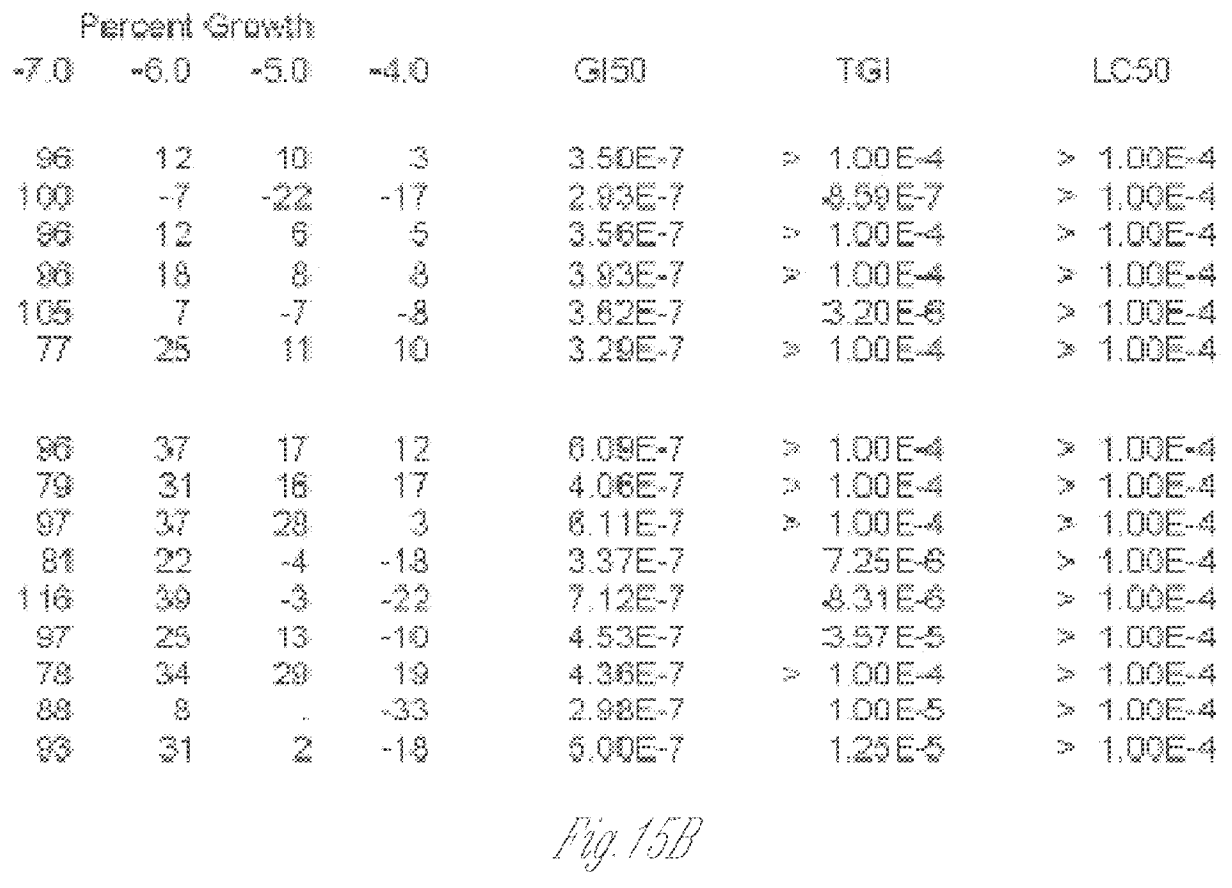

| Percent Growth -7.0 | -6.0 | -5.0 | -4.0 | GI50 | TGI | LC50 |
|---|---|---|---|---|---|---|
| 96 | 12 | 10 | 3 | 3.50E-7 | > 1.00E-4 | > 1.00E-4 |
| 100 | -7 | -22 | -17 | 2.93E-7 | 8.59E-7 | > 1.00E-4 |
| 96 | 12 | 6 | 5 | 3.56E-7 | > 1.00E-4 | > 1.00E-4 |
| 98 | 18 | 8 | 8 | 3.93E-7 | > 1.00E-4 | > 1.00E-4 |
| 105 | 7 | -7 | -8 | 3.62E-7 | 3.20E-6 | > 1.00E-4 |
| 77 | 25 | 11 | 10 | 3.29E-7 | > 1.00E-4 | > 1.00E-4 |
| | | | | | | |
| 96 | 37 | 17 | 12 | 6.09E-7 | > 1.00E-4 | > 1.00E-4 |
| 79 | 31 | 16 | 17 | 4.06E-7 | > 1.00E-4 | > 1.00E-4 |
| 97 | 37 | 28 | 3 | 6.11E-7 | > 1.00E-4 | > 1.00E-4 |
| 81 | 22 | -4 | -18 | 3.37E-7 | 7.25E-6 | > 1.00E-4 |
| 116 | 39 | -3 | -22 | 7.12E-7 | 8.31E-6 | > 1.00E-4 |
| 97 | 25 | 13 | -10 | 4.53E-7 | 3.57E-5 | > 1.00E-4 |
| 78 | 34 | 29 | 19 | 4.36E-7 | > 1.00E-4 | > 1.00E-4 |
| 88 | 8 | . | -33 | 2.98E-7 | 1.00E-5 | > 1.00E-4 |
| 93 | 31 | 2 | -18 | 5.00E-7 | 1.25E-5 | > 1.00E-4 |

*Fig. 15B*

| | | | | | | | | |
|---|---|---|---|---|---|---|---|---|
| Colon Cancer | | | | | | | | |
| COLO 205 | 0.369 | 1.758 | 1.743 | 1.763 | 0.747 | 0.317 | 0.332 | 99 |
| HCC-2998 | 0.890 | 2.918 | 2.732 | 2.032 | 2.177 | 0.834 | 0.782 | 91 |
| HCT-116 | 0.372 | 3.019 | 2.995 | 2.997 | 1.217 | 0.012 | 0.495 | 99 |
| HCT-15 | 0.304 | 1.970 | 1.885 | 1.872 | 0.652 | 0.375 | 0.327 | 95 |
| HT29 | 0.303 | 1.974 | 1.941 | 2.069 | 0.527 | 0.395 | 0.340 | 98 |
| KM12 | 0.634 | 3.055 | 3.040 | 3.028 | 1.152 | 0.798 | 0.705 | 99 |
| SW-620 | 0.311 | 1.646 | 1.618 | 1.606 | 0.530 | 0.629 | 0.488 | 98 |
| CNS Cancer | | | | | | | | |
| SF-268 | 0.594 | 2.069 | 1.978 | 2.025 | 1.378 | 0.851 | 0.699 | 94 |
| SF-295 | 0.774 | 3.141 | 2.917 | 2.957 | 1.070 | 0.812 | 0.537 | 91 |
| SF-539 | 0.811 | 2.449 | 2.355 | 2.453 | 0.743 | 0.614 | 0.449 | 94 |
| SNB-19 | 0.543 | 2.132 | 2.070 | 2.128 | 1.072 | 0.870 | 0.628 | 96 |
| SNB-75 | 0.908 | 1.542 | 1.422 | 1.464 | 0.851 | 0.828 | 0.634 | 81 |
| U251 | 0.435 | 2.036 | 1.932 | 2.003 | 0.841 | 0.669 | 0.442 | 94 |
| Melanoma | | | | | | | | |
| LOX IMVI | 0.433 | 2.846 | 2.665 | 2.775 | 1.286 | 0.705 | 0.664 | 92 |
| MALME-3M | 0.980 | 2.373 | 2.294 | 2.267 | 1.352 | 1.109 | 1.282 | 94 |
| M14 | 0.554 | 2.006 | 1.895 | 2.035 | 0.764 | 0.644 | 0.589 | 92 |
| MDA-MB-435 | 0.495 | 2.225 | 2.139 | 1.972 | 0.178 | 0.319 | 0.195 | 95 |
| SK-MEL-2 | 1.310 | 2.688 | 2.713 | 2.765 | 1.911 | 1.796 | 1.408 | 102 |
| SK-MEL-28 | 0.771 | 2.322 | 2.298 | 2.404 | 1.612 | 1.370 | 1.333 | 98 |
| SK-MEL-5 | 0.861 | 2.994 | 2.894 | 2.922 | 1.166 | 0.461 | 0.453 | 95 |
| UACC-257 | 1.063 | 2.549 | 2.492 | 2.472 | 1.903 | 1.559 | 1.627 | 96 |
| UACC-62 | 0.970 | 3.132 | 3.040 | 3.038 | 1.615 | 1.017 | 0.890 | 96 |

Fig. 15C

| | | | | | | |
|---|---|---|---|---|---|---|
| 100 | 27 | -14 | -10 | 4.87E-7 | 4.56E-6 | > 1.00E-4 |
| 101 | 63 | -6 | -12 | 1.56E-6 | 8.11E-6 | > 1.00E-4 |
| 89 | 32 | 9 | 5 | 5.38E-7 | > 1.00E-4 | > 1.00E-4 |
| 94 | 21 | 4 | 1 | 4.00E-7 | > 1.00E-4 | > 1.00E-4 |
| 105 | 13 | 6 | 2 | 4.00E-7 | > 1.00E-4 | > 1.00E-4 |
| 99 | 21 | 7 | 3 | 4.27E-7 | > 1.00E-4 | > 1.00E-4 |
| 97 | 16 | 24 | 13 | 3.83E-7 | > 1.00E-4 | > 1.00E-4 |
| | | | | | | |
| 97 | 53 | 17 | 7 | 1.22E-6 | > 1.00E-4 | > 1.00E-4 |
| 92 | 13 | 2 | -31 | 3.38E-7 | 1.12E-5 | > 1.00E-4 |
| 100 | -8 | -24 | -45 | 2.90E-7 | 8.37E-7 | > 1.00E-4 |
| 100 | 33 | 21 | 5 | 5.60E-7 | > 1.00E-4 | > 1.00E-4 |
| 88 | -6 | -9 | -30 | 2.52E-7 | 8.57E-7 | > 1.00E-4 |
| 98 | 25 | 15 | . | 4.57E-7 | > 1.00E-4 | > 1.00E-4 |
| | | | | | | |
| 97 | 35 | 11 | 10 | 5.79E-7 | > 1.00E-4 | > 1.00E-4 |
| 92 | 27 | 9 | 22 | 4.41E-7 | > 1.00E-4 | > 1.00E-4 |
| 102 | 14 | 6 | 2 | 3.92E-7 | > 1.00E-4 | > 1.00E-4 |
| 85 | -64 | -36 | -61 | 1.72E-7 | 3.72E-7 | . |
| 106 | 44 | 35 | 7 | 7.89E-7 | > 1.00E-4 | > 1.00E-4 |
| 105 | 54 | 39 | 36 | 1.86E-6 | > 1.00E-4 | > 1.00E-4 |
| 97 | 14 | -47 | -47 | 3.68E-7 | 1.72E-6 | > 1.00E-4 |
| 95 | 57 | 33 | 38 | 1.91E-6 | > 1.00E-4 | > 1.00E-4 |
| 96 | 30 | 2 | -8 | 4.93E-7 | 1.62E-5 | > 1.00E-4 |

*Fig. 15D*

| | | | | | | | | |
|---|---|---|---|---|---|---|---|---|
| Ovarian Cancer | | | | | | | | |
| IGROV1 | 0.414 | 1.902 | 1.848 | 1.885 | 0.992 | 0.584 | 0.456 | 96 |
| OVCAR-3 | 0.638 | 2.146 | 2.219 | 2.155 | 0.736 | 0.535 | 0.264 | 105 |
| OVCAR-4 | 0.611 | 1.552 | 1.526 | 1.560 | 1.050 | 0.859 | 0.698 | 97 |
| OVCAR-5 | 0.651 | 1.598 | 1.536 | 1.566 | 1.196 | 0.927 | 0.846 | 93 |
| OVCAR-8 | 0.632 | 2.759 | 2.747 | 2.788 | 1.755 | 1.185 | 1.090 | 99 |
| NCI/ADR-RES | 0.679 | 2.361 | 2.280 | 2.344 | 0.980 | 0.733 | 0.528 | 95 |
| SK-OV-3 | 0.685 | 1.981 | 1.938 | 1.946 | 1.194 | 1.058 | 0.865 | 97 |
| Renal Cancer | | | | | | | | |
| 786-0 | 0.683 | 2.723 | 2.646 | 2.812 | 1.401 | 0.791 | 0.891 | 96 |
| A498 | 2.179 | 2.812 | 2.654 | 2.632 | 1.833 | 1.587 | 1.328 | 75 |
| ACHN | 0.404 | 1.788 | 1.804 | 1.840 | 0.910 | 0.659 | 0.614 | 101 |
| CAKI-1 | 1.158 | 3.200 | 3.088 | 3.102 | 1.947 | 1.469 | 1.465 | 95 |
| RXF 393 | 0.939 | 1.563 | 1.523 | 1.539 | 0.809 | 0.615 | 0.419 | 94 |
| SN12C | 0.616 | 2.525 | 2.437 | 2.479 | 1.340 | 0.989 | 0.656 | 95 |
| TK-10 | 0.880 | 2.089 | 1.897 | 1.893 | 1.729 | 1.412 | 1.178 | 84 |
| UO-31 | 0.563 | 1.784 | 1.652 | 1.729 | 1.003 | 0.819 | 0.807 | 89 |
| Prostate Cancer | | | | | | | | |
| PC-3 | 0.477 | 1.962 | 1.913 | 1.934 | 0.720 | 0.846 | 0.552 | 97 |
| DU-145 | 0.452 | 1.751 | 1.753 | 1.817 | 0.811 | 0.425 | 0.325 | 100 |
| Breast Cancer | | | | | | | | |
| MCF7 | 0.544 | 2.730 | 2.510 | 2.451 | 0.889 | 0.767 | 0.803 | 90 |
| MDA-MB-231/ATCC | 0.715 | 1.669 | 1.572 | 1.540 | 1.148 | 0.749 | 0.584 | 90 |
| HS 578T | 1.078 | 1.940 | 1.854 | 1.872 | 1.143 | 1.076 | 1.011 | 90 |
| BT-549 | 1.125 | 2.368 | 2.210 | 2.156 | 1.677 | 1.260 | 1.282 | 87 |
| T-47D | 0.600 | 1.785 | 1.613 | 1.509 | 0.892 | 1.087 | 1.046 | 85 |
| MDA-MB-468 | 0.586 | 1.377 | 1.332 | 1.279 | 0.649 | 0.507 | 0.499 | 94 |

Fig. 15E

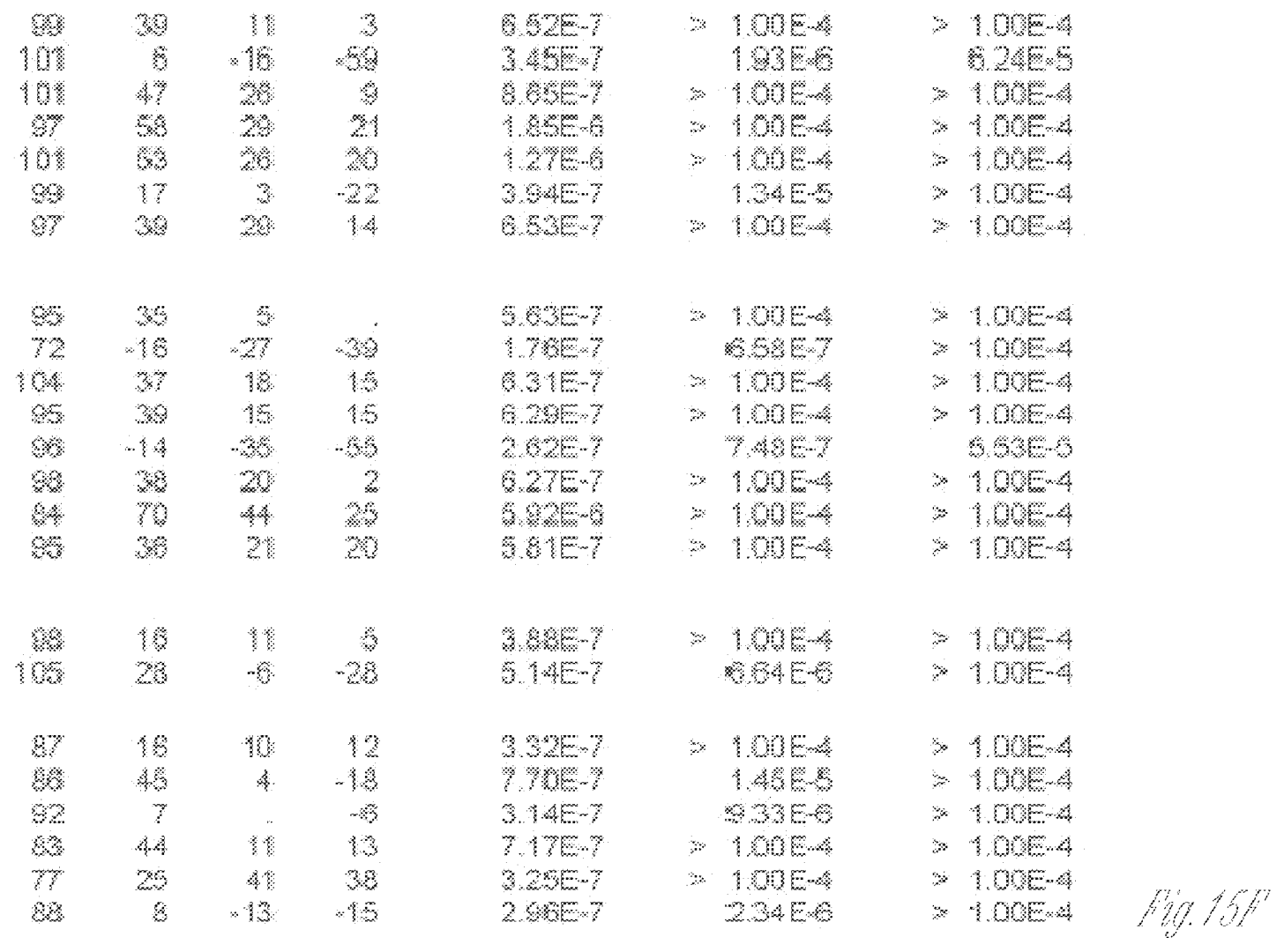

| | | | | | | |
|---|---|---|---|---|---|---|
| 99 | 39 | 11 | 3 | 6.52E-7 | > 1.00E-4 | > 1.00E-4 |
| 101 | 6 | -16 | -59 | 3.45E-7 | 1.93E-6 | 6.24E-5 |
| 101 | 47 | 28 | 9 | 8.65E-7 | > 1.00E-4 | > 1.00E-4 |
| 97 | 58 | 29 | 21 | 1.85E-6 | > 1.00E-4 | > 1.00E-4 |
| 101 | 63 | 26 | 20 | 1.27E-6 | > 1.00E-4 | > 1.00E-4 |
| 99 | 17 | 3 | -22 | 3.94E-7 | 1.34E-5 | > 1.00E-4 |
| 97 | 39 | 20 | 14 | 6.53E-7 | > 1.00E-4 | > 1.00E-4 |
| | | | | | | |
| 95 | 35 | 5 | | 5.63E-7 | > 1.00E-4 | > 1.00E-4 |
| 72 | -16 | -27 | -39 | 1.76E-7 | 6.58E-7 | > 1.00E-4 |
| 104 | 37 | 18 | 15 | 6.31E-7 | > 1.00E-4 | > 1.00E-4 |
| 95 | 39 | 15 | 15 | 6.29E-7 | > 1.00E-4 | > 1.00E-4 |
| 96 | -14 | -35 | -55 | 2.62E-7 | 7.49E-7 | 5.53E-5 |
| 98 | 38 | 20 | 2 | 6.27E-7 | > 1.00E-4 | > 1.00E-4 |
| 84 | 70 | 44 | 25 | 5.92E-6 | > 1.00E-4 | > 1.00E-4 |
| 85 | 36 | 21 | 20 | 5.81E-7 | > 1.00E-4 | > 1.00E-4 |
| | | | | | | |
| 98 | 16 | 11 | 5 | 3.88E-7 | > 1.00E-4 | > 1.00E-4 |
| 105 | 28 | -6 | -28 | 5.14E-7 | 6.64E-6 | > 1.00E-4 |
| | | | | | | |
| 87 | 16 | 10 | 12 | 3.32E-7 | > 1.00E-4 | > 1.00E-4 |
| 86 | 45 | 4 | -18 | 7.70E-7 | 1.45E-5 | > 1.00E-4 |
| 92 | 7 | | -6 | 3.14E-7 | 9.33E-6 | > 1.00E-4 |
| 83 | 44 | 11 | 13 | 7.17E-7 | > 1.00E-4 | > 1.00E-4 |
| 77 | 25 | 41 | 38 | 3.25E-7 | > 1.00E-4 | > 1.00E-4 |
| 88 | 8 | -13 | -15 | 2.96E-7 | 2.34E-6 | > 1.00E-4 |

Fig. 15F

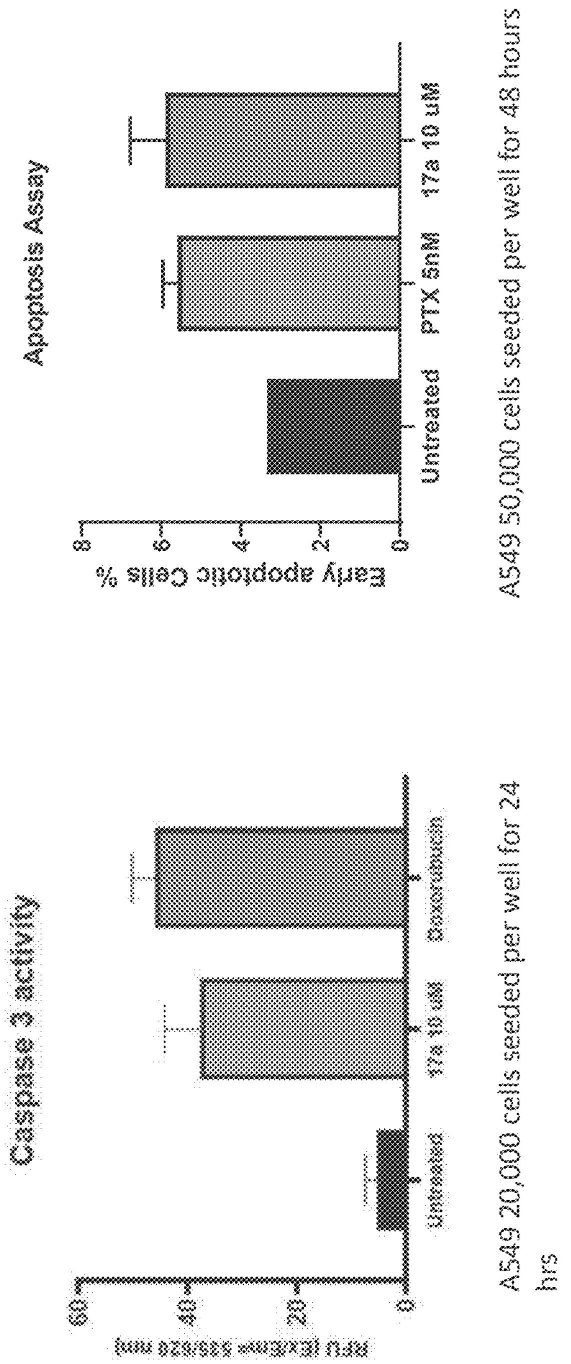
Figure 20. Detection of apoptosis in A549 cells treated with 17a at10 µM

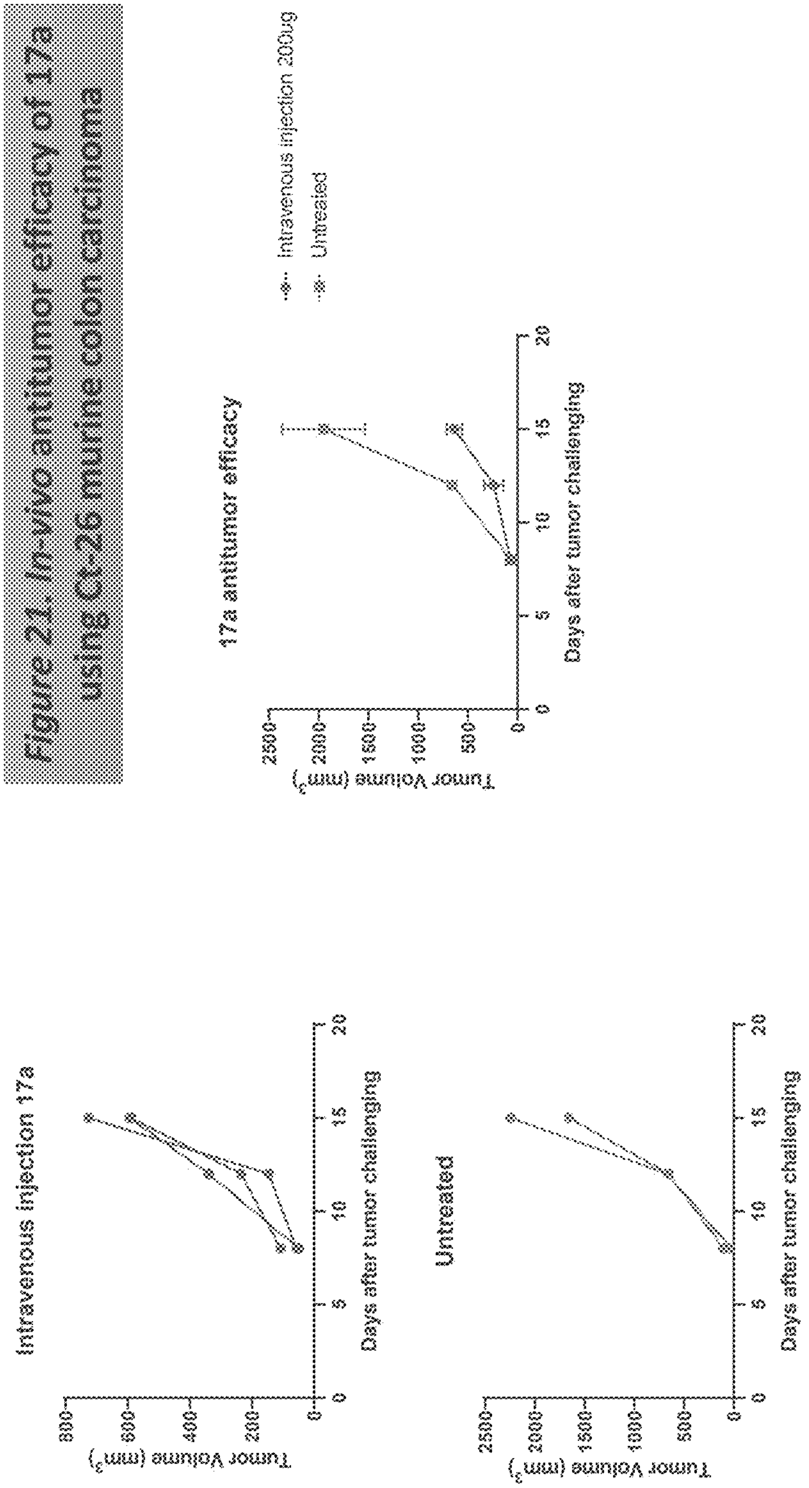
Figure 21. In-vivo antitumor efficacy of 17a using Ct-26 murine colon carcinoma

*Figure 22. In-vivo* antitumor efficacy of 17a using Ct-26 murine colon carcinoma
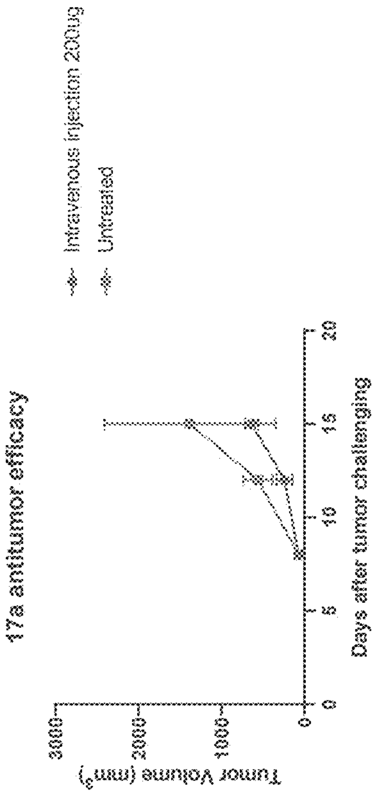
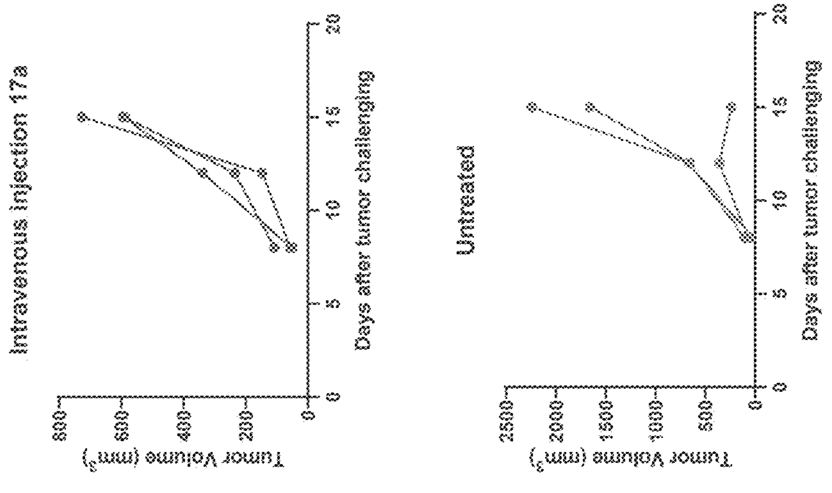

| PARTICLE DIAMETER (nm) | PDI | ZETA POTENTIAL (mV) |
|---|---|---|
| 173.5 | 0.127 | -40.1 |
| 172.4 | 0.087 | -38.2 |
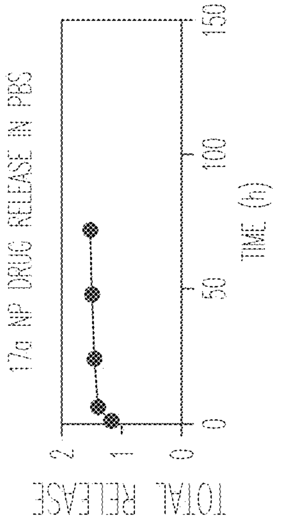
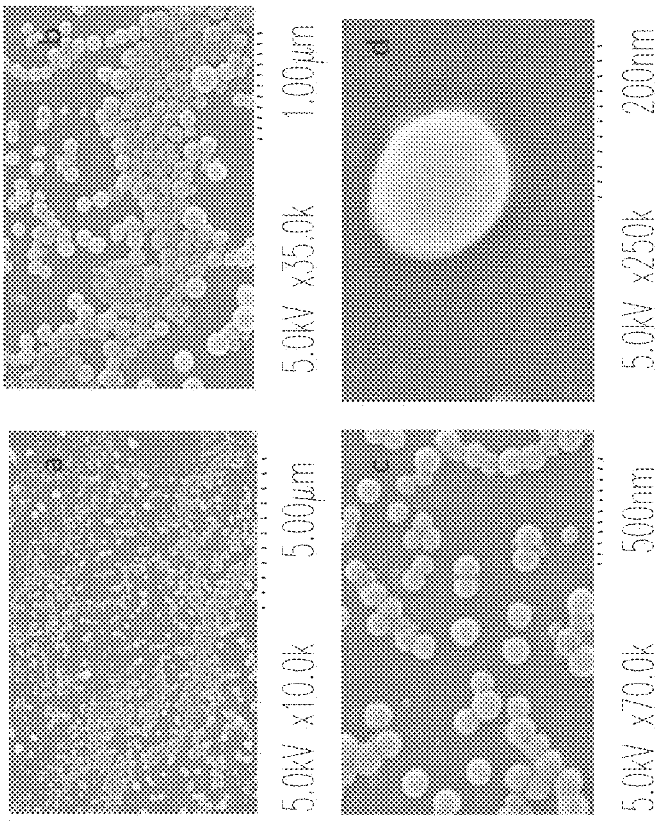
*Fig.23*

Cell viability testing of 17a (SA10)and its NP against CT-26 murine colon carcinoma (2000 cells/ well) 20 h log-dose vs response $IC_{50}$ Figure 25
| Cell viability testing for compound 11 SA10 (benzyl urea derivative) and its nanoparticle formulation using MTS assay B16F10 murine melanoma cell line (48 hours treatment) | | |
|---|---|---|
| Formulation or compound | Graph | $IC_{50}$ |
| SA10 NP F#2 (TPGS) | 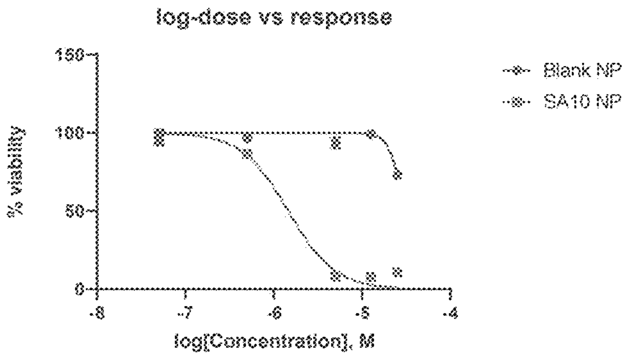 | 1.46 uM |
| Blank NP F#2 (TPGS) | | 30.46 uM |
| SA10 alone | 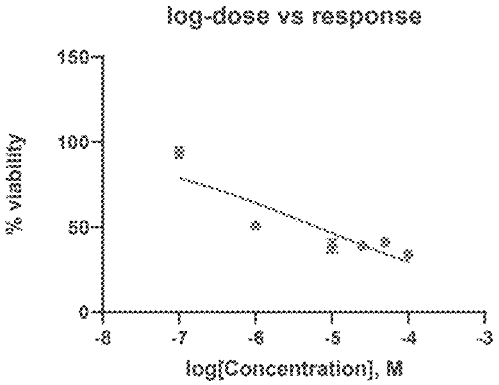 | 6.39 uM |

JNK INHIBITORS AS ANTICANCER AGENTS

CROSS-REFERENCE TO RELATED APPLICATIONS

This application is a U.S. National Stage Filing under 35 U.S.C. 371 from International Application No. PCT/US2020/039373, filed on Jun. 24, 2020, and published as WO 2020/263989 on Dec. 30, 2020, which application claims the benefit of the filing date of U.S. application No. 62/865,659, filed on Jun. 24, 2019, the disclosures of which are incorporated by reference herein.

BACKGROUND

Protein kinases, catalyzing the transfer of the terminal phosphate group of ATP to specific amino acid residues in target proteins, are the largest family of enzymes encoded by the human genome. The phosphorylation of the target protein results in modified activity, degradation, localization or association with other molecules. Among the mitogen-activated protein kinases (MAPKs) is the c-Jun N-terminal kinase (JNK) family that includes at least three proteins (JNK1, JNK2 and JNK3) that are encoded by three separate genes jnk1 (Mapk8), jnk2 (Mapk9) and jnk3 (Mapk10), and are alternatively spliced to create at least many variants. JNK1 and JNK2 are expressed in most tissues, while the expression of JNK3 is largely restricted to brain, heart and testes.

JNKs regulate many physiological processes, including inflammatory responses, morphogenesis, cell proliferation, differentiation, survival and death, and persistent activation of JNKs is involved in cancer development and progression. However, JNK1 and JNK2 may have distinct or even opposing functions in different types of cancer. Some JNK inhibitors have a lack of specificity and cellular toxicity, which is less than desirable for therapeutics.

SUMMARY

The disclosure provides a compound of formula (I):

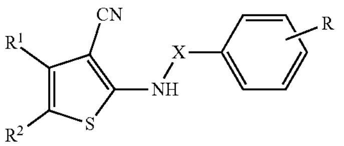

wherein R is hydrogen, halo, alkyl, alkenyl, alkynyl, alkoxy, haloalkyl, or substituted alkyl, alkenyl or alkynyl, or a carbocycle or heterocycle; wherein X comprises an alkyl, carbonyl, or amide; and wherein $R^1$ and $R^2$ independently are alkyl, alkenyl, alkynyl, alkoxy, or substituted alkyl or $R^1$ and $R^2$ together form a C6 or C7 ring; or a pharmaceutically acceptable salt thereof. In one embodiment, R is hydrogen, halo, (C1-C6)alkyl, or substituted (C1-C6)alkyl. In one embodiment, halo is Br, F or I. In one embodiment, R is a carbocycle, e.g., an aryl such as a C5, C6, C7, or C8 aryl. In one embodiment, R is a substituted carbocycle. In one embodiment, R is not benzyl. In one embodiment, R is not hydrogen. In one embodiment, X is (C1-C6)alkyl, CONH or CONH(C1-C6)alkyl. In one embodiment, X is substituted (C1-C6)alkyl, or substituted CONH(C1-C6)alkyl. In one embodiment, X has a chain length of no more than 6 atoms. In one embodiment, R1 and R2 together form a C7 ring. In one embodiment, R1 and R2 together form a C6 ring. In one embodiment, R1 and R2 together form an aryl ring. In one embodiment, the compound is is a benzamide. In one embodiment, the compound is a benzylamine. In one embodiment, the compound comprises urea. In one embodiment, the compound is a fused thiophene. In one embodiment, the compound inhibits JNK2 and/or JNK3. In one embodiment, the compound is not N-(3-cyano-4,5,6,7-tetrahydro-1-benzothien-2-yl)1-naphthamide. In one embodiment, the X is not COCONHNCC=C($C_6H_5$). Also provided is a composition having the compound. In one embodiment, the composition comprises nanoparticles having the compound. In one embodiment, the nanoparticles have a diameter from about 100 nm to about 250 nm. In one embodiment, the nanoparticles are formed of a synthetic polymer, e.g., lactic acid, glycolic acid, caproic acid, a polyanhydride, or a combination thereof.

N-(3-cyano-4,5,6,7-tetrahydro-1-benzothien-2-yl)1-naphthamide was found to be a potent JNK inhibitor with $pIC_{50}$ values of 6.5 and 6.7 for JNK2 and JNK3, respectively. As disclosed herein, certain fused thiophenes, e.g., having formula (I) or (II), including those that inhibit one or more distinct JNKs, have anti-cancer activity. In one embodiment, a series of 3-cyano-4,5,6,7-tetrahydro-1-benzothiophene with 2-benzamides, 2-benzylamines or 2-urea moieties were designed as potential anticancer agents through inhibition of JNKs. In vitro anticancer screening using a MTS assay against A549 cell line showed that an exemplary benzyl urea (1), 3-bromobenzamide (2) and 4-bromobenzylamine (3) were the most active members among the ureas, benzamides and benzylamines, with $IC_{50}$ values of 1.6, 7.6 and 2.7 μM, respectively. The inhibitory activity of the synthesized compounds against JNK2 and JNK3 was determined. The selective JNK inhibitors disclosed herein are useful as anticancer agents.

(1)

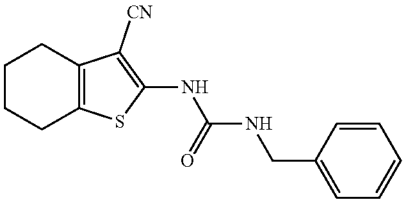

$IC_{50}$ =1.6 uM (2)

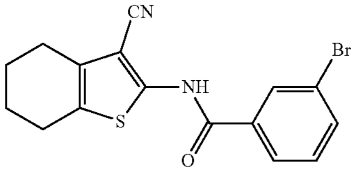

$IC_{50}$ =7.6 uM (3)

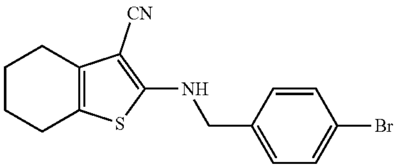

$IC_{50}$ =2.7 uM

In one embodiment, the disclosure provides for a compound of formula (I):

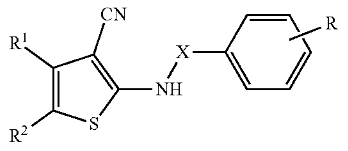

wherein X≡CO; $CH_2$; CONH; or $CONHCH_2$;

wherein R=2-I; 2-Br; 3-Br; 4-Br; 2-F; $C_{10}H_7$; $C_6H_5$; $2\text{-}BrC_6H_4$; $4\text{-}CH_3C_6H_4$; $4\text{-}OCH_3C_6H_4$; $4\text{-n-}C_4H_9C_6H_4$; or $C_6H_5CH_2$. In one embodiment, X comprises alkyl, carbonyl or an amide. In one embodiment, X is CO, $CH_2CONH$ or $CONHCH_2$. In one embodiment, R is halo, hydrogen, alkyl, e.g., C1-C10 alkyl, alkenyl, substituted alkyl or substituted alkenyl. In one embodiment, $R^1$ and $R^2$ together form a C6 or C7 ring. In one embodiment, $R^1$ and $R^2$ together form an aryl ring. In one embodiment, $R^1$ and $R^2$ together form a heterocyclic ring.

In one embodiment, the disclosure provides for a compound of formula (II) which is a fused thiophene:

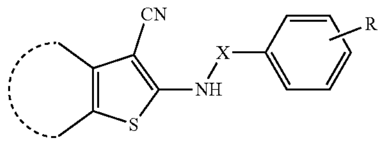

In one embodiment, X comprises a carbonyl or an amide. In one embodiment, X comprises one carbonyl group. In one embodiment, X is CO, $CH_2CONH$ or $CONHCH_2$. In one embodiment, R is halo, hydrogen, alkyl, e.g., C1-C10 alkyl, alkenyl, substituted alkyl, substituted alkenyl, or a C6 carbocycle that is optionally substituted.

Also provided is a method to prevent, inhibit or treat cancer in a mammal, comprising administering to the mammal a composition having an effective amount of the compound, e.g., a fused thiophene. In one embodiment, the amount of effective to inhibit cancer. In one embodiment, the mammal is a human. In one embodiment, the compound comprises a benzamide. In one embodiment, the compound comprises a benzylamine. In one embodiment, the compound comprises urea. In one embodiment, the composition is intravenously administered. In one embodiment, the composition is locally administered. In one embodiment, the composition is injected. In one embodiment, the composition is orally administered. In one embodiment, the composition comprises nanoparticles or microparticles. In one embodiment, the particles are formed of a synthetic polymer. In one embodiment, the particles comprise lactic acid, glycolic acid, caproic acid, a polyanhydride, or a combination thereof. In one embodiment, the particles comprise lactic acid and glycolic acid, polycaprolactone or poly lactic acid. In one embodiment, the particles comprise PEI. In one embodiment, the particles are formed of a natural polymer. In one embodiment, the particles are formed of collagen, proteoglycan, alginate, chitosan or extracellular matrix. In one embodiment, the particles are formed of polystyrene. In one embodiment, the particles comprise N-(3-cyano-4,5,6,7-tetrahydro-1-benzothien-2-yl)1-naphthamide. In one embodiment, the cancer is melanoma, ovarian cancer or renal cancer. In one embodiment, the cancer is leukemia, lung cancer or colon cancer. In one embodiment, the compound inhibits JNK2 and/or JNK3.

BRIEF DESCRIPTION OF THE FIGURES

FIG. 3. Screening results for compound 4a.

FIG. 4. Screening results for compound 6a.

FIG. 5. Screening results for compound 6b.

FIG. 6. Screening results for compound 9a.

FIG. 7. Screening results for compound 13b.

FIG. 8. Screening results for compound 17a.

FIG. 9. $GI_{50}$ values.

FIG. 12. Screening results for compound 17a.

FIG. 13. $GI_{50}$ values.

FIG. 20. Detection of apoptosis in A549 cells treated with compound 17a at 10 μM.

FIG. 21. In vivo antitumor efficacy of compound 17a using Ct-26 murine colon carcinoma.

FIG. 22. In vivo antitumor efficacy of compound 17a using Ct-26 murine colon carcinoma.

FIG. 23. 17a nanoparticle (NP) formulation using PLGA RG 502 $H^+$.

FIG. 24. Cell viability testing using compound 17a.

FIG. 25. Cell viability testing for compound 11 SA10 (benzyl urea derivative) and its nanoparticle formulation using MTS assay B16F10 murine melanoma cell line (48 hours treatment).

DETAILED DESCRIPTION

Definitions

Figure 1:
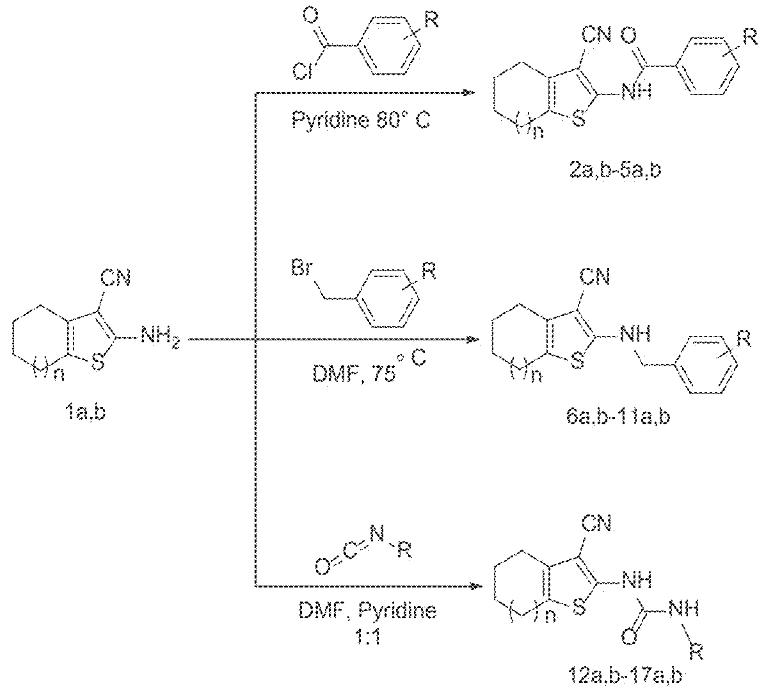
FIG. 1. Synthesis of benzamides 2a,b-5a,b, benzylamines 6a,b-11a,b and ureas 12a,b-17a,b.
Figure 2:
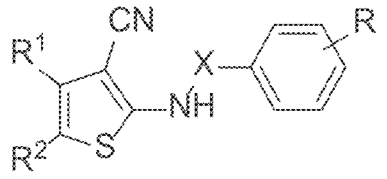
FIG. 2. Exemplary structures and exemplary substituents in Formula (I).
Figure 10A:
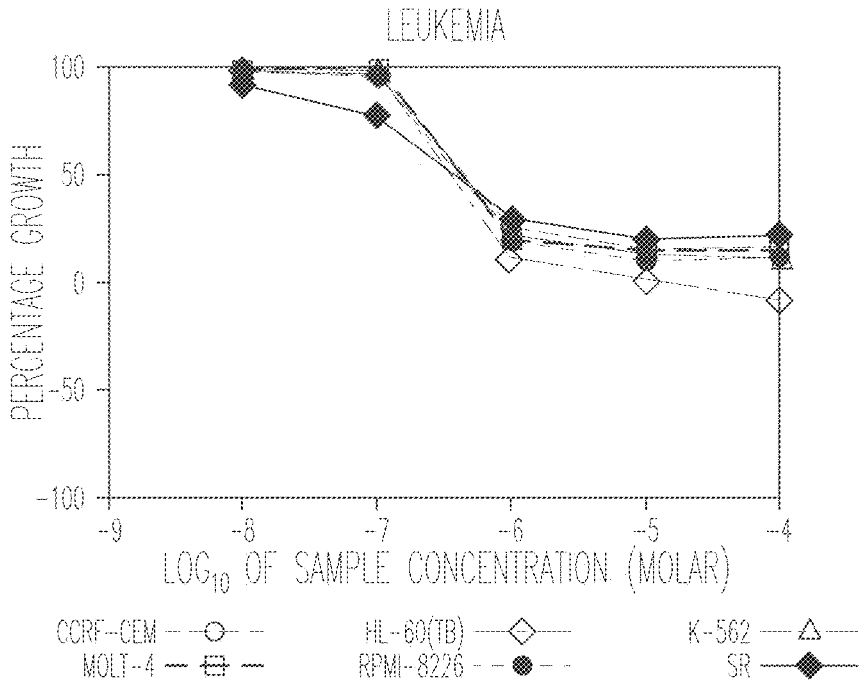
FIG. 10. Dose response curves.
Figure 10B:
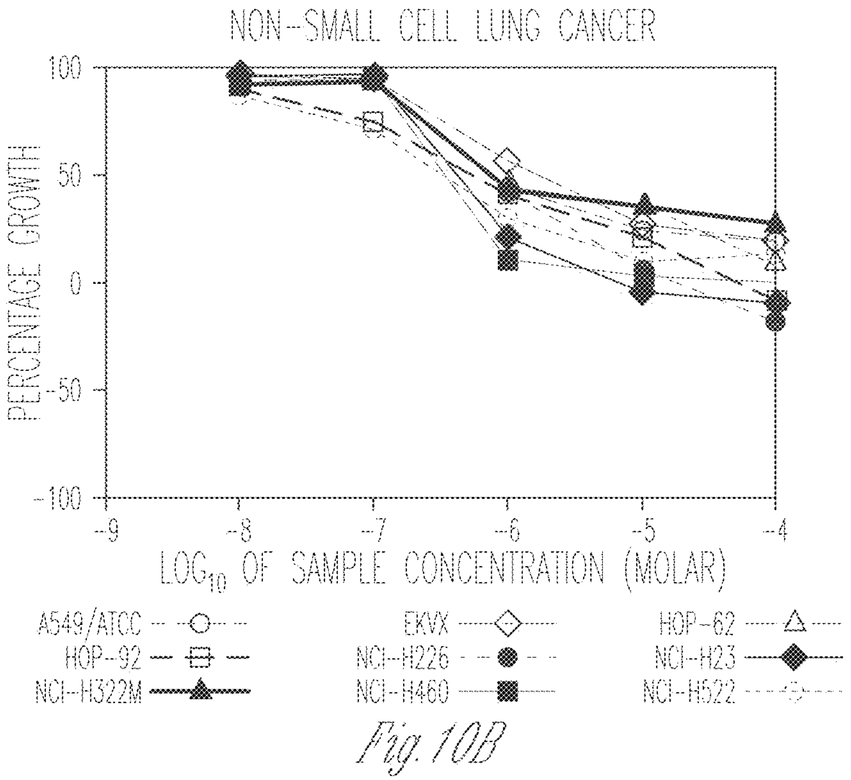
Figure 10C:
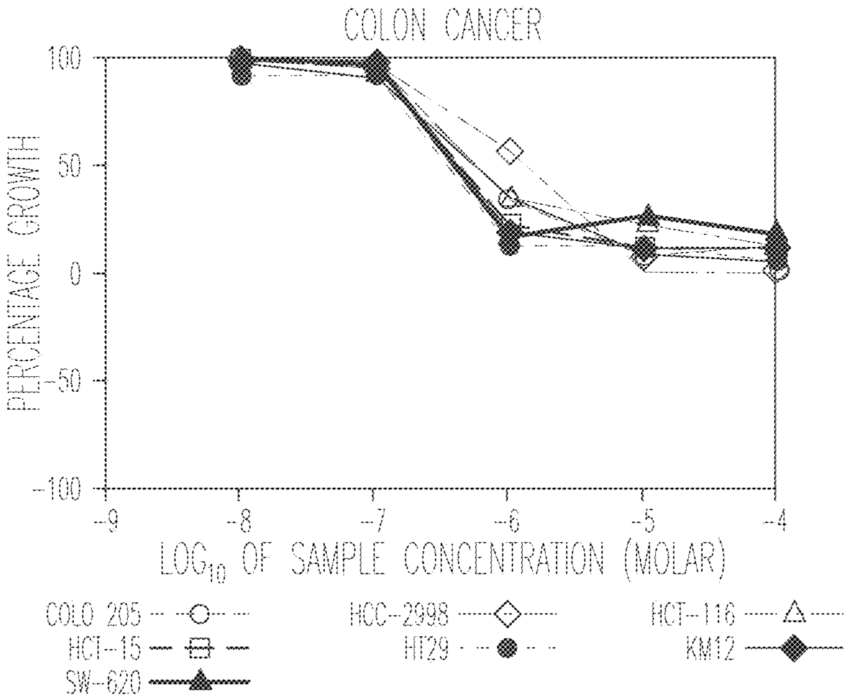
Figure 10D:
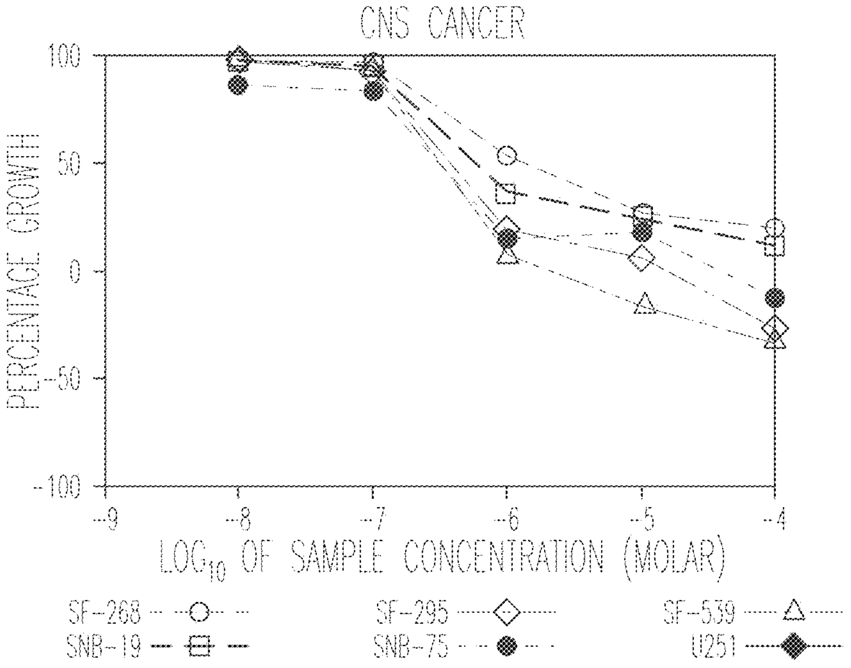
Figure 10E:
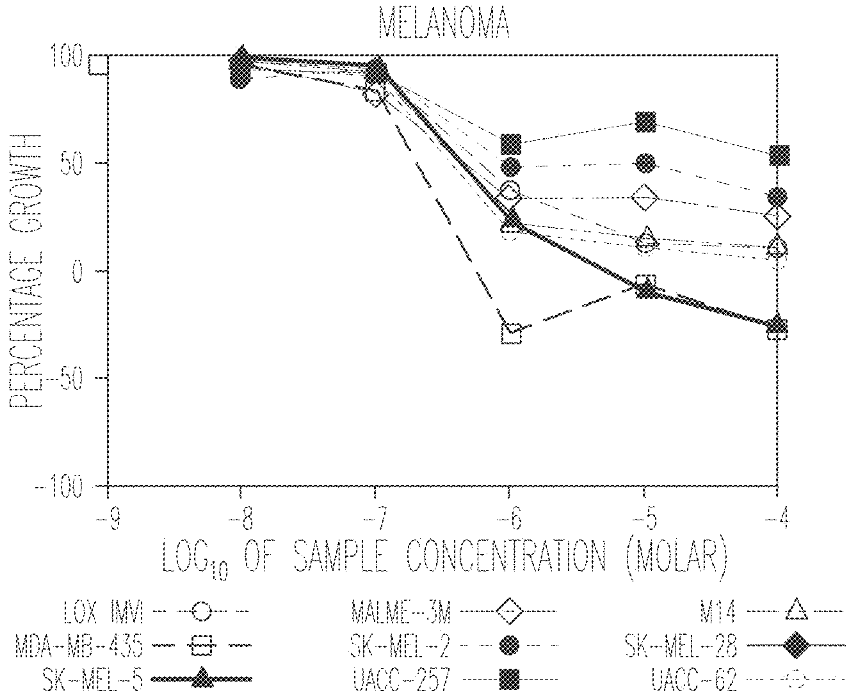
Figure 10F:
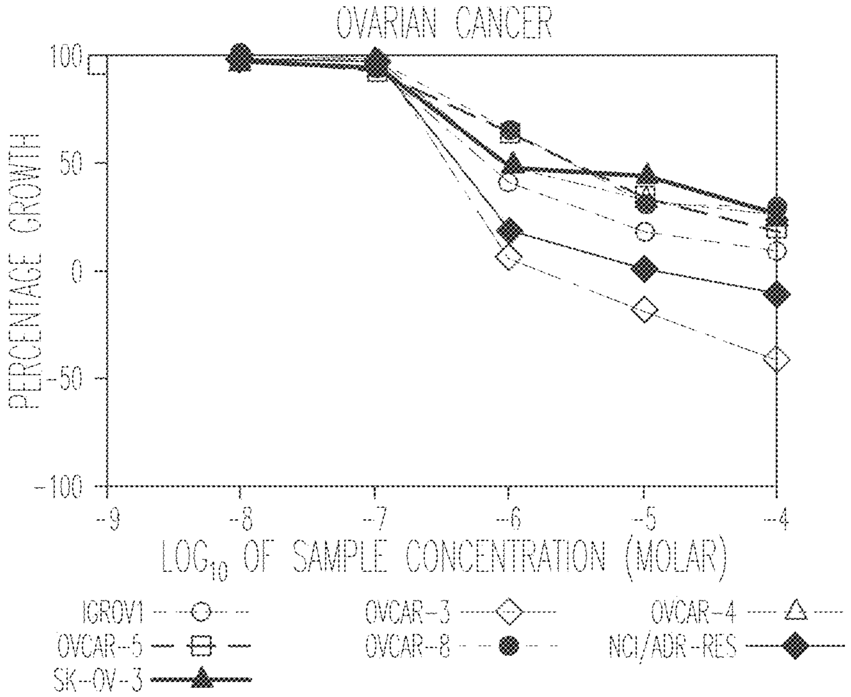
Figure 10G:
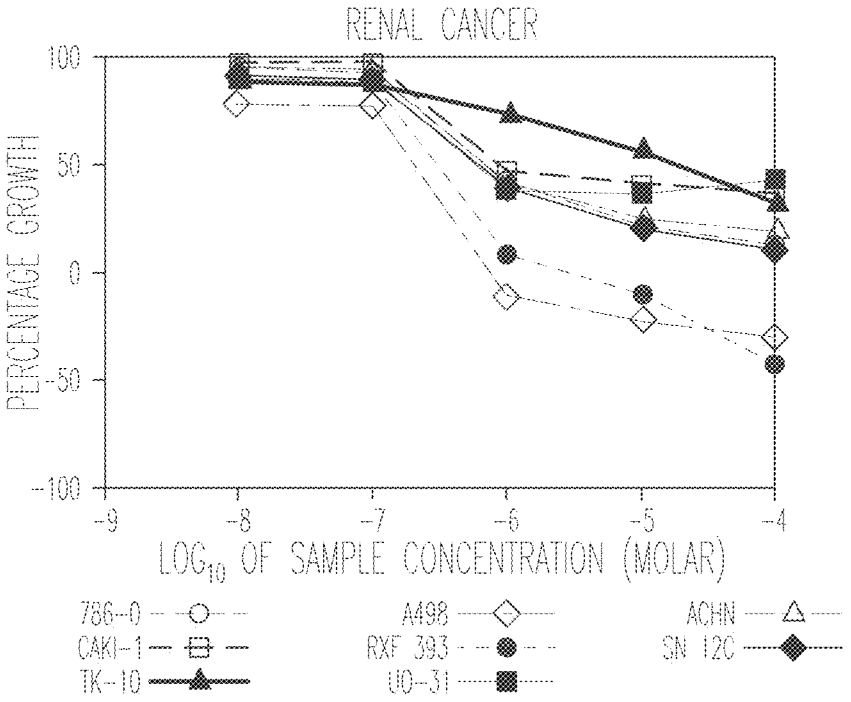
Figure 10H:
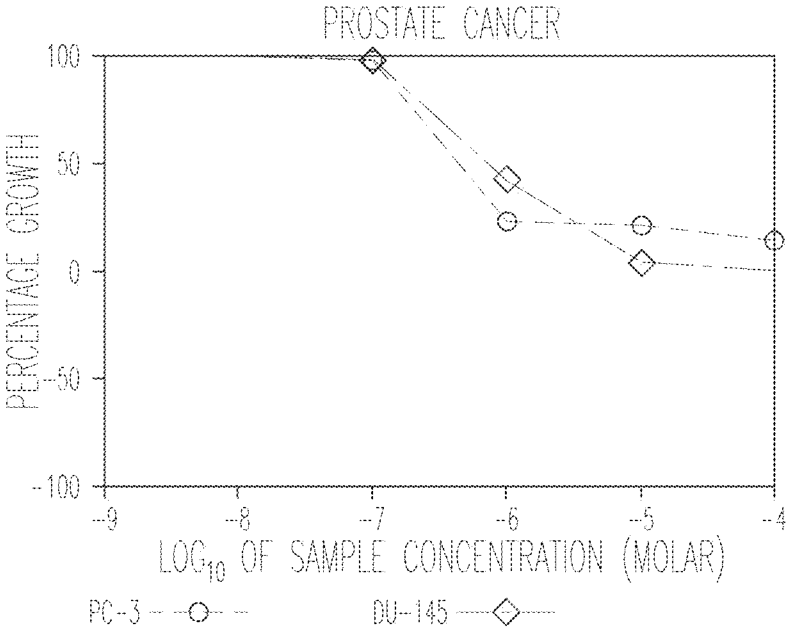
Figure 10I:
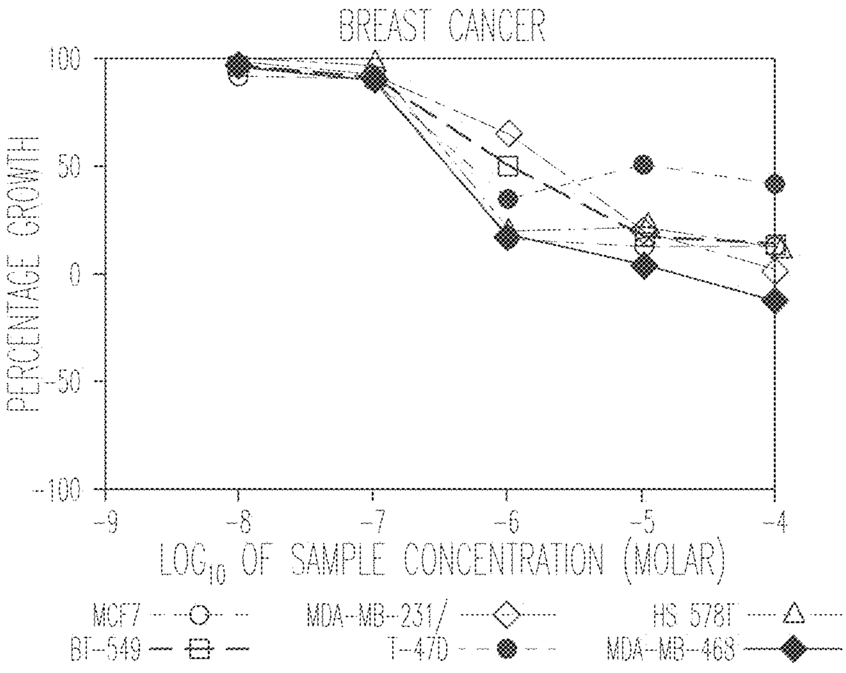
Figure 10J:
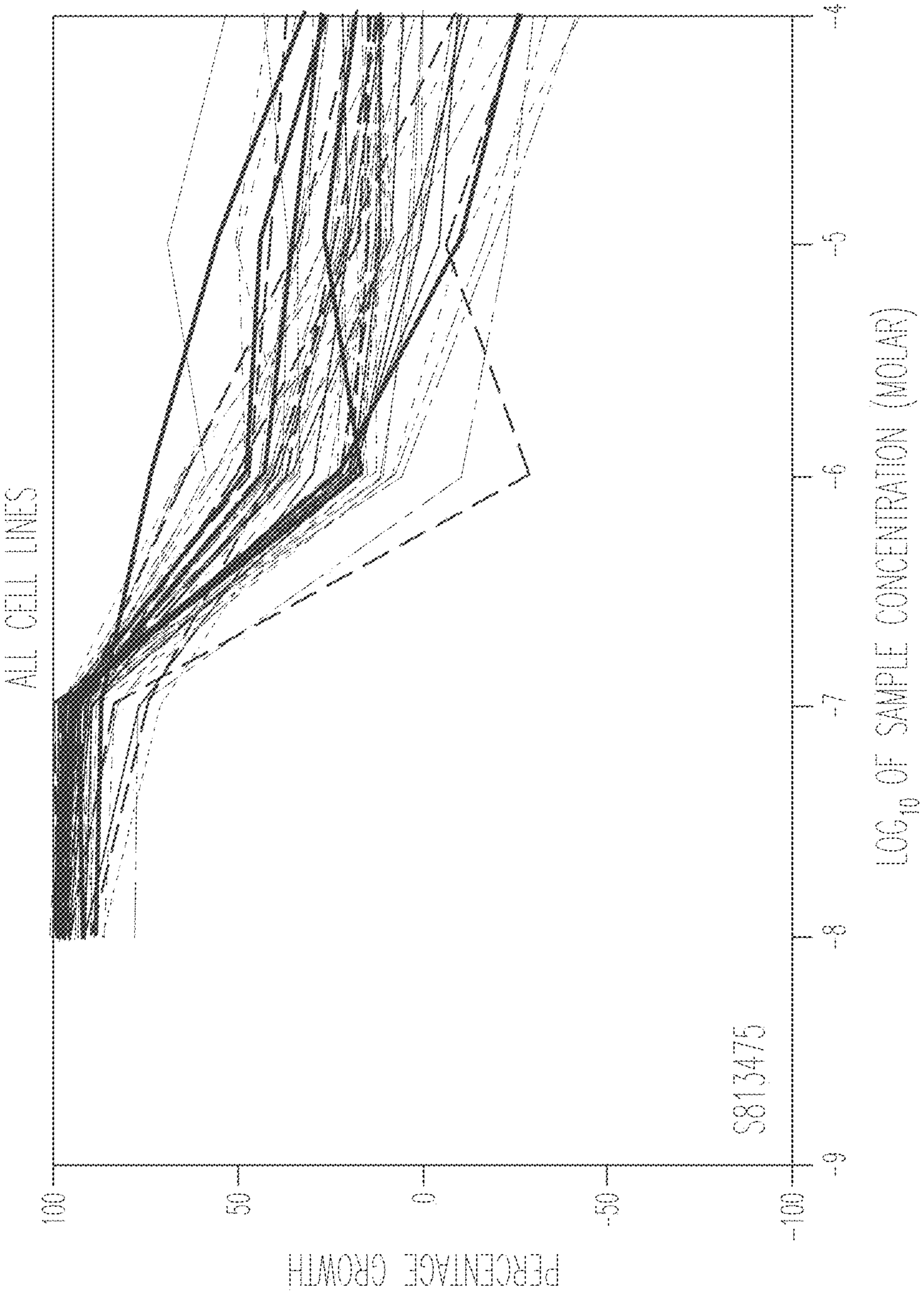
Figure 11:
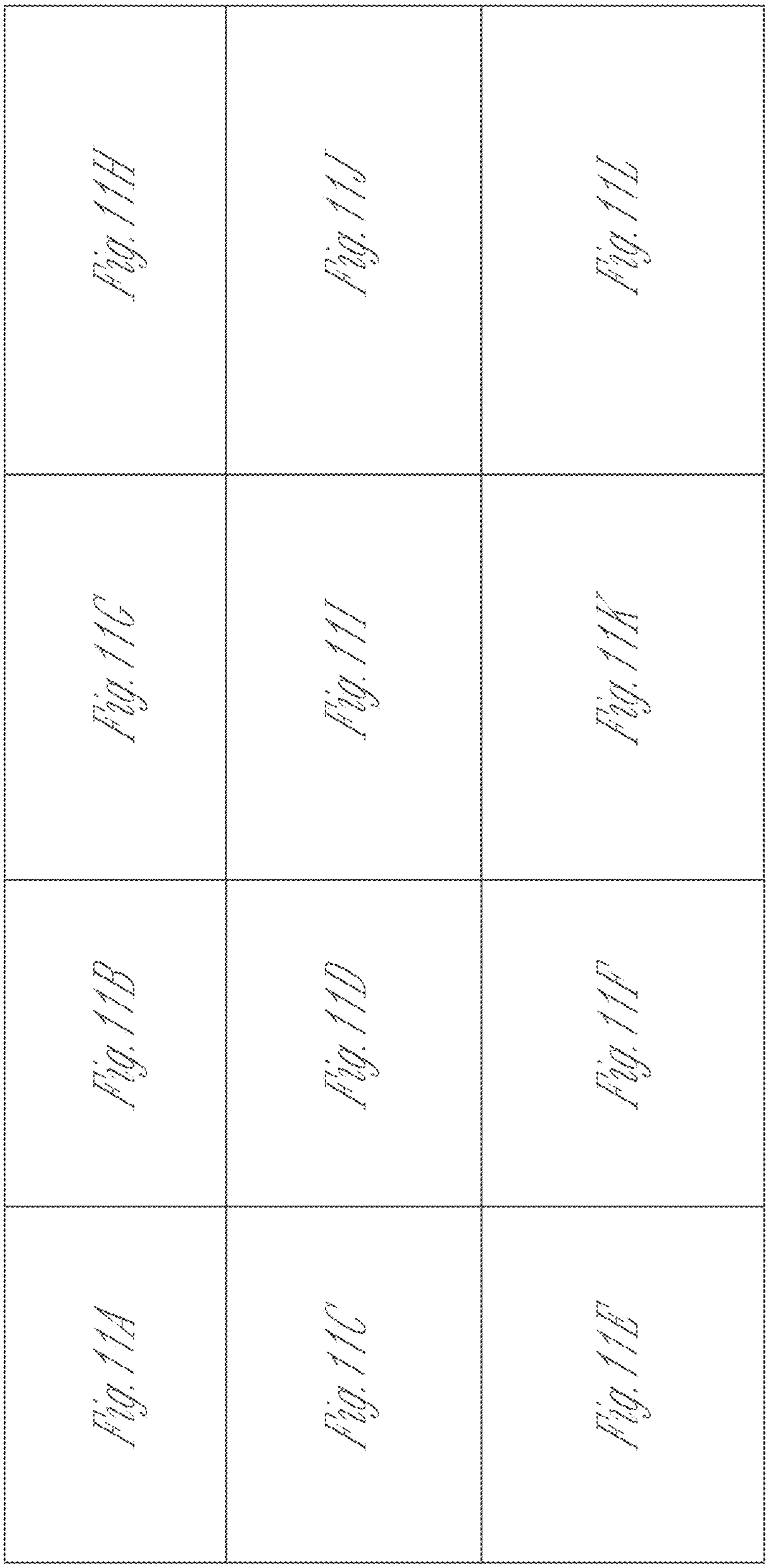
FIG. 11. In vitro testing results.
Figure 11C:
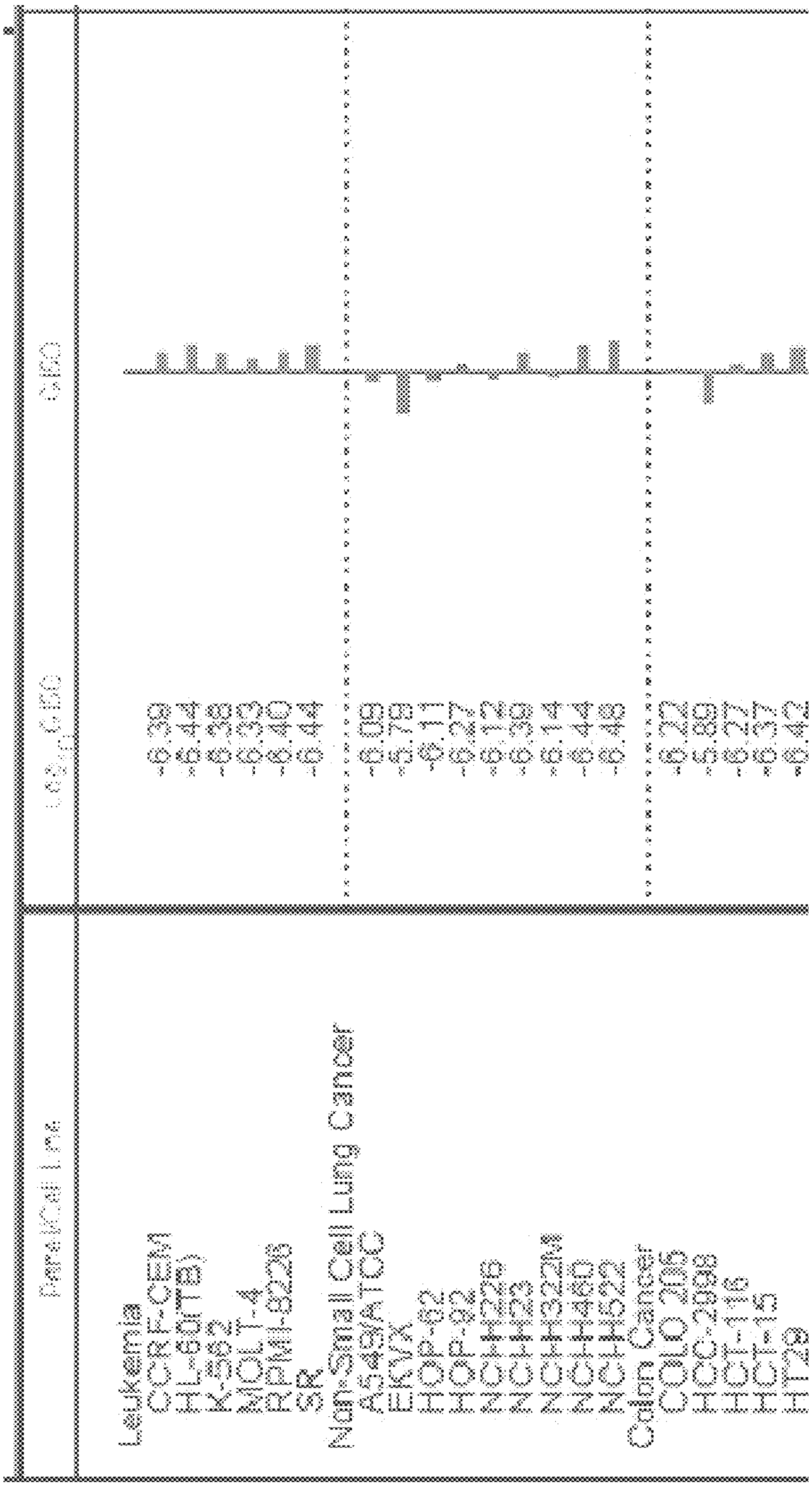
Figure 11H:
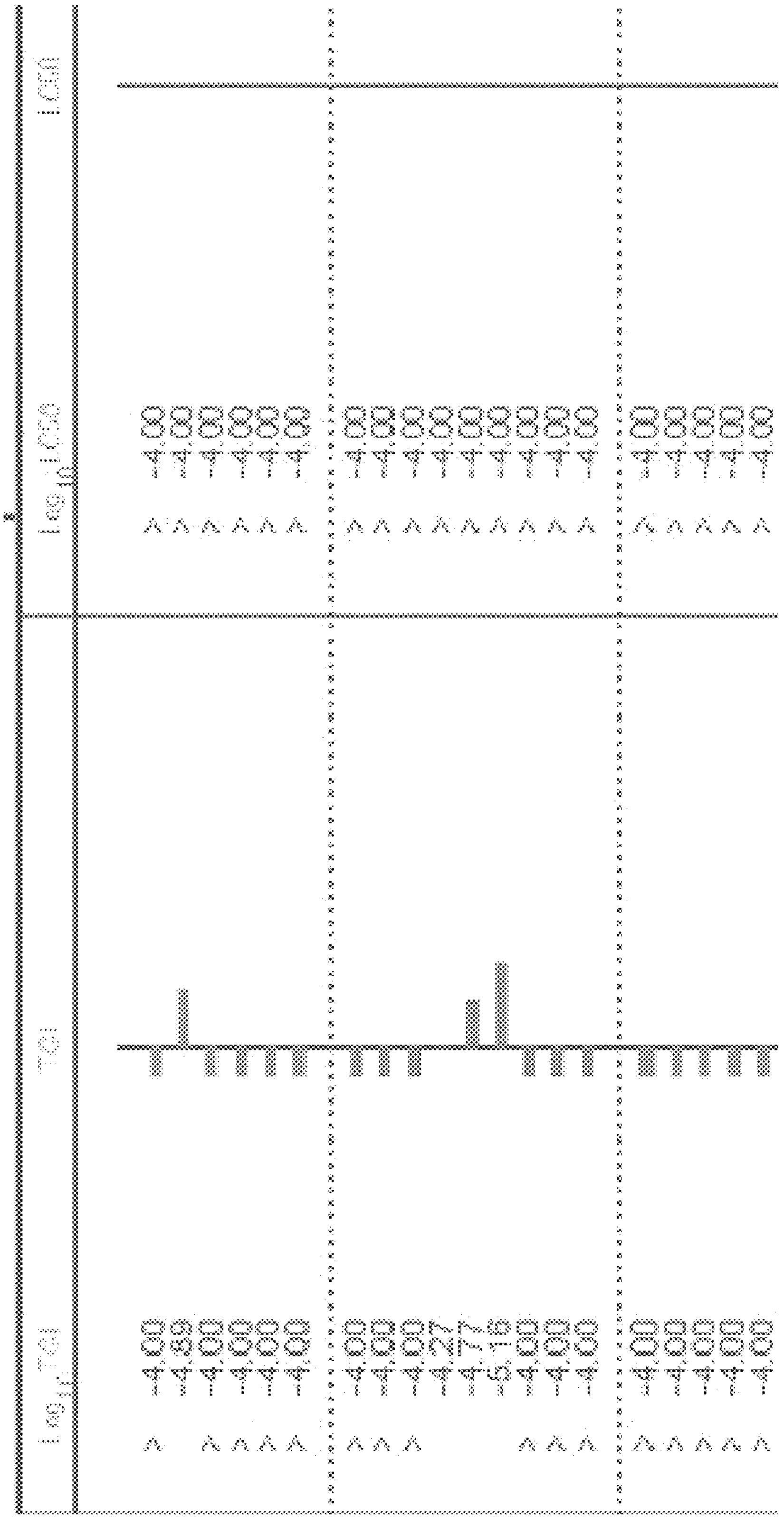
Figure 11I:
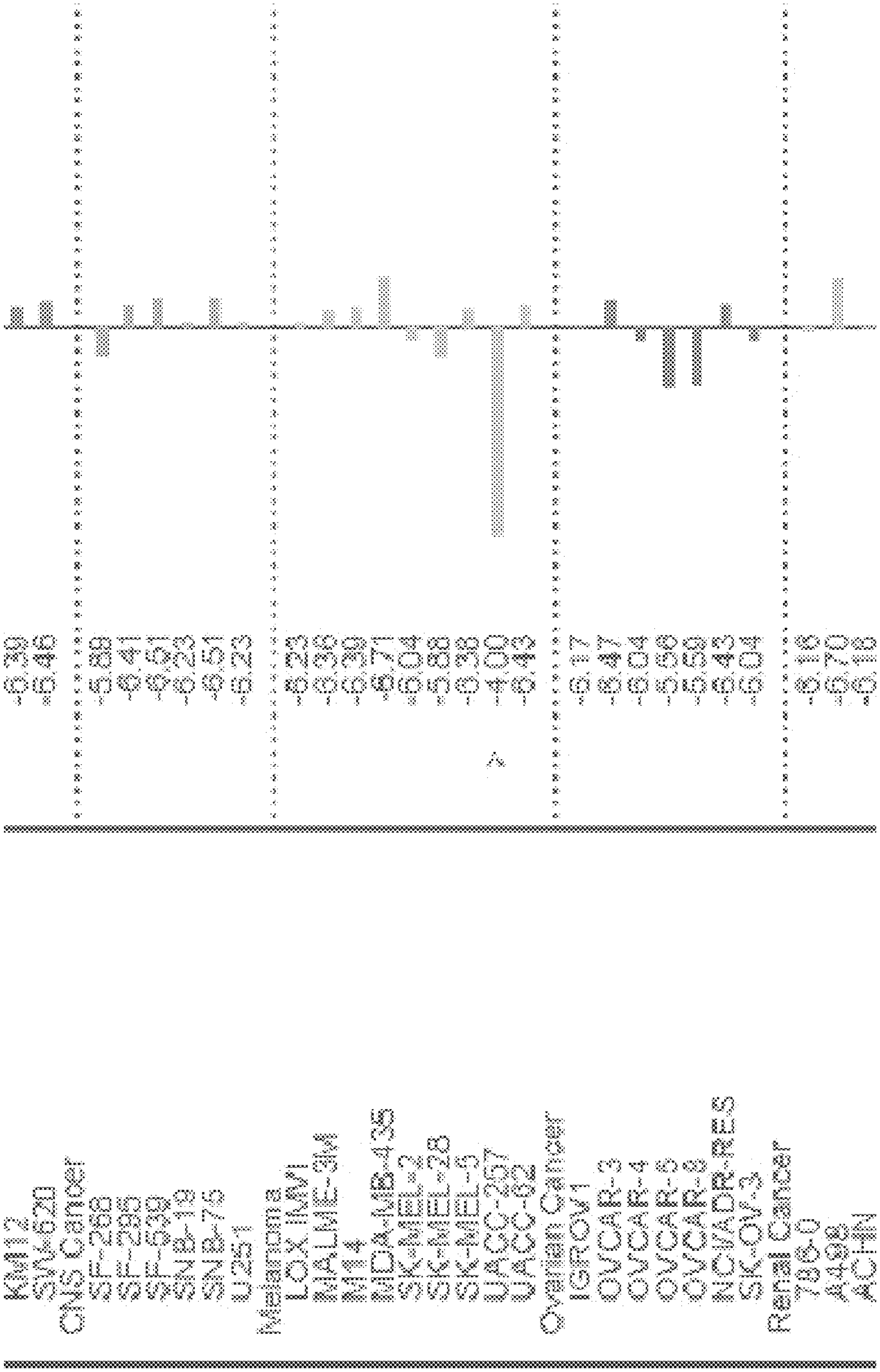
Figure 11J:
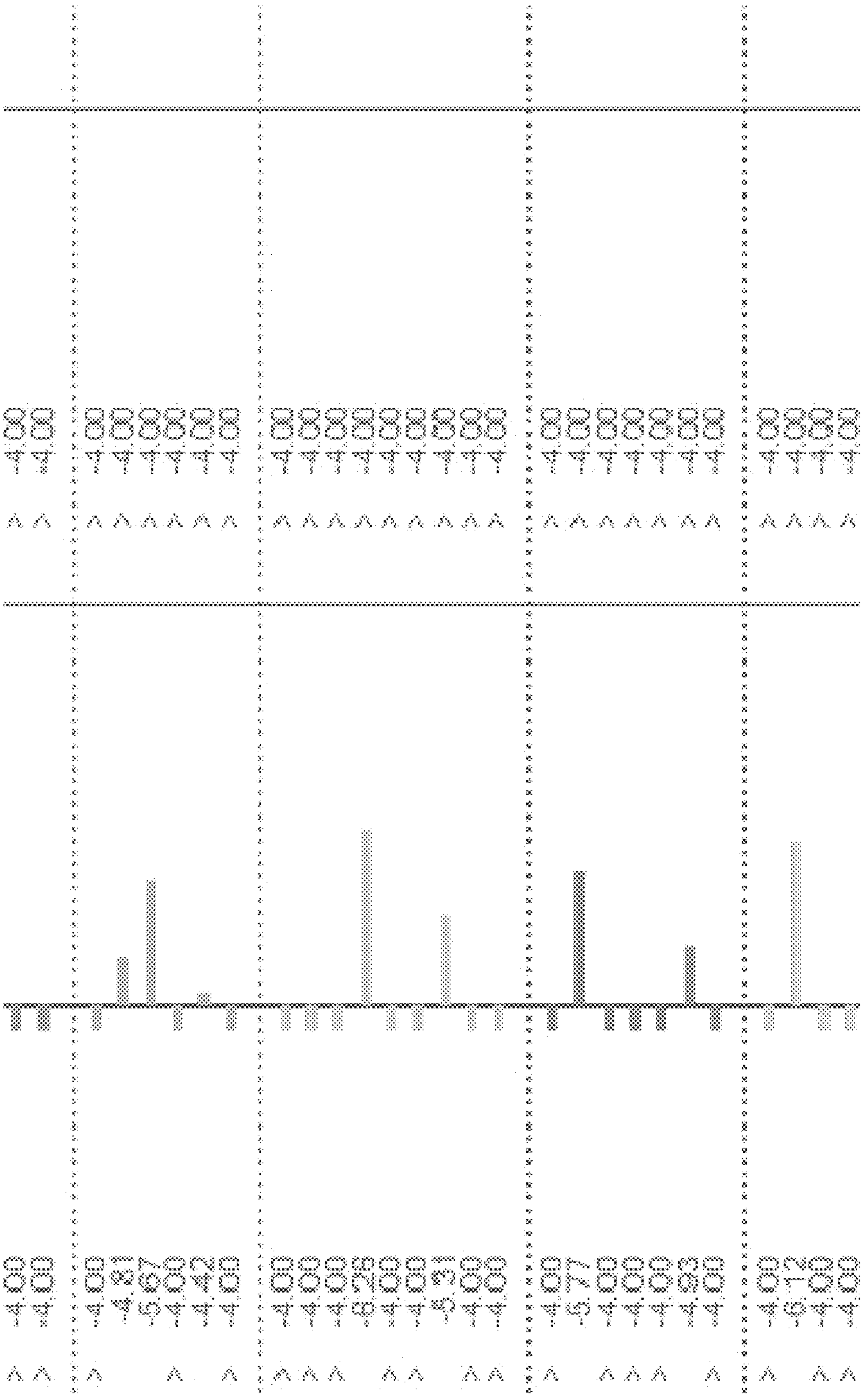
Figure 11K:
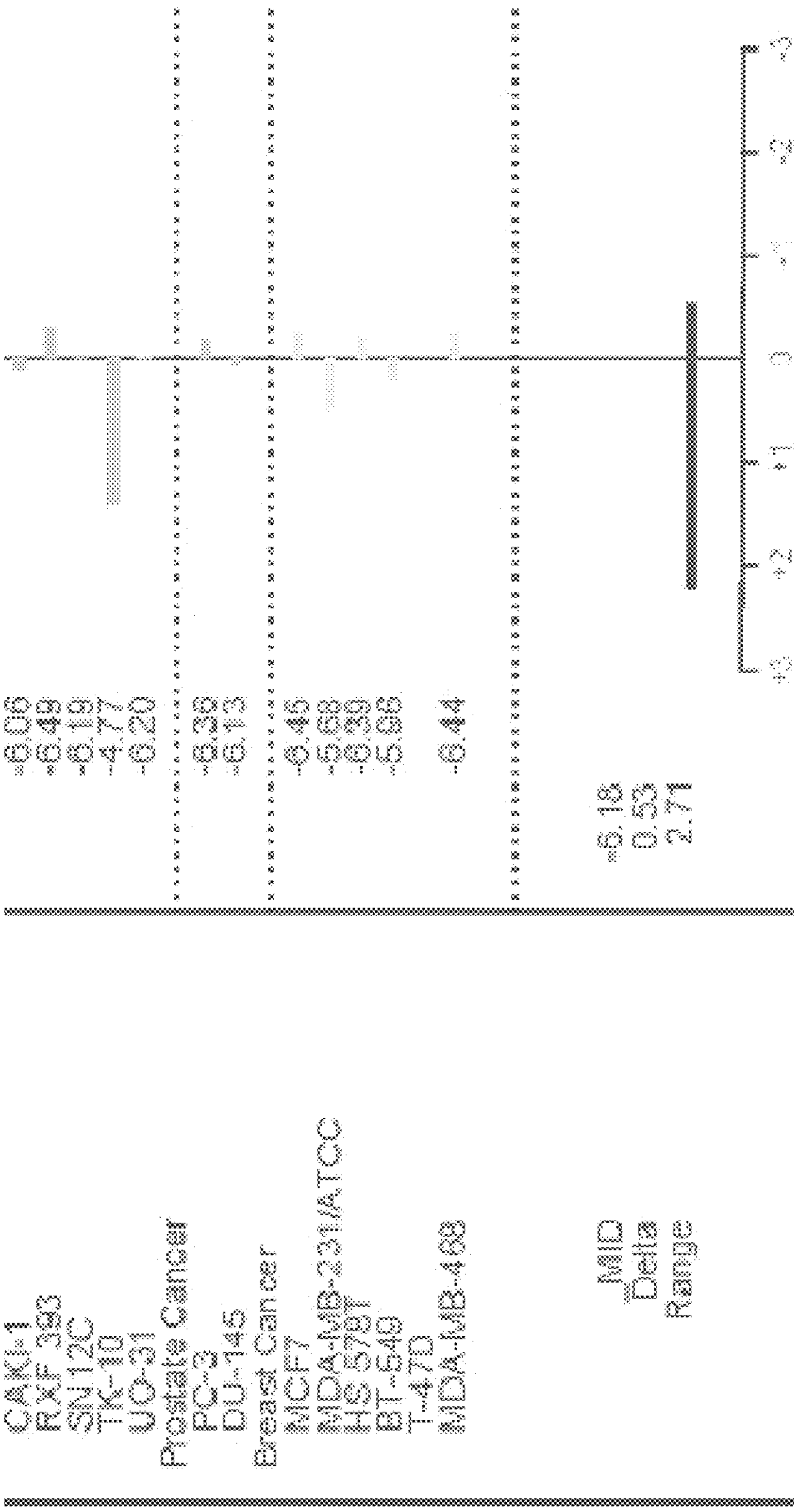
Figure 11L:
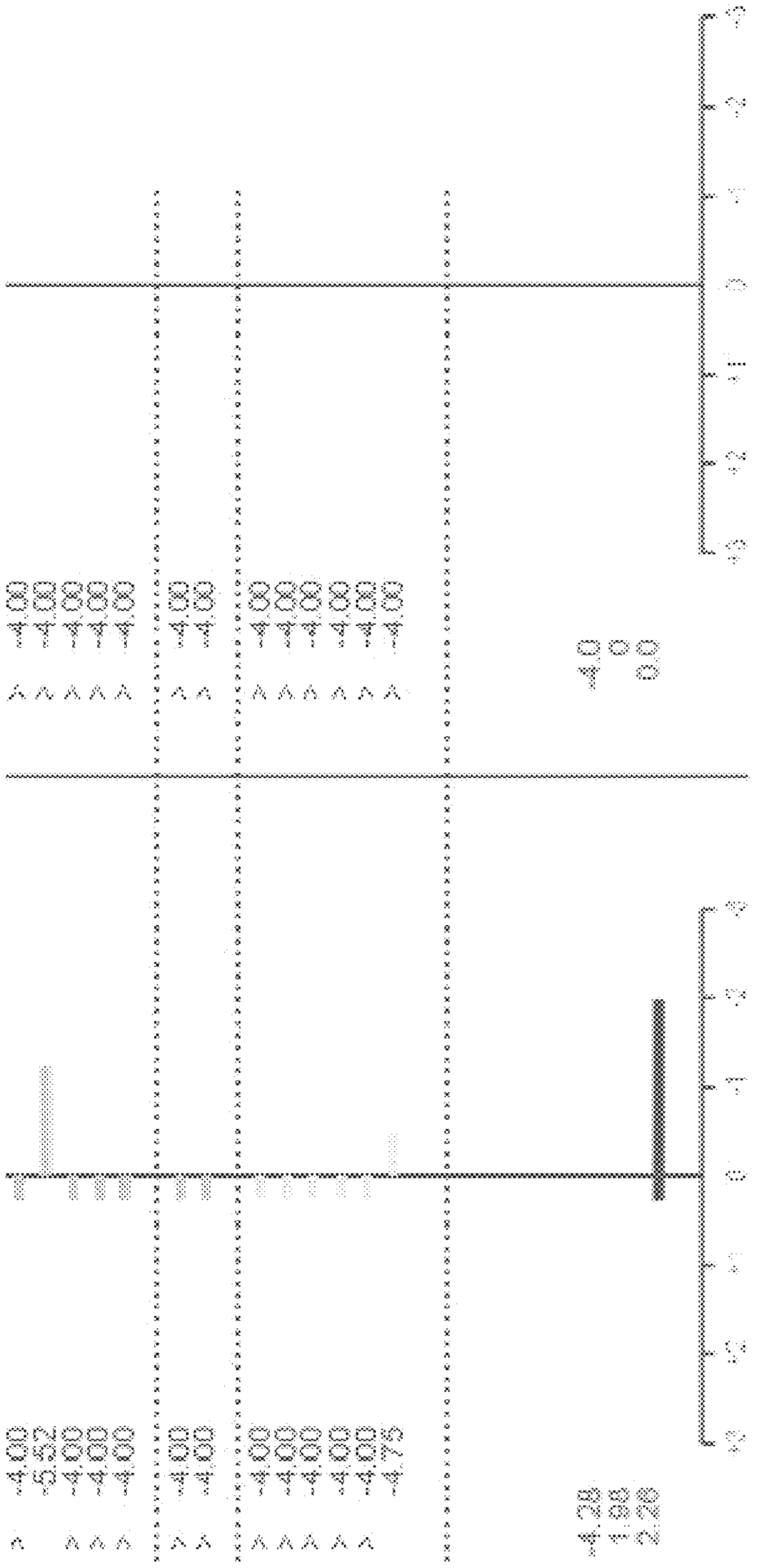
Figure 12:
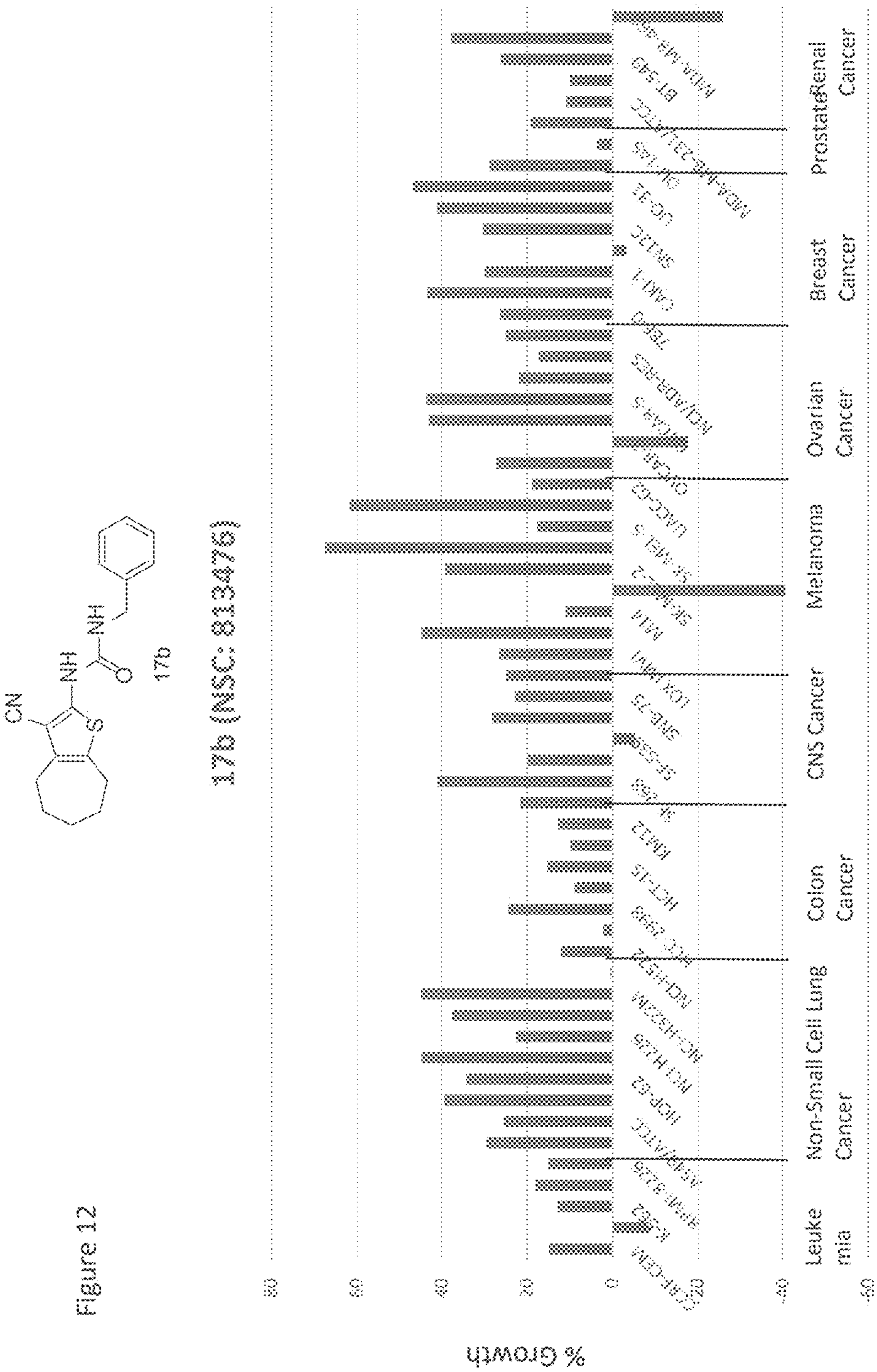
Figure 14A:
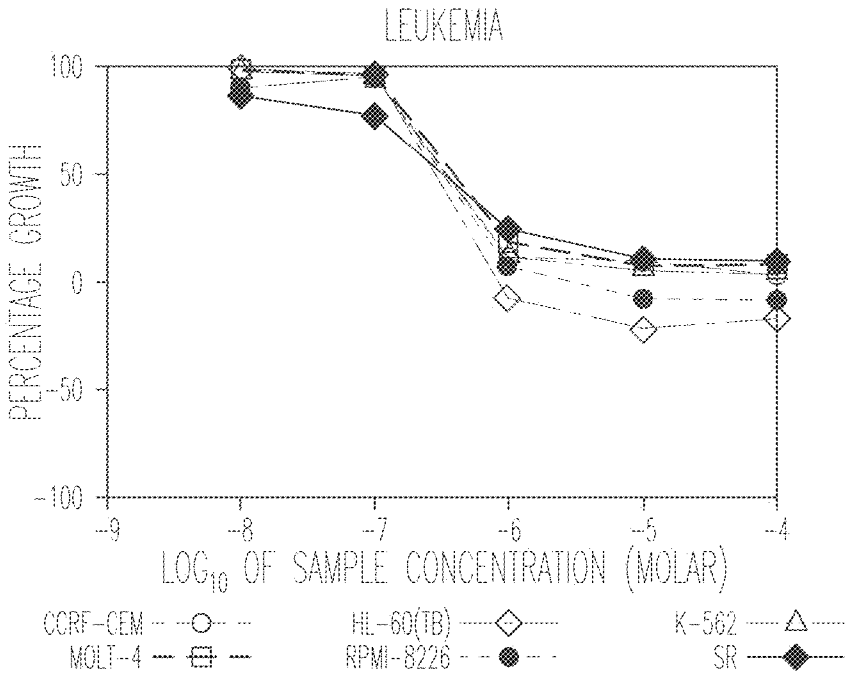
FIG. 14. Dose response curves.
Figure 14B:
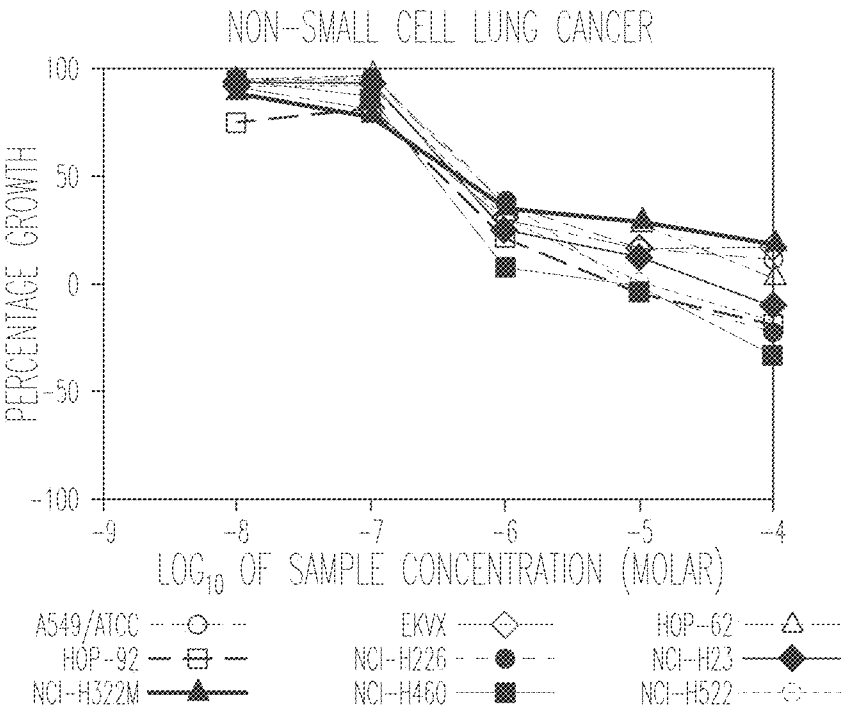
Figure 14C:
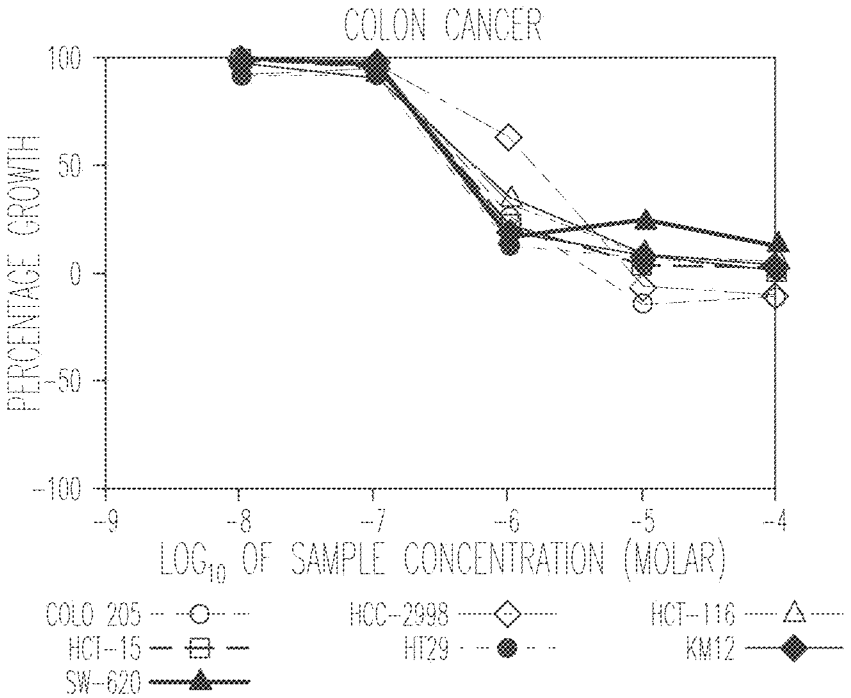
Figure 14D:
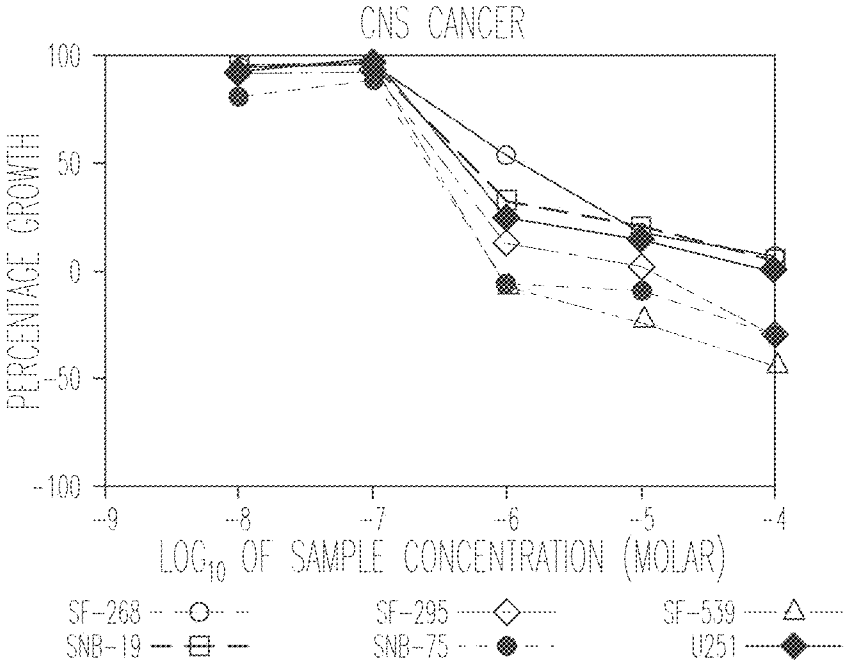
Figure 14E:
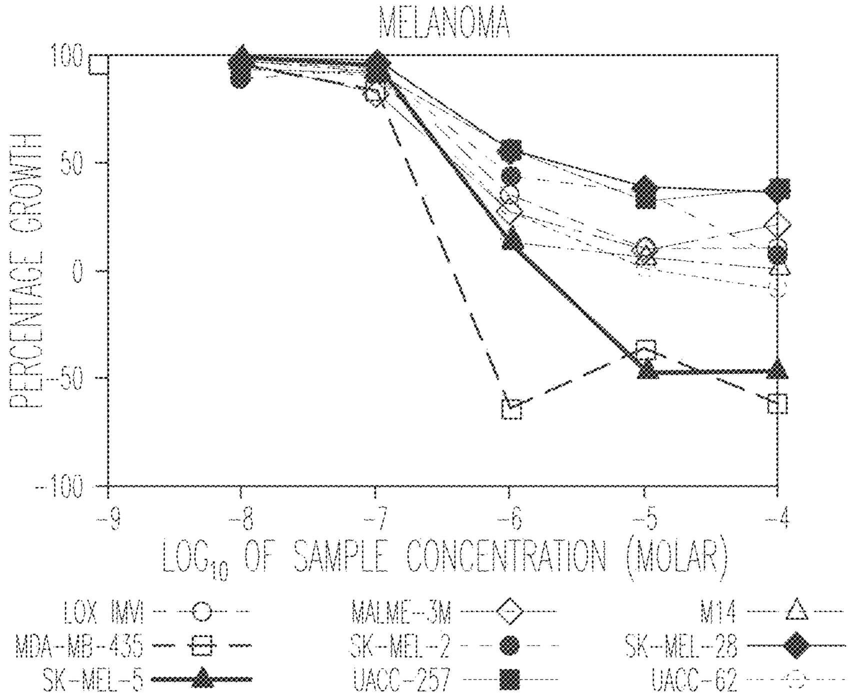
Figure 14F:
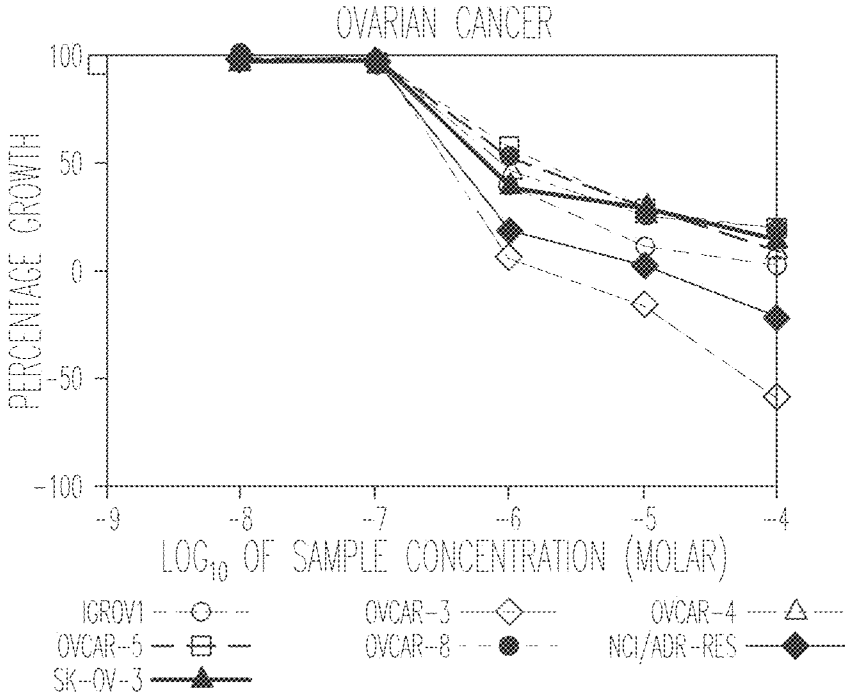
Figure 14G:
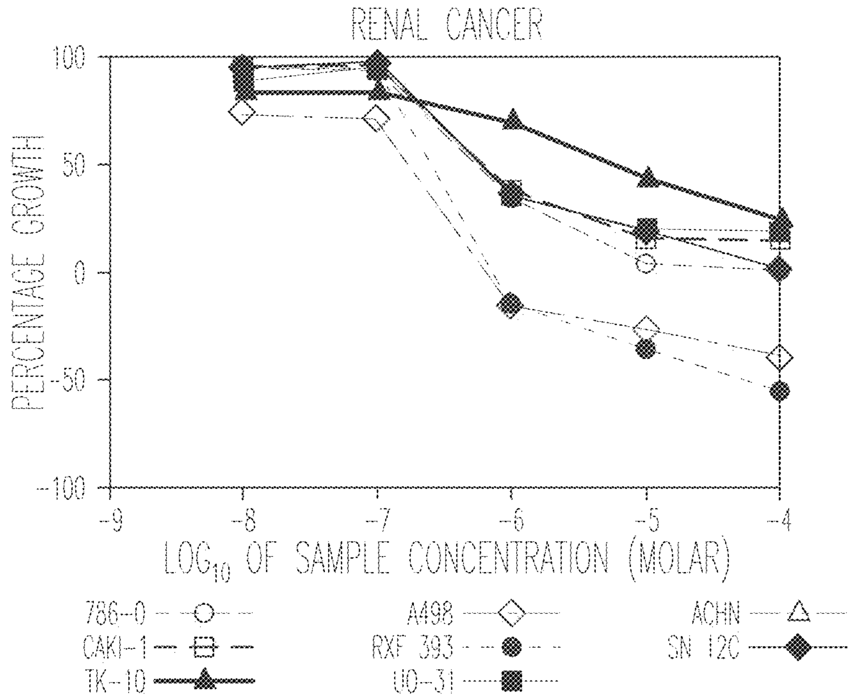
Figure 14H:
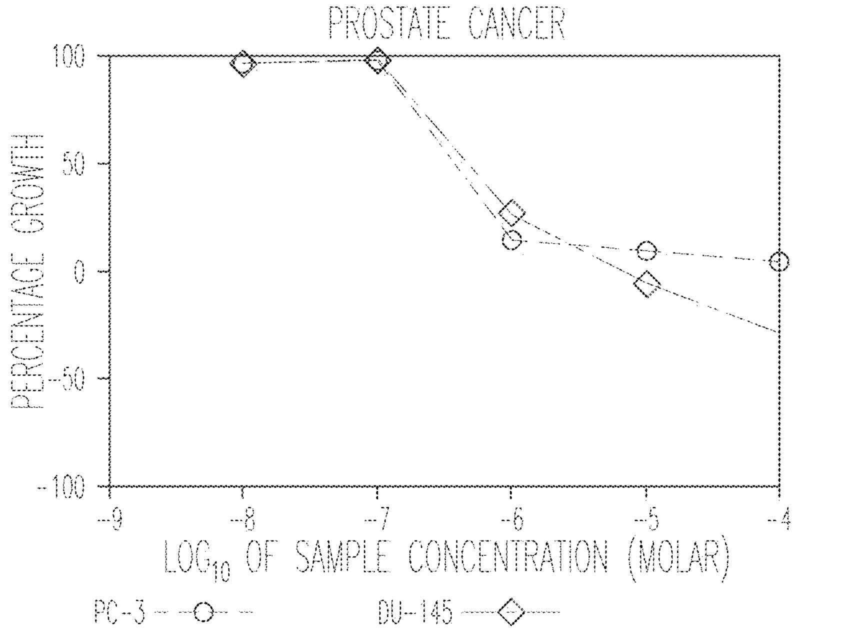
Figure 14I:
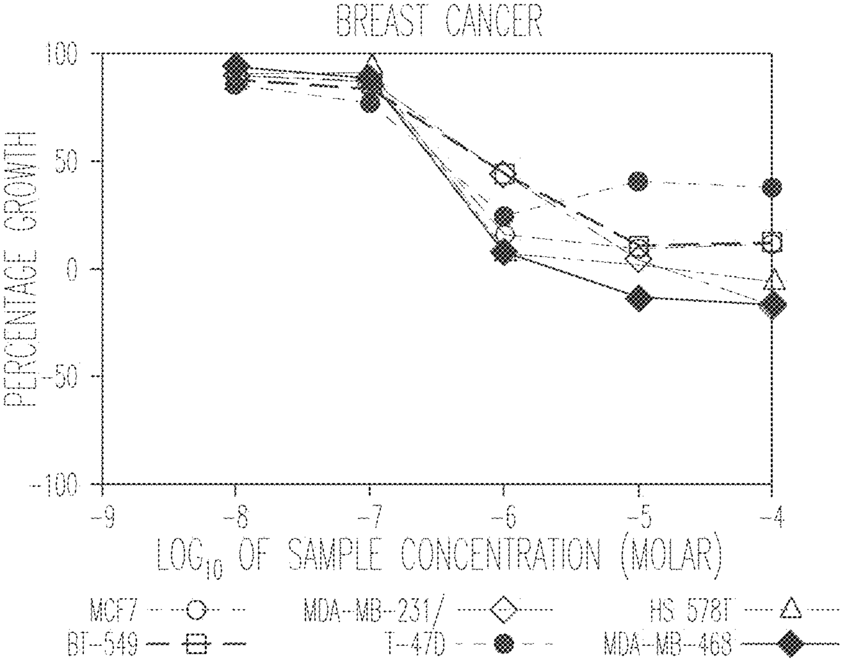
Figure 14J:
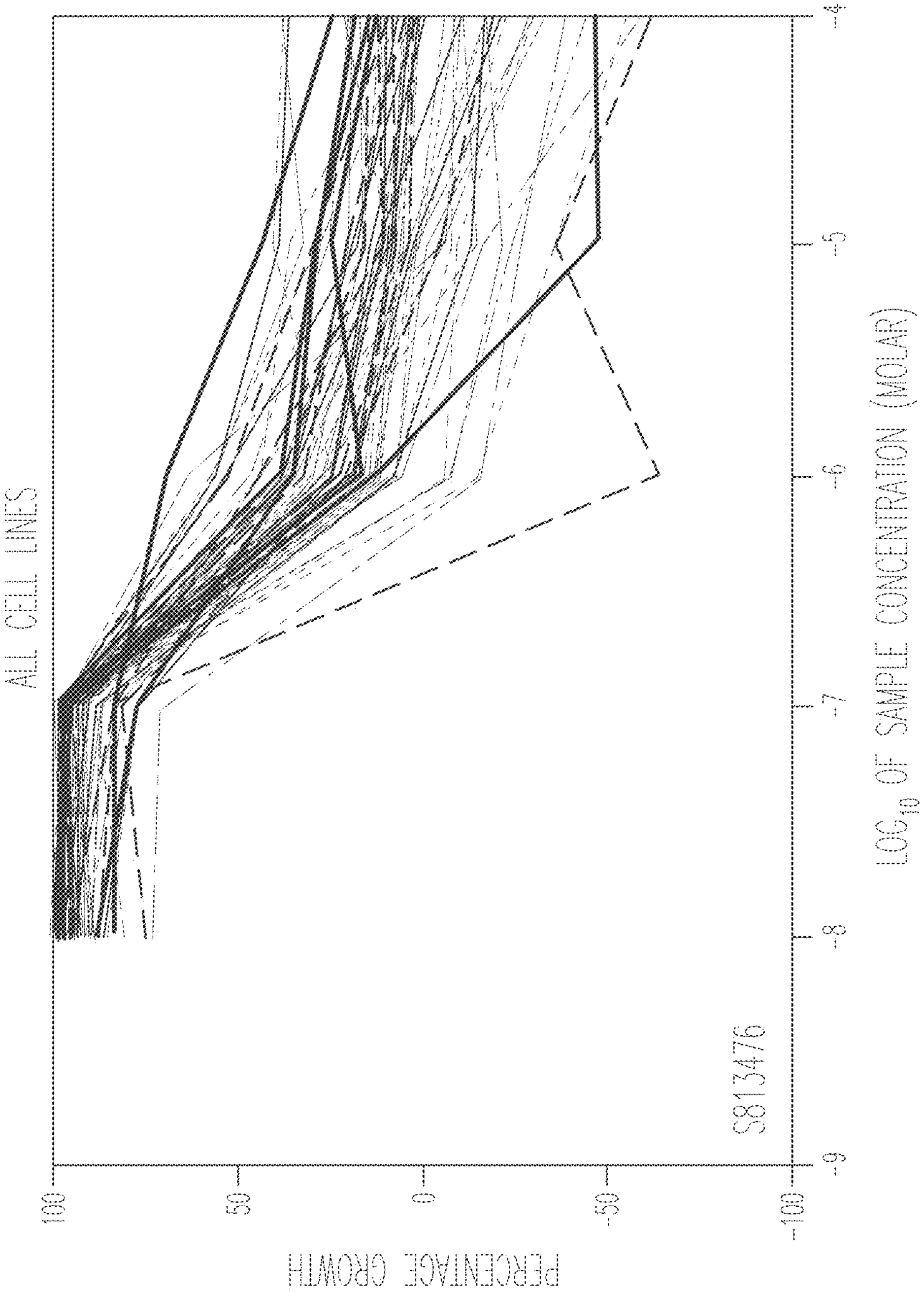
Figure 15:
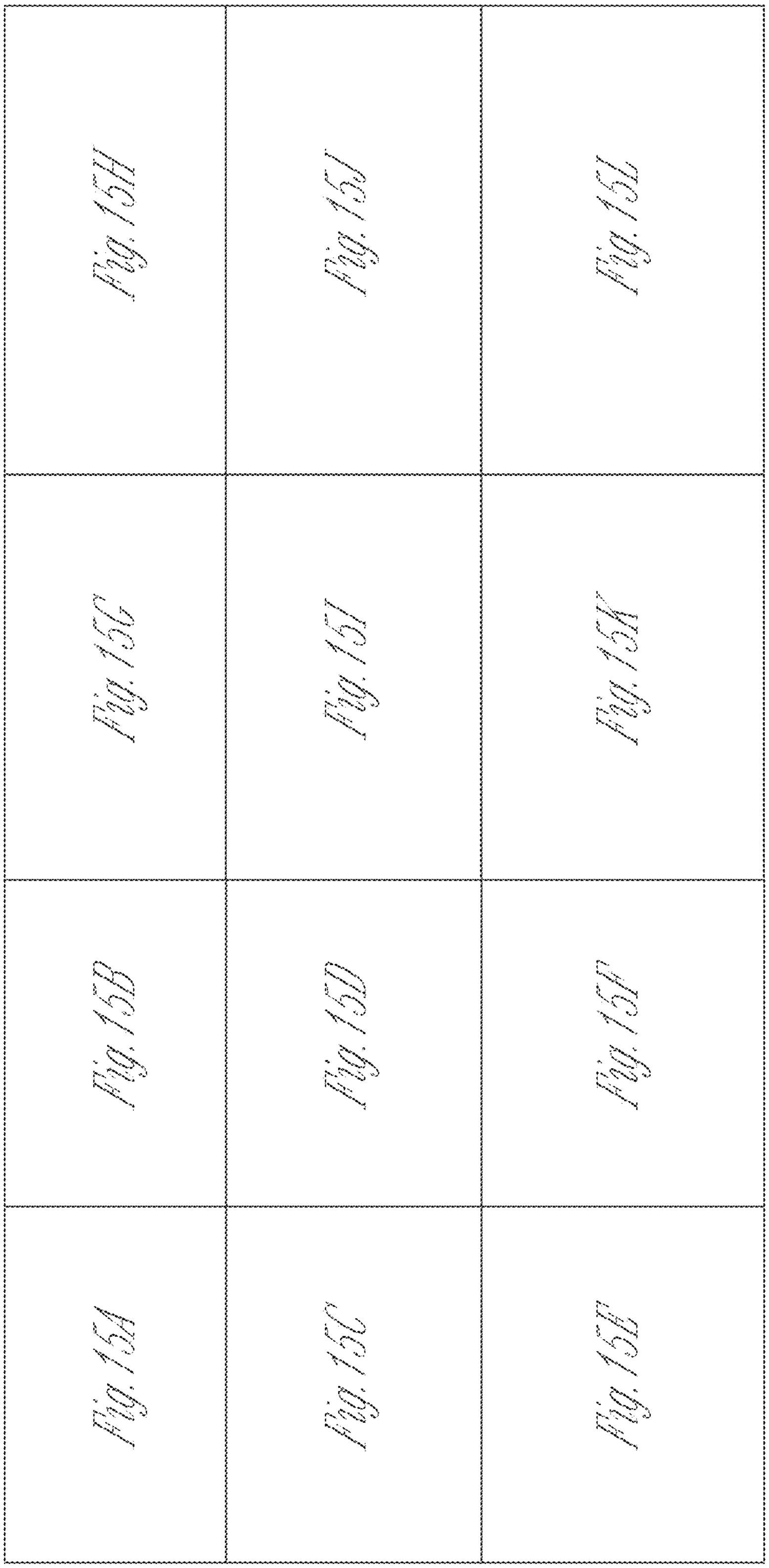
FIG. 15. In vitro testing results.
Figure 15C:
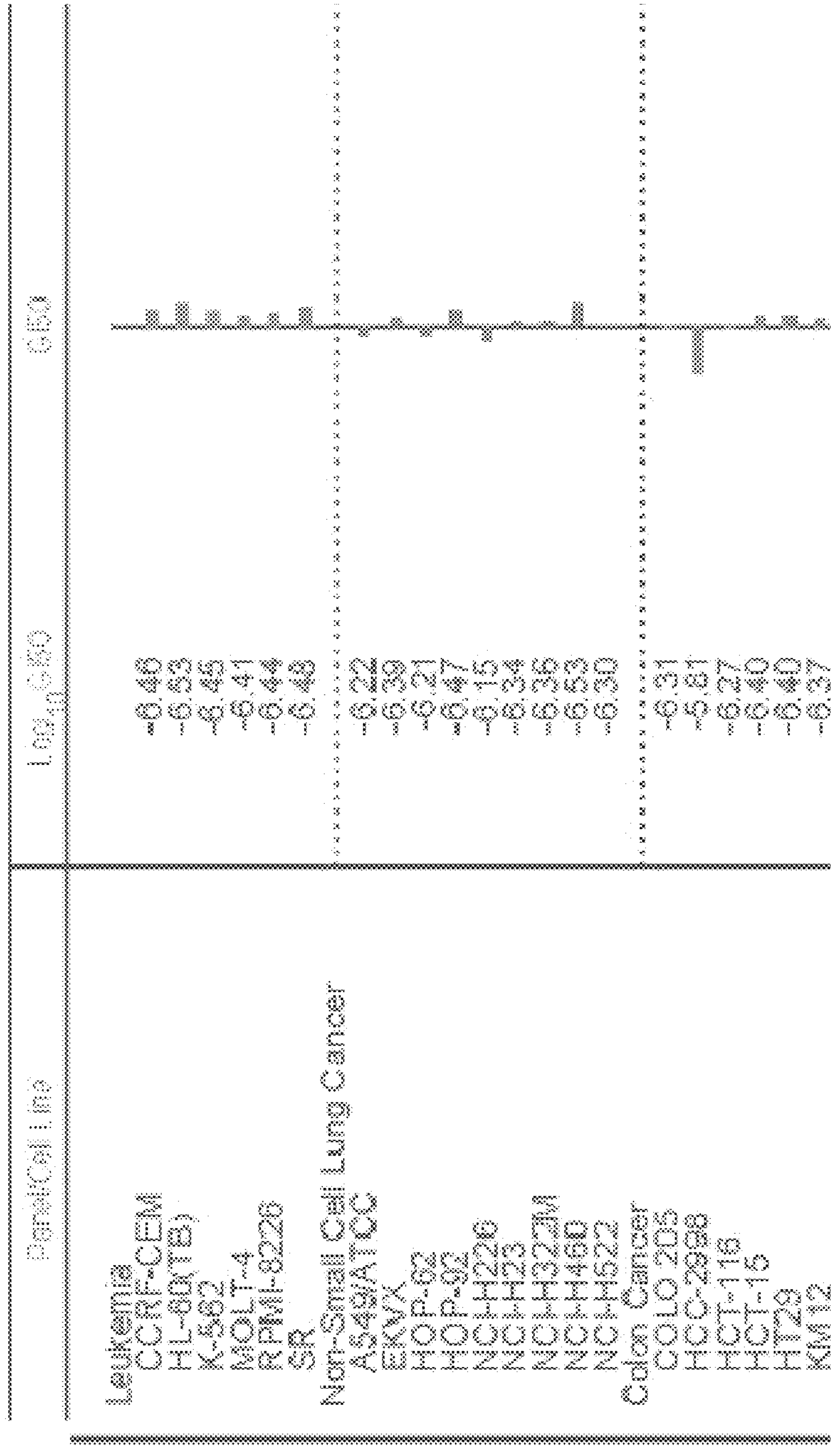
Figure 15H:
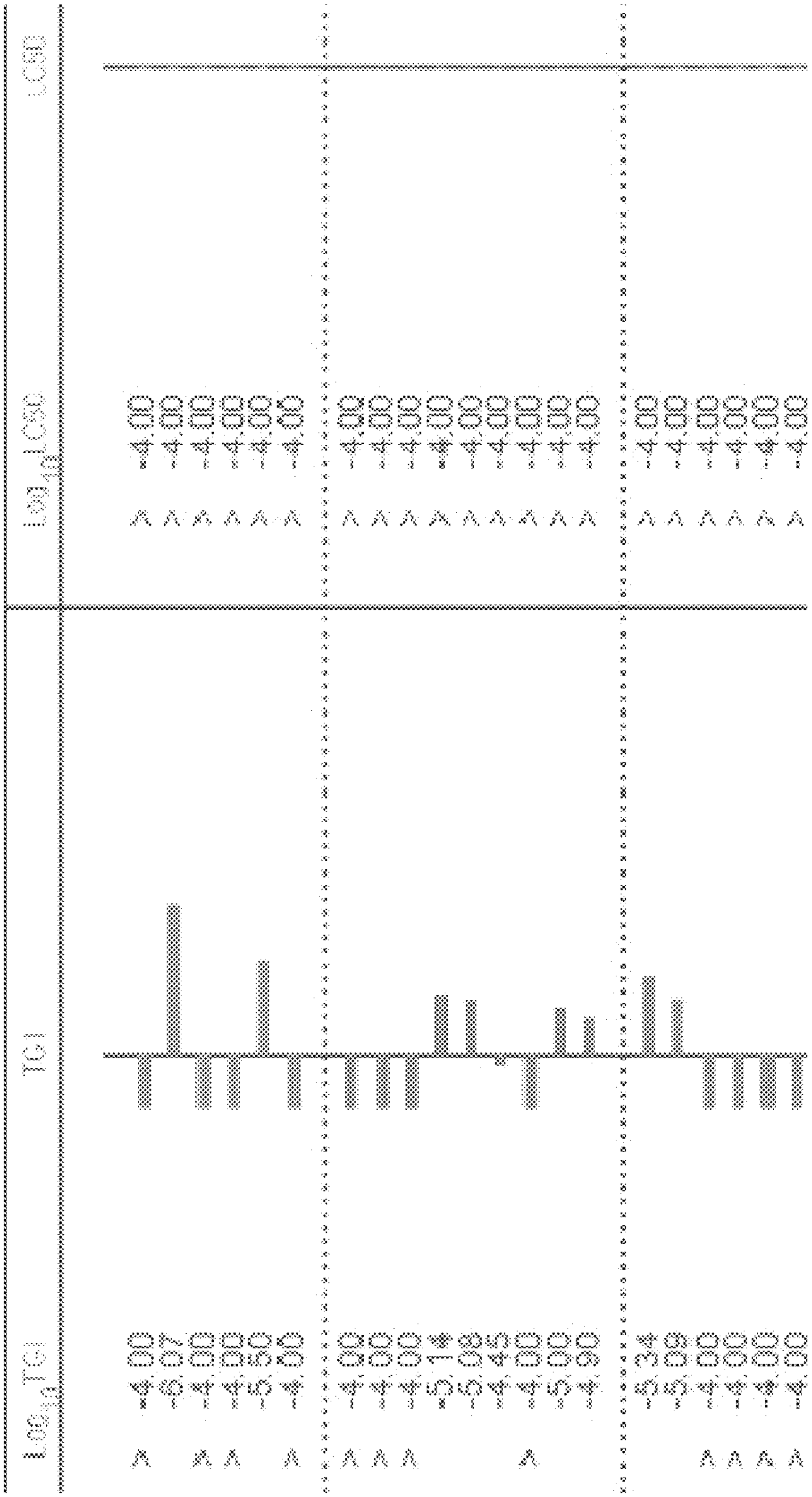
Figure 15I:
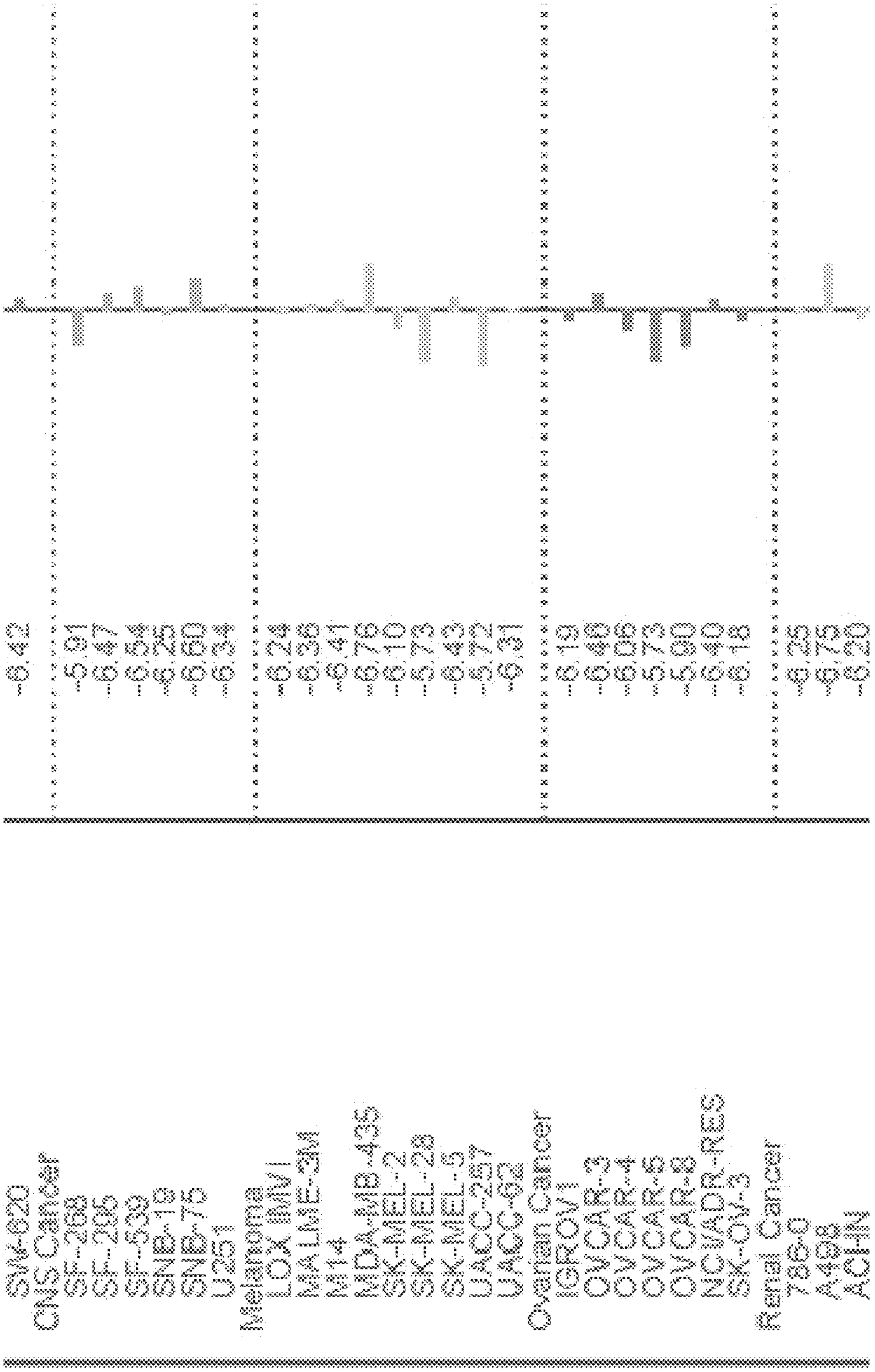
Figure 15J:
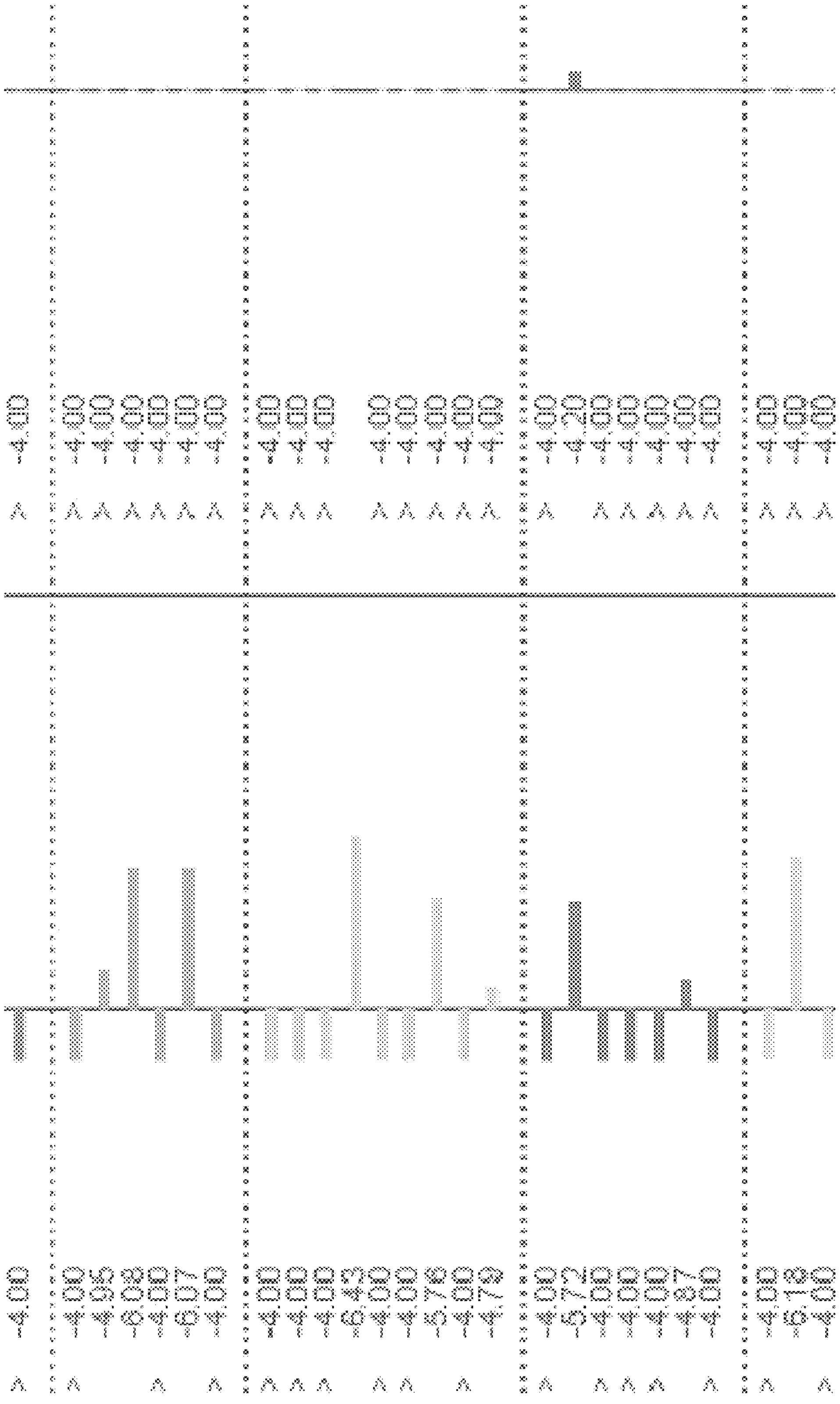
Figure 15K:
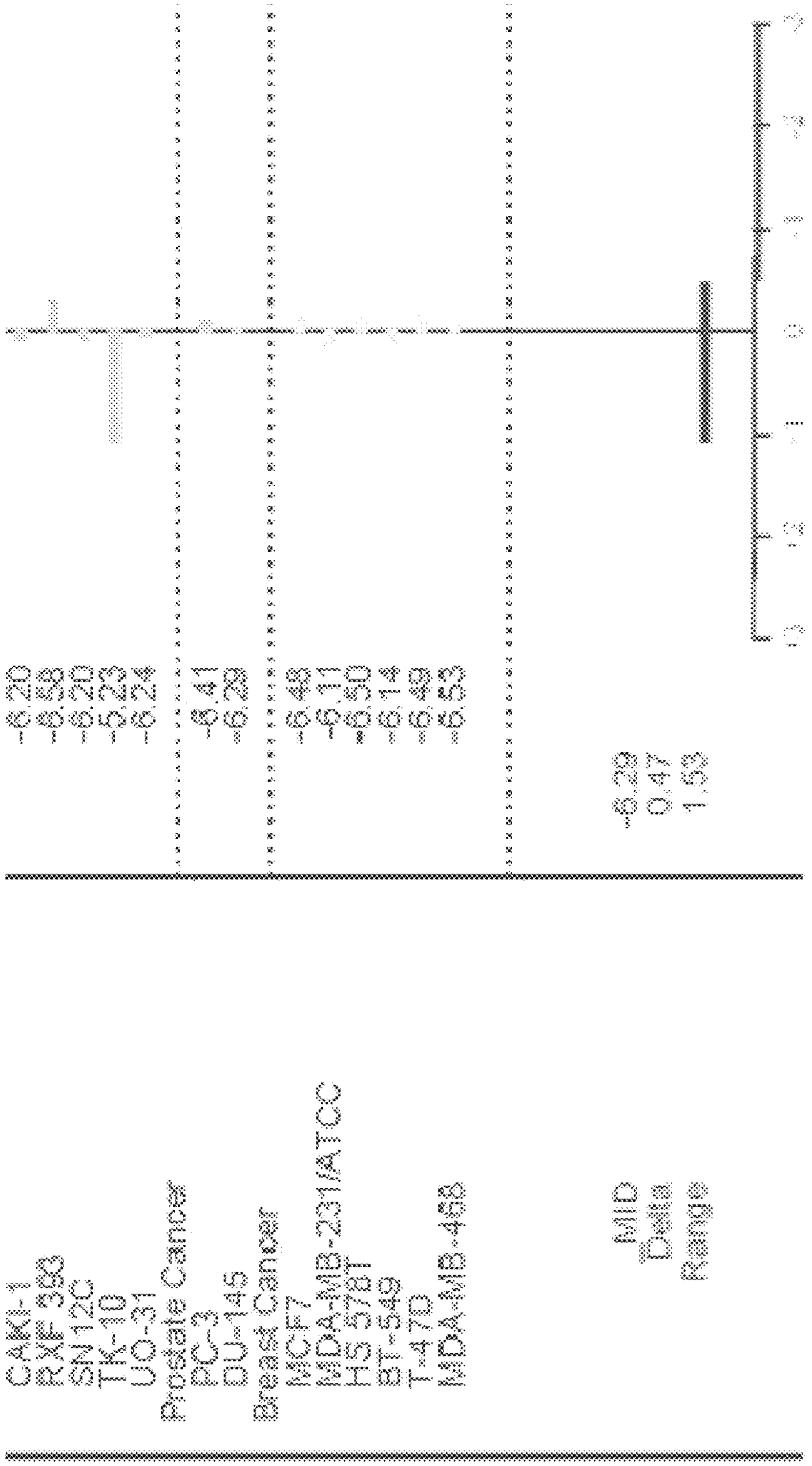
Figure 15L:
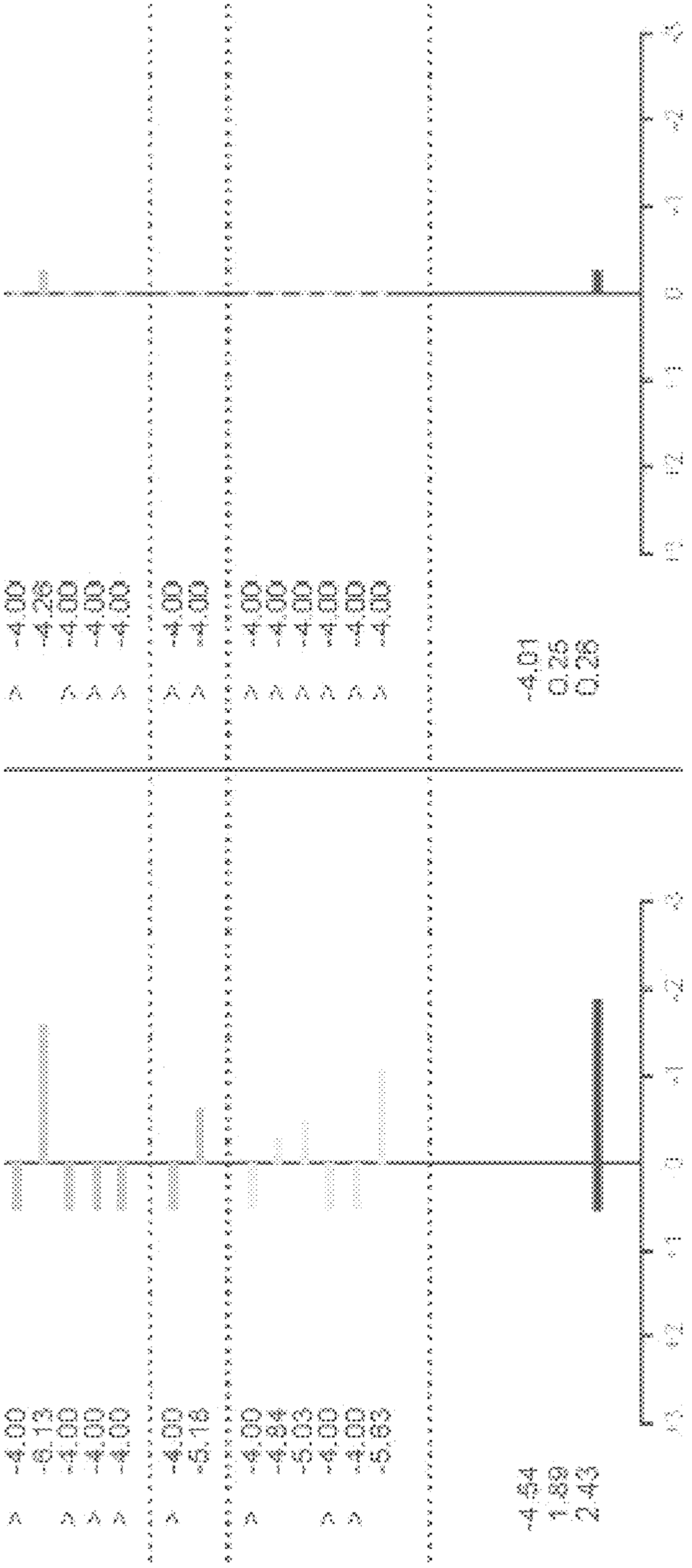
Figure 16:
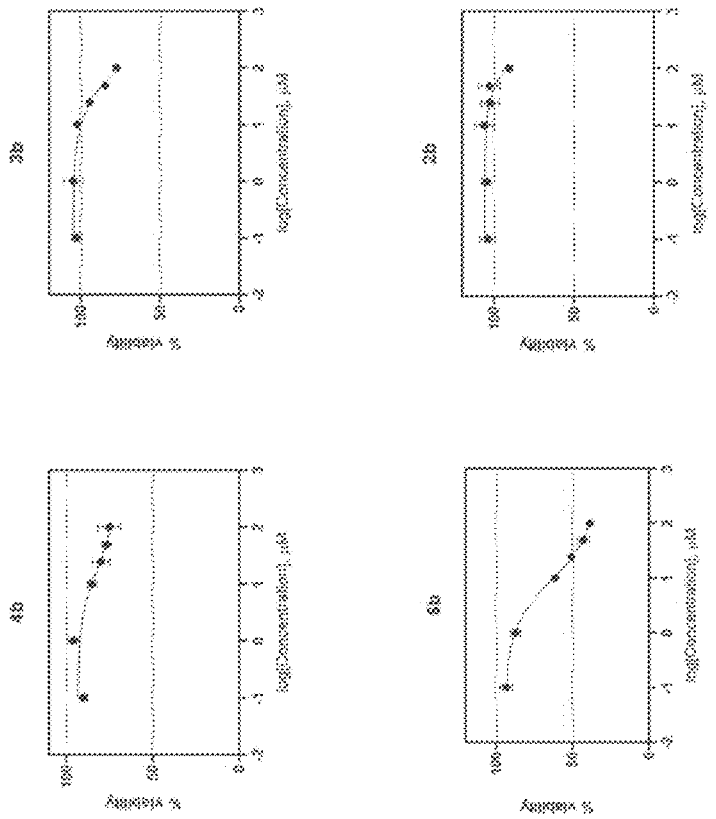
FIG. 16. MTS cell viability testing of exemplary benzamides using A549 cell line.
Figure 17A:
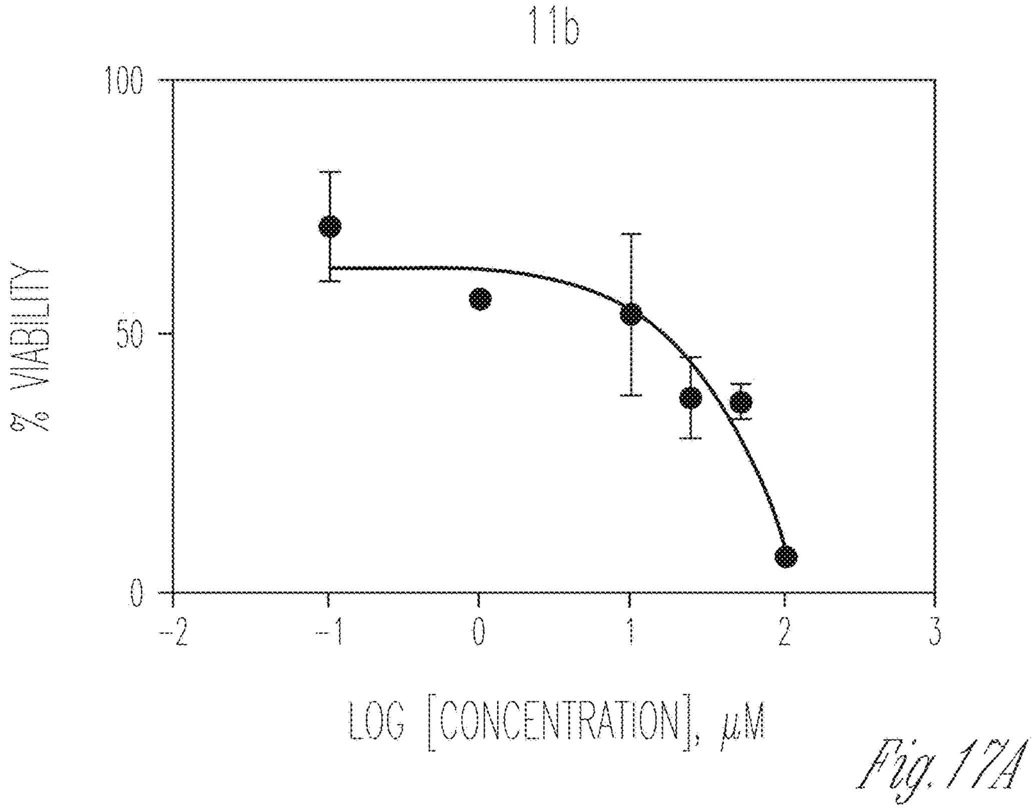
FIG. 17. MTS cell viability testing of exemplary benzylamines using A549 cell line.
Figure 17B:
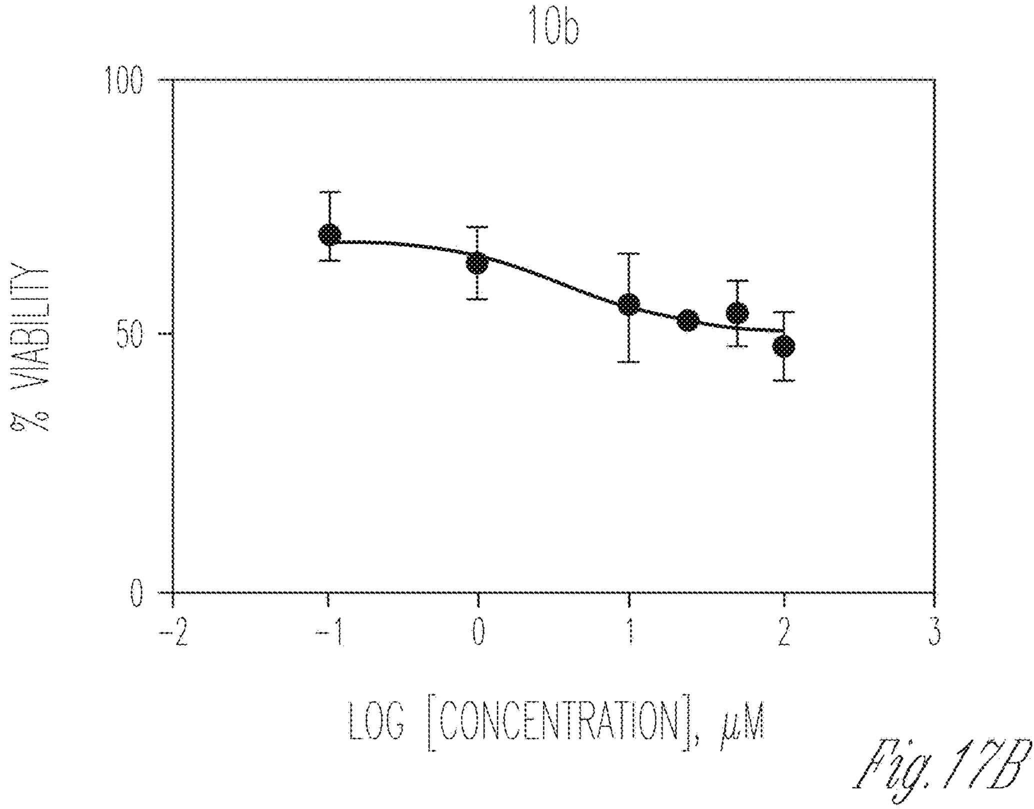
Figure 17C:
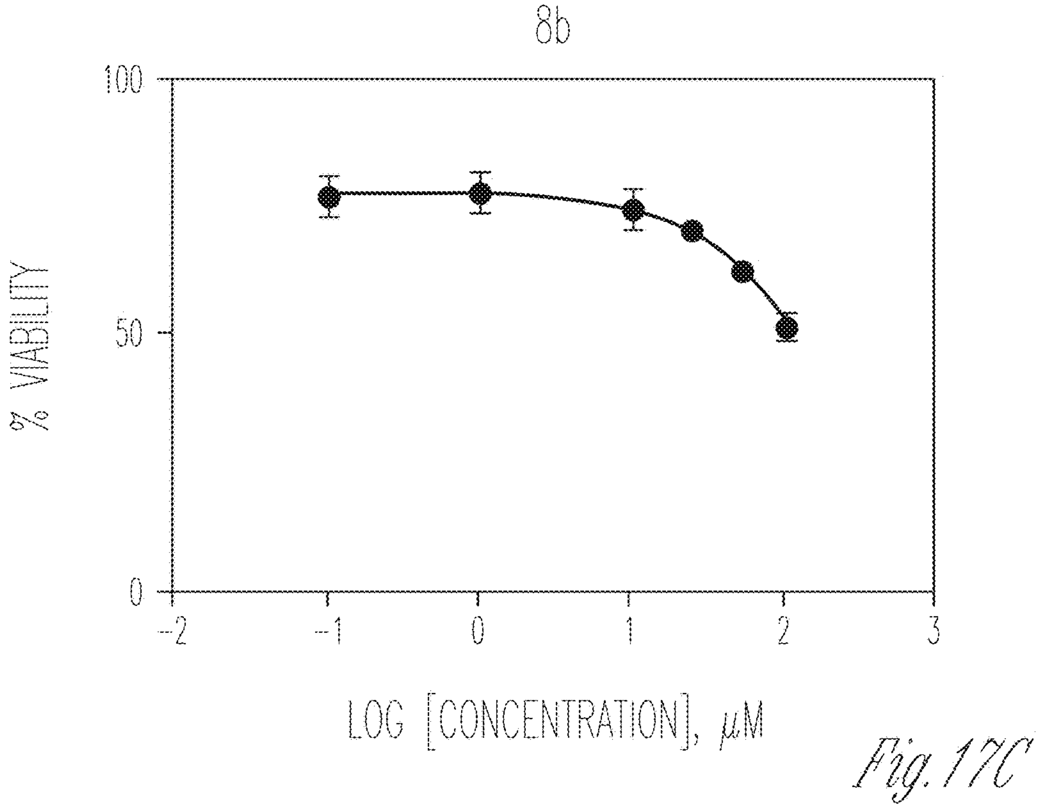
Figure 17D:
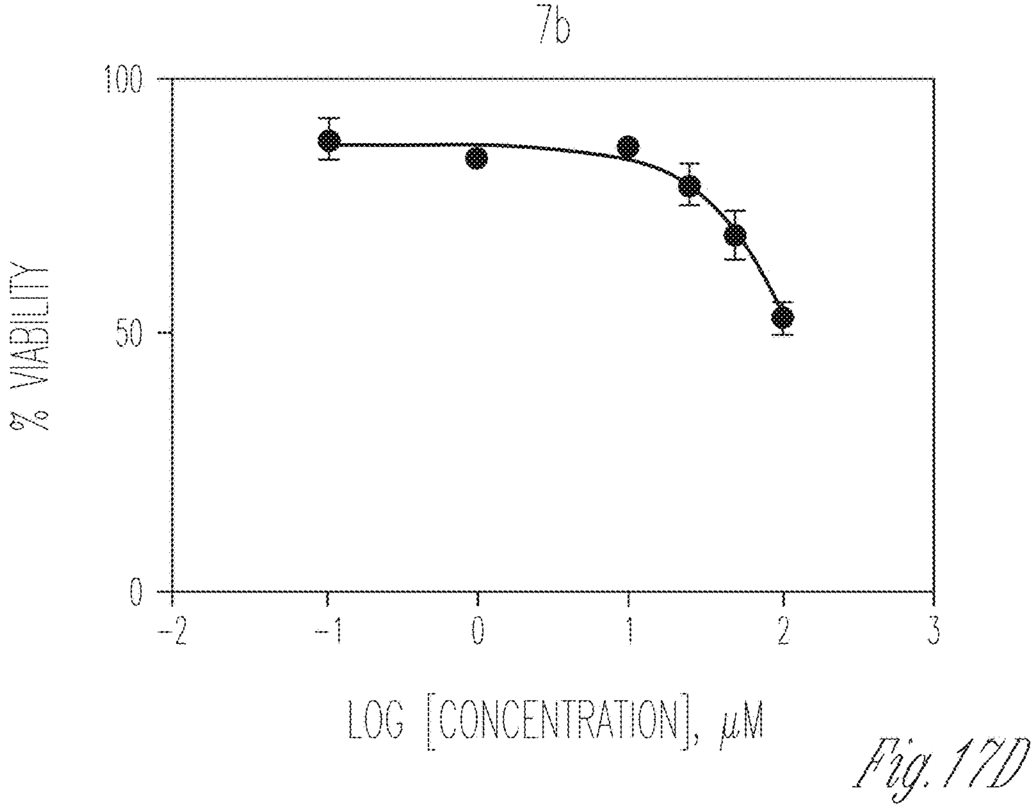
Figure 17E:
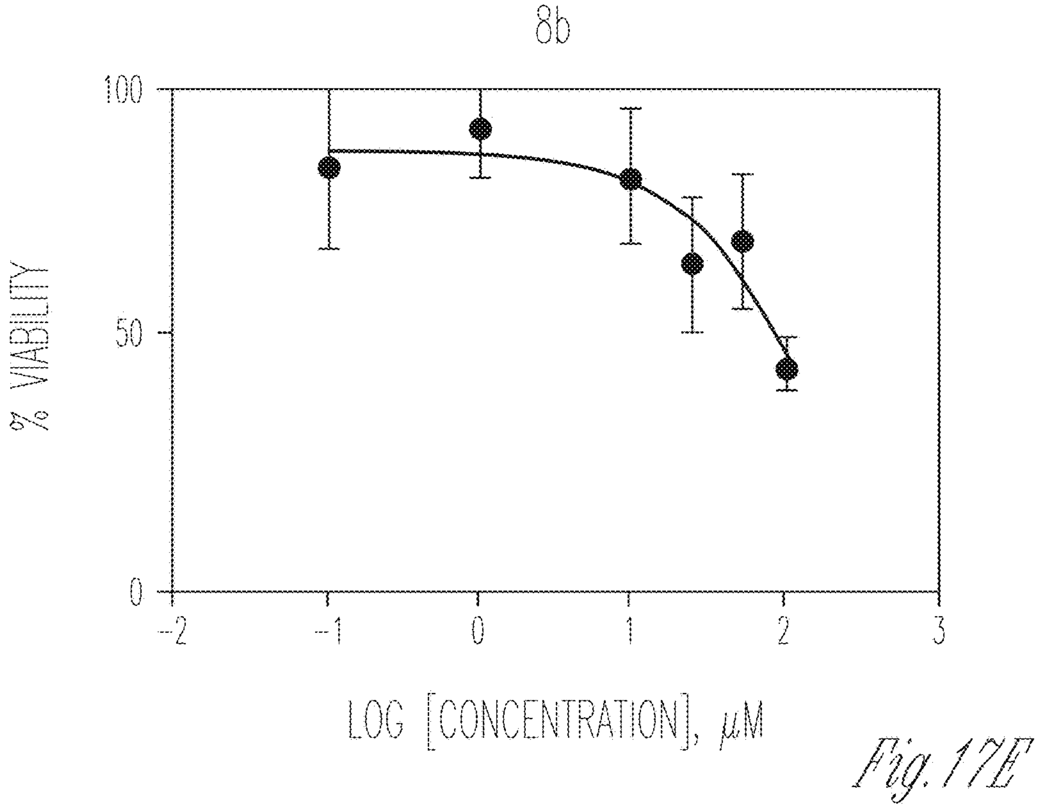
Figure 17F:
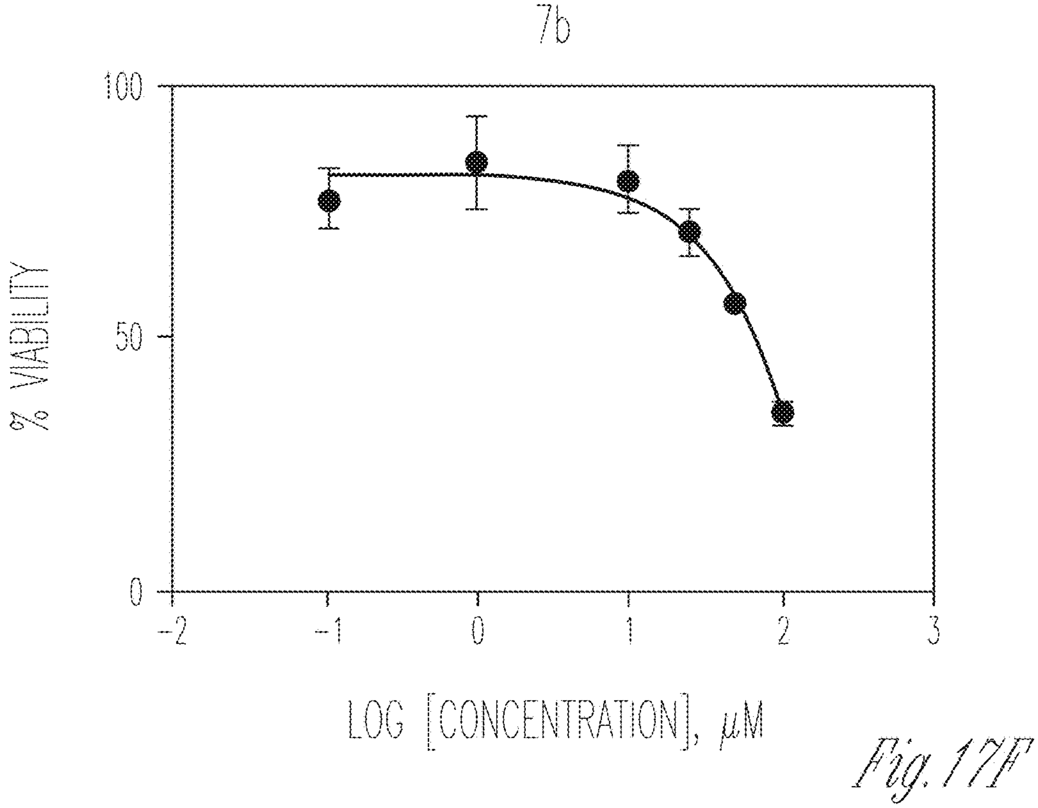
Figure 18:
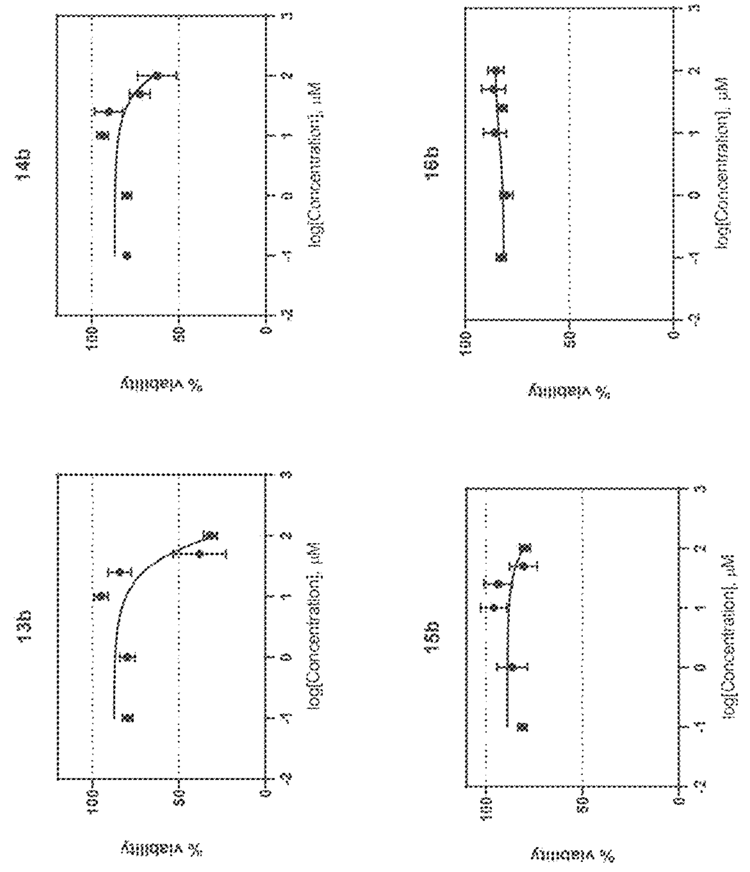
FIG. 18. MTS cell viability testing of exemplar ureas using A549 cell line.
Figure 19A:
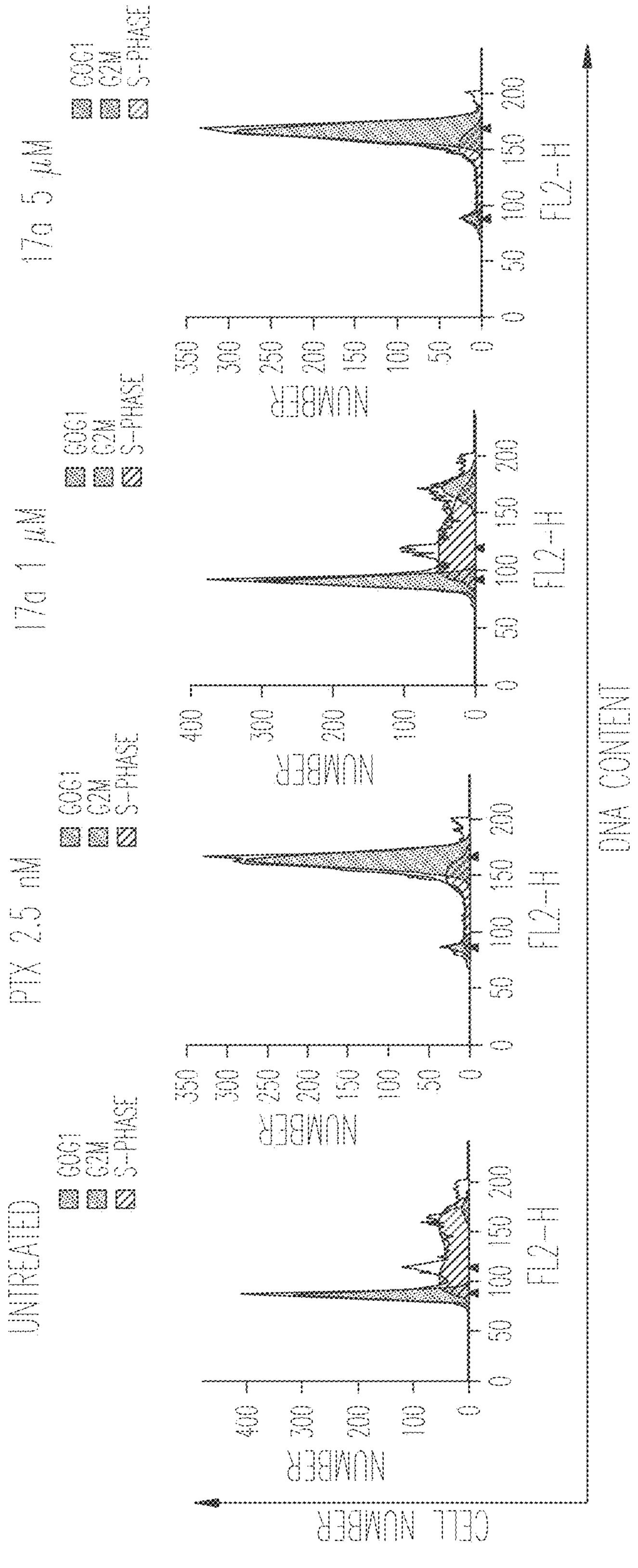
FIG. 19. Cell cycle analysis of cells treated with compound 17a (SA10).
Figure 19B:
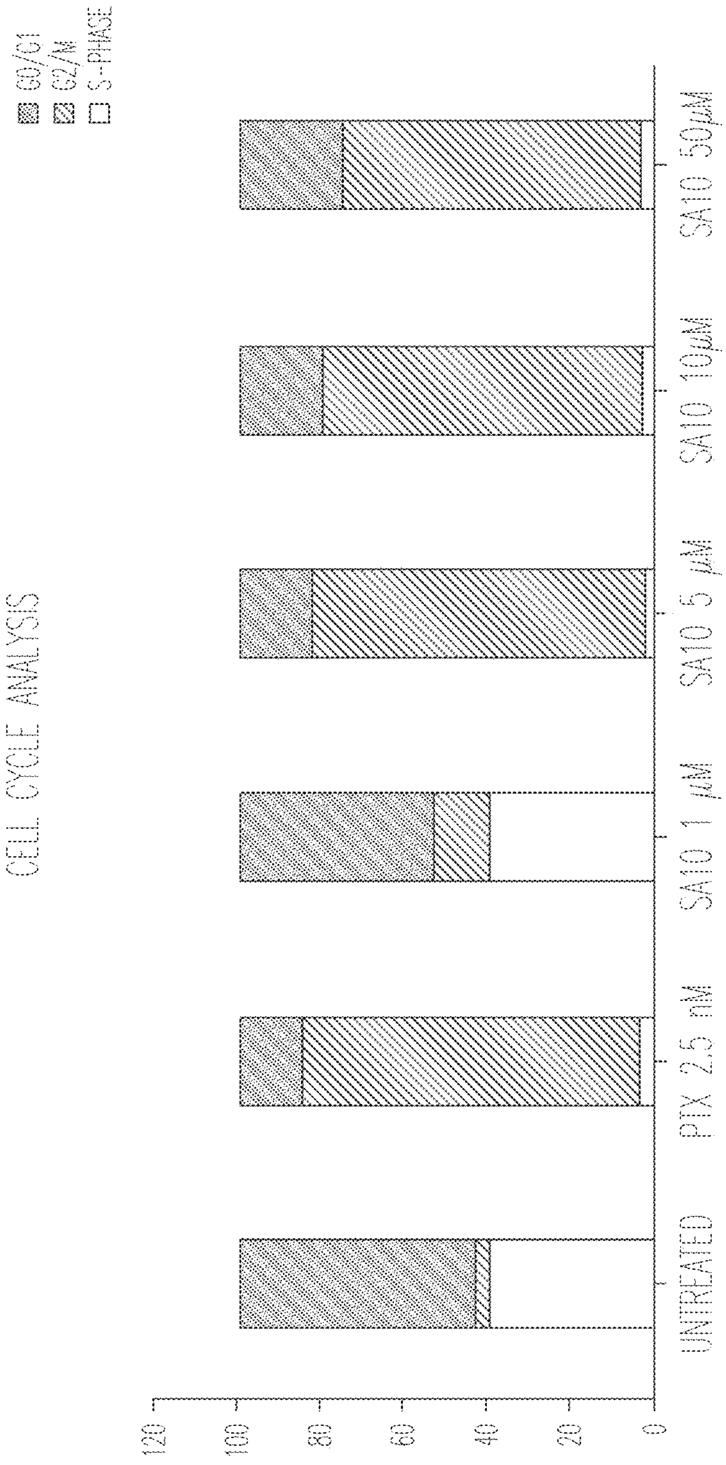
Figure 19C:
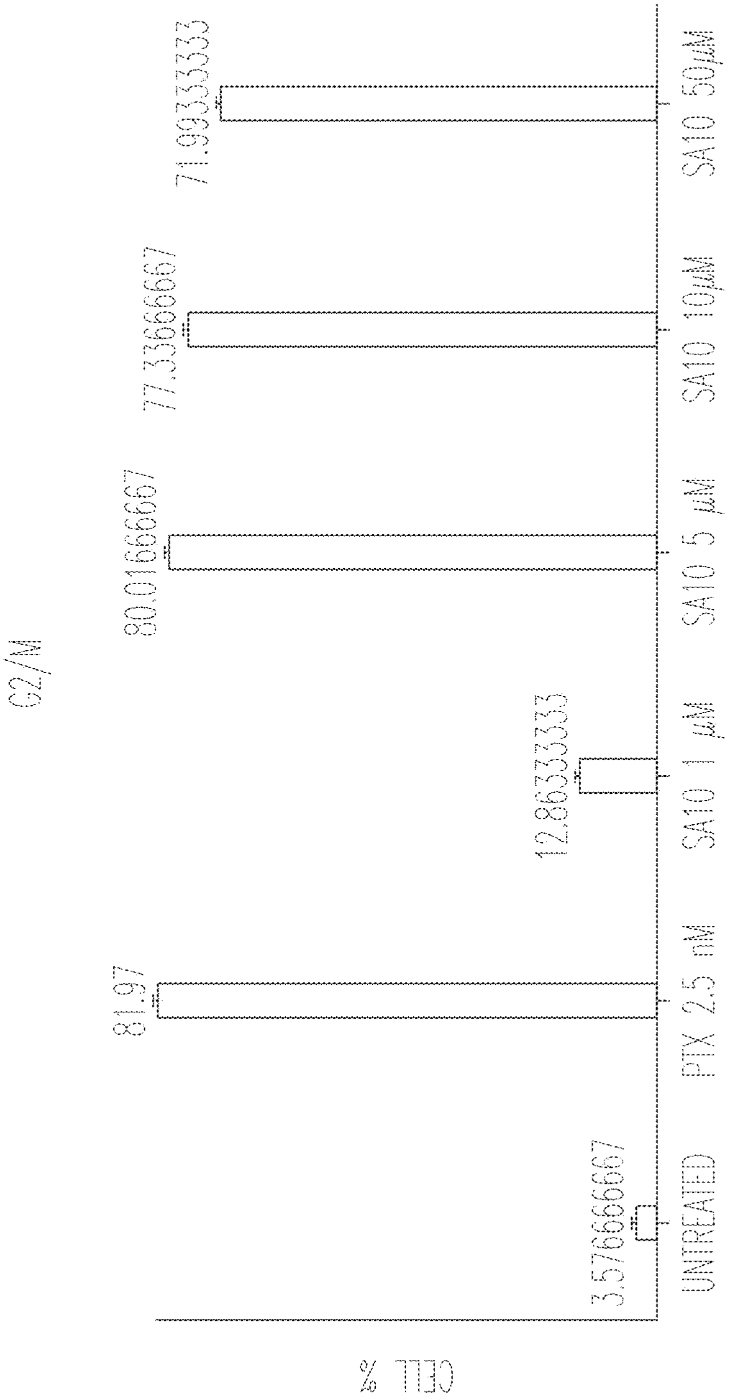
Figure 24A:
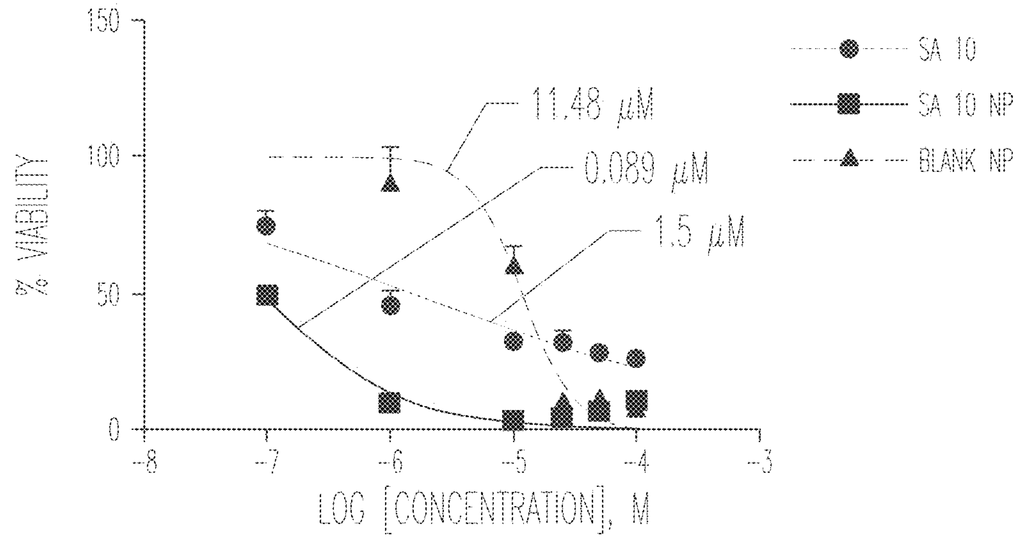
Figure 24B:
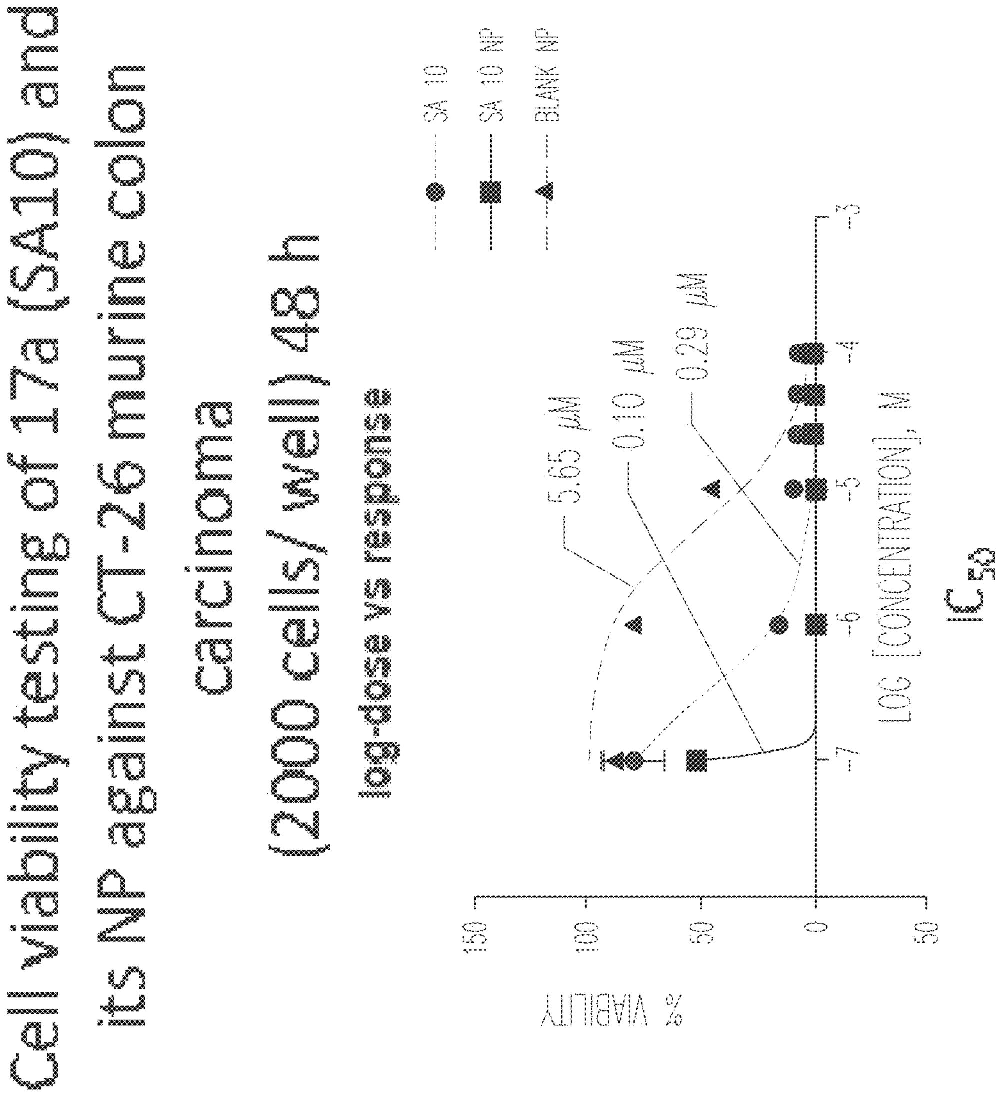
Figure 24C:
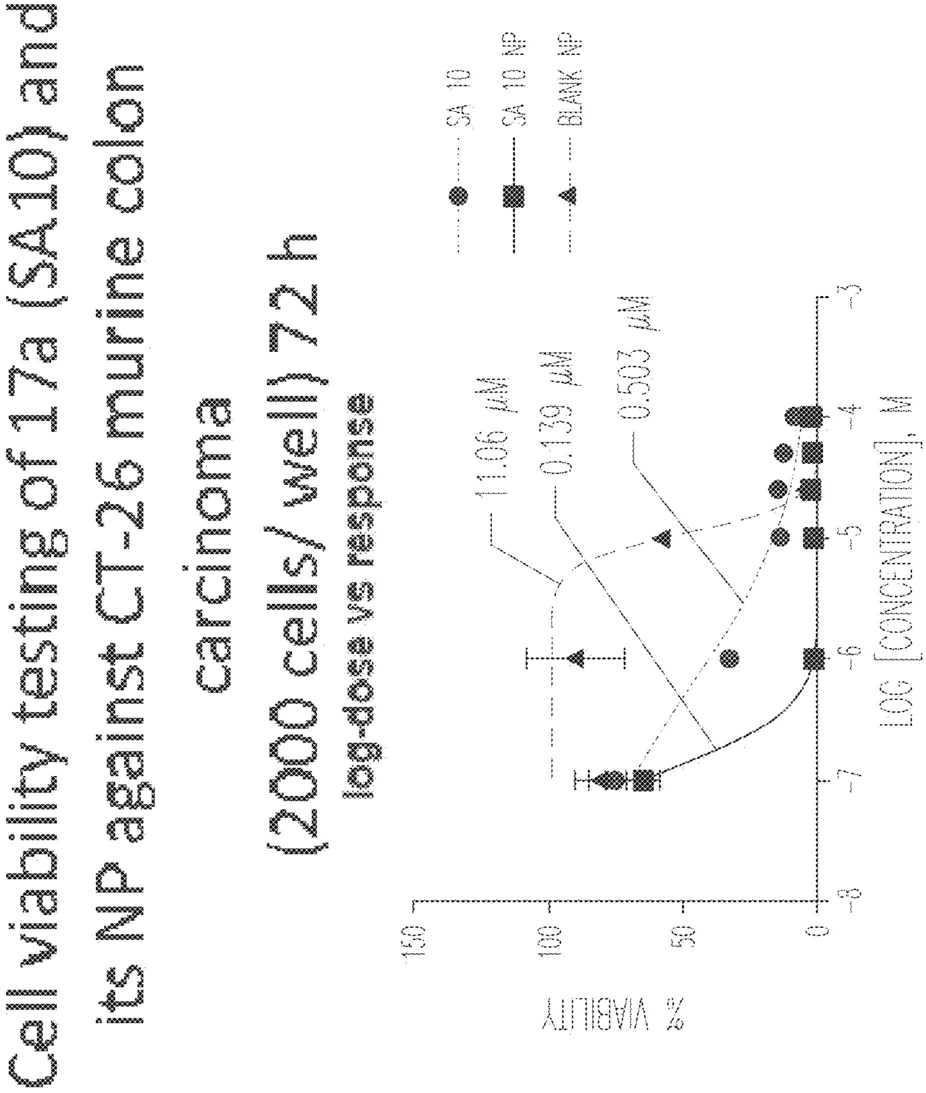

A composition is comprised of "substantially all" of a particular compound, or a particular form a compound (e.g., an isomer) when a composition comprises at least about 90%, 95%, 99%, or 99.9%, of the particular composition on a weight basis. A composition comprises a "mixture" of compounds, or forms of the same compound, when each compound (e.g., isomer) represents at least about 10% of the composition on a weight basis. A compound of the invention, can be prepared as an acid salt or as a base salt, as well as in free acid or free base forms. In solution, certain of the compounds of the invention may exist as zwitterions, wherein counter ions are provided by the solvent molecules themselves, or from other ions dissolved or suspended in the solvent.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the compounds useful in the present invention can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media for example ether, ethyl acetate, ethanol, isopropanol, or acetonitrile. Lists of suitable salts are found in *Remington's Pharmaceutical Sciences,* 17th ed., Mack Publishing Company, Easton, PA, p. 1418 (1985), the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The following definitions are used, unless otherwise described: halo or halogen is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Het can be heteroaryl, which encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine agonist activity using the standard tests described herein, or using other similar tests which are well known in the art. It is also understood by those of skill in the art that the compounds described herein include their various tautomers, which can exist in various states of equilibrium with each other.

"Therapeutically effective amount" is intended to include an amount of a composition useful in the present invention or an amount of the combination of compounds, e.g., to treat or prevent the disease or disorder, or to treat the symptoms of the disease or disorder, in a host. As used herein, "treating" or "treat" includes (i) preventing a pathologic condition from occurring (e.g. prophylaxis); (ii) inhibiting the pathologic condition or arresting its development; (iii) relieving the pathologic condition; and/or diminishing symptoms associated with the pathologic condition.

As used herein, the term "patient" refers to organisms to be treated by the methods of the present invention. Such organisms include, but are not limited to, mammals such as humans. In the context of the invention, the term "subject" generally refers to an individual who will receive or who has received treatment (e.g., administration of a composition of the invention).

"Stable compound" and "stable structure" are meant to indicate a compound that is sufficiently robust to survive isolation to a useful degree of purity from a reaction mixture, and formulation into an efficacious therapeutic agent. Only stable compounds are contemplated by the present invention.

In cases where compounds are sufficiently basic or acidic to form acid or base salts, use of the compounds as salts may be appropriate. Examples of acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Alkyl includes straight or branched $C_{1-10}$ alkyl groups, e.g., methyl, ethyl, propyl, butyl, pentyl, isopropyl, isobutyl, 1-methylpropyl, 3-methylbutyl, hexyl, and the like.

Lower alkyl includes straight or branched $C_{1-6}$ alkyl groups, e.g., methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, and the like.

The term "alkylene" refers to a divalent straight or branched hydrocarbon chain (e.g., ethylene: $-CH_2-CH_2-$).

$C_{3-7}$ Cycloalkyl includes groups such as, cyclopropyl, cyclopentyl, cyclohexyl, cycloheptyl, and the like, and alkyl-substituted $C_{3-7}$ cycloalkyl group, e.g., straight or branched $C_{1-6}$ alkyl group such as methyl, ethyl, propyl, butyl or pentyl, and $C_{5-7}$ cycloalkyl group such as, cyclopentyl or cyclohexyl, and the like.

Lower alkoxy includes $C_{1-6}$ alkoxy groups, such as methoxy, ethoxy or propoxy, and the like.

Lower alkanoyl includes $C_{1-6}$ alkanoyl groups, such as formyl, acetyl, propanoyl, butanoyl, pentanoyl or hexanoyl, and the like.

$C_{7-11}$ aroyl, includes groups such as benzoyl or naphthoyl;

Lower alkoxycarbonyl includes $C_{2-7}$ alkoxycarbonyl groups, such as methoxycarbonyl, ethoxycarbonyl or propoxycarbonyl, and the like.

Lower alkylamino group means amino group substituted by $C_{1-6}$ alkyl group, such as, methylamino, ethylamino, propylamino, butylamino, and the like.

Di(lower alkyl)amino group means amino group substituted by the same or different and $C_{1-6}$ alkyl group (e.g., dimethylamino, diethylamino, ethylmethylamino).

Lower alkylcarbamoyl group means carbamoyl group substituted by $C_{1-6}$ alkyl group (e.g., methylcarbamoyl, ethylcarbamoyl, propylcarbamoyl, butylcarbamoyl).

Di(lower alkyl)carbamoyl group means carbamoyl group substituted by the same or different and $C_{1-6}$ alkyl group (e.g., dimethylcarbamoyl, diethylcarbamoyl, ethylmethylcarbamoyl).

Halogen atom means halogen atom such as fluorine atom, chlorine atom, bromine atom or iodine atom.

Aryl refers to a $C_{6-10}$ monocyclic or fused cyclic aryl group, such as phenyl, indenyl, or naphthyl, and the like.

Heterocyclic or heterocycle refers to monocyclic saturated heterocyclic groups, or unsaturated monocyclic or fused heterocyclic group containing at least one heteroatom, e.g., 0-3 nitrogen atoms (—$NR^d$— where $R^d$ is H, alkyl, or $Y^2$ as defined herein), 0-1 oxygen atom (—O—), and 0-1 sulfur atom (—S—). Non-limiting examples of saturated monocyclic heterocyclic group includes 5 or 6 membered saturated heterocyclic group, such as tetrahydrofuranyl, pyrrolidinyl, morpholinyl, piperidyl, piperazinyl or pyrazolidinyl. Non-limiting examples of unsaturated monocyclic heterocyclic group includes 5 or 6 membered unsaturated heterocyclic group, such as furyl, pyrrolyl, pyrazolyl, imidazolyl, thiazolyl, thienyl, pyridyl or pyrimidinyl. Non-limiting examples of unsaturated fused heterocyclic groups includes unsaturated bicyclic heterocyclic group, such as indolyl, isoindolyl, quinolyl, benzothizolyl, chromanyl, benzofuranyl, and the like. A Het group can be a saturated heterocyclic group or an unsaturated heterocyclic group, such as a heteroaryl group.

$R^2$ and $R^1$ in formula (I) taken together can form a cyclic or heterocyclic ring, or an aryl or heteroaryl ring. Non-limiting examples of heterocyclic rings include 5 or 6 membered saturated heterocyclic rings, such as 1-pyrrolidinyl, 4-morpholinyl, 1-piperidyl, 1-piperazinyl or 1-pyrazolidinyl, 5 or 6 membered unsaturated heterocyclic rings such as 1-imidazolyl, and the like.

The alkyl, alkenyl, or cyclic, e.g., aryl, or heterocyclic, groups of R, or $R^1$ and/or $R^2$, can be optionally substituted with one or more substituents, wherein the substituents are the same or different, and include lower alkyl; cycloalkyl, hydroxyl; hydroxy $C_{1-6}$ alkylene, such as hydroxymethyl, 2-hydroxyethyl or 3-hydroxypropyl; lower alkoxy; $C_{1-6}$ alkoxy $C_{1-6}$ alkyl, such as 2-methoxyethyl, 2-ethoxyethyl or 3-methoxypropyl; amino; alkylamino; dialkyl amino; cyano; nitro; acyl; carboxyl; lower alkoxycarbonyl; halogen; mercapto; $C_{1-6}$ alkylthio, such as, methylthio, ethylthio, propylthio or butylthio; substituted $C_{1-6}$ alkylthio, such as methoxyethylthio, methylthioethylthio, hydroxyethylthio or chloroethylthio; aryl; substituted $C_{6-10}$ monocyclic or fused-cyclic aryl, such as 4-hydroxyphenyl, 4-methoxyphenyl, 4-fluorophenyl, 4-chlorophenyl or 3,4-dichlorophenyl; 5-6 membered unsaturated heterocyclic, such as furyl, pyrrolyl, pyrazolyl, imidazolyl, thiazolyl, thienyl, pyridyl or pyrimidinyl; and bicyclic unsaturated heterocyclic, such as indolyl, isoindolyl, quinolyl, benzothiazolyl, chromanyl, benzofuranyl or phthalimino. In certain embodiments, one or more of the above groups can be expressly excluded as a substituent of various other groups of the formulas.

The alkyl, alkenyl, aryl, non-aryl cyclic, or heterocyclic groups of R can be optionally substituted with one or more substituents, wherein the substituents are the same or different, and include hydroxyl; $C_{1-6}$ alkoxy, such as methoxy, ethoxy or propoxy; carboxyl; $C_{2-7}$ alkoxycarbonyl, such as methoxycarbonyl, ethoxycarbonyl or propoxycarbonyl) or halogen.

The alkyl, alkenyl, aryl, non-aryl cyclic, or heterocyclic groups of R can be optionally substituted with one or more substituents, wherein the substituents are the same or different, and include $C_{3-6}$ cycloalkyl; hydroxyl; $C_{1-6}$ alkoxy; amino; cyano; aryl; substituted aryl, such as 4-hydroxyphenyl, 4-methoxyphenyl, 4-chlorophenyl or 3,4-dichlorophenyl; nitro or halogen.

The ring formed together with $R^2$ and $R^1$ can be optionally substituted with one or more substituents, wherein the substituents are the same or different, and include $C_{1-6}$ alkyl; hydroxy $C_{1-6}$ alkylene; $C_{1-6}$ alkoxy $C_{1-6}$ alkylene; hydroxyl; $C_{1-6}$ alkoxy; or cyano.

A specific value for each of X, R, $R^1$ and/or $R^2$ independently is 2-hydroxyethyl, 3-hydroxypropyl, 4-hydroxybutyl, 2-aminoethyl, 3-aminopropyl, 4-aminobutyl, methoxymethyl, 2-methoxyethyl, 3-methoxypropyl, ethoxymethyl, 2-ethoxyethyl, methylthiomethyl, 2-methylthioethyl, 3-methylthiopropyl, 2-fluoroethyl, 3-fluoropropyl, 2,2,2-trifluoroethyl, cyanomethyl, 2-cyanoethyl, 3-cyanopropyl, methoxycarbonylmethyl, 2-methoxycarbonylethyl, 3-methoxycarbonylpropyl, benzyl, phenethyl, 4-pyridylmethyl, cyclohexylmethyl, 2-thienylmethyl, 4-methoxyphenylmethyl, 4-hydroxyphenylmethyl, 4-fluorophenylmethyl, or 4-chlorophenylmethyl.

A specific value for each of X, R, $R^1$ and/or $R^2$ is independently hydrogen, $CH_3$—, $CH_3$—$CH_2$—, $CH_3CH_2CH_2$—, hydroxy$C_{1-4}$alkylene, or $C_1$-4alkoxy$C_{1-4}$ alkylene.

Another specific value for value for each of X, R, $R^1$ and/or $R^2$ independently is hydrogen, $CH_3$—, $CH_3$—$CH_2$—, $CH_3$—O—$CH_2CH_2$— or $CH_3$—$CH_2$—O—$CH_2CH_2$—.

A specific value for value for R, $R^1$ or $R^2$ is hydrogen, halogen, or $C_1$-4alkyl.

Another specific value for R is hydrogen, chloro, bromo, fluoro, iodo, C—(CO)—NH, (CO)—NH—$CH_3$, $CH_3$—, or $CH_3$—$CH_2$—.

A specific value for R is halo.

A specific value for R is hydrogen.

A specific value for R is $C_{1-6}$alkyl, or substituted $C_{1-6}$alkyl.

A specific value for R is $C_{1-6}$alkoxy or substituted $C_{1-6}$alkoxy.

A specific value for R is Br, H or I.

A specific value for R is a carbocycle, e.g., C5-C7 carbocycle.

A specific value for R is a substituted carbocycle, e.g., C5-C7 carbocycle.

A specific value for R is a heterocycle, e.g., having a ring with 5-7 atoms.

A specific value for R is a substituted heterocycle.

A specific value for R is an aryl, e.g., C5-C7 aryl.

A specific value for R is a substituted aryl.

A specific value for value for $R^1$ and $R^2$ is a C6 cyclic group, e.g., a cyclohexane.

A specific value for value for $R^1$ and $R^2$ is a C7 cyclic group, e.g., a cycloheptane.

Specific substituents for substitution on the alkyl, aryl or other cyclic groups are hydroxy, $C_{1-6}$alkyl, hydroxy$C_{1-6}$alkylene, $C_{1-6}$alkoxy, $C_{1-6}$alkoxy$C_{1-6}$alkylene, $C_{3-6}$cycloalkyl, amino, cyano, halogen, or aryl.

A specific value for X is an amide, amine or imide group.

Another specific value for X is hydrogen, C1-C6alkyl, C—(CO)—NH, (CO)—NH—$CH_3$, $CH_3$—, or $CH_3$—$CH_2$—.

A specific value for X is a chain having up to about 12 atoms; wherein the atoms are selected from the group consisting of carbon, sulfur, nitrogen, and non-peroxide oxygen.

A specific value for X is a carboxyl or carbonyl group.

A specific value for X is a bond or a chain; wherein the atoms are selected from the group consisting of carbon, nitrogen, sulfur, non-peroxide oxygen, and phosphorous.

Another specific value for X is a bond or a chain having from about 3 to about 6 atoms.

Another specific value for X is a bond or a chain having from about 1 to about 5 atoms.

Exemplary Delivery Vehicles

Delivery vehicles for fused thiophenes or JNK inhibitor, e.g., compounds of formula (I) or (II), include, for example, naturally occurring or synthetic polymers that form microparticles, nanoparticles, or other macromolecular complexes capable of mediating delivery of the compounds. Vehicles can also comprise other components or functionalities that further modulate, or that otherwise provide beneficial properties.

In one embodiment, the delivery vehicle is a naturally occurring polymer, e.g., formed of materials including but not limited to albumin, collagen, fibrin, alginate, extracellular matrix (ECM), e.g., xenogeneic ECM, hyaluronan (hyaluronic acid), chitosan, gelatin, keratin, potato starch hydrolyzed for use in electrophoresis, or agar-agar (agarose). In one embodiment, the delivery vehicle comprises a hydrogel. In one embodiment, the composition comprises a naturally occurring polymer. For example, the compounds may be in nanoparticles or microparticles. Table 1 provides exemplary materials for delivery vehicles that are formed of naturally occurring polymers and materials for particles.

TABLE 1

| Particle class | Materials |
|---|---|
| Natural materials or derivatives | Chitosan |
| | Dextran |
| | Gelatine |
| | Albumin |
| | Alginates |
| | Liposomes |
| | Starch |
| Polymer carriers | Polylactic acid |
| | Poly(cyano)acrylates |
| | Polyethyleneimine |
| | Block copolymers |
| | Polycaprolactone |

An exemplary polycaprolactone is methoxy poly(ethylene glycol)/poly(epsilon caprolactone). An exemplary poly lactic acid is poly(D,L-lactic-co-glycolic) acid (PLGA).

Some examples of materials for particle formation include but are not limited to agar acrylic polymers, polyacrylic acid, poly acryl methacrylate, gelatin, poly(lactic acid), pectin(poly glycolic acid), cellulose derivatives, cellulose acetate phthalate, nitrate, ethyl cellulose, hydroxyl ethyl cellulose, hydroxypropylcellulose, hydroxyl propyl methyl cellulose, hydroxypropylmethylcellulose phthalate, methyl cellulose, sodium carboxymethylcellulose, poly(ortho esters), polyurethanes, poly(ethylene glycol), poly(ethylene vinyl acetate), polydimethylsiloxane, poly(vinyl acetate phthalate), polyvinyl alcohol, polyvinyl pyrrollidone, and shellac. Soluble starch and its derivatives for particle preparation include amylodextrin, amylopectin and carboxy methyl starch.

In one embodiment, the polymers in the nanoparticles or microparticles are biodegradable. Examples of biodegradable polymers useful in particles preparation include synthetic polymers, e.g., polyesters, poly(ortho esters), polyanhydrides, or polyphosphazenes; natural polymers including proteins (e.g., collagen, gelatin, and albumin), or polysaccharides (e.g., starch, dextran, hyaluronic acid, and chitosan). For instance, a biocompatible polymer includes poly (lactic) acid (PLA), poly (glycolic acid) (PLGA). Natural polymers that may be employed in particles (or as the delivery vehicle) include but are not limited to albumin, chitin, starch, collagen, chitosan, dextrin, gelatin, hyaluronic acid, dextran, fibrinogen, alginic acid, casein, fibrin, and polyanhydrides.

In one embodiment, the delivery vehicle is a hydrogel. Hydrogels can be classified as those with chemically crosslinked networks having permanent junctions or those with physical networks having transient junctions arising from polymer chain entanglements or physical interactions, e.g., ionic interactions, hydrogen bonds or hydrophobic interactions. Natural materials useful in hydrogels include natural polymers, which are biocompatible, biodegradable, support cellular activities, and include proteins like fibrin, collagen and gelatin, and polysaccharides like starch, alginate and agarose.

In one embodiment, the delivery vehicle comprises inorganic nanoparticles, e.g., calcium phosphate or silica particles; polymers including but not limited to poly(lactic-co-glycolic acid) (PLGA), polylactic acid (PLA), linear and/or branched PEI with differing molecular weights (e.g., 2, 22 and 25 kDa), dendrimers such as polyamidoamine (PAMAM) and polymethoacrylates; lipids including but not limited to cationic liposomes, cationic emulsions, DOTAP, DOTMA, DMRIE, DOSPA, distearoylphosphatidylcholine (DSPC), DOPE, or DC-cholesterol; peptide based vectors including but not limited to Poly-L-lysine or protamine; or poly(β-amino ester), chitosan, PEI-polyethylene glycol, PEI-mannose-dextrose, DOTAP-cholesterol or RNAiMAX.

In one embodiment, the delivery vehicle is a glycopolymer-based delivery vehicle, poly(glycoamidoamine)s (PGAAs), that have the ability to complex with various polynucleotide types and form nanoparticles. These materials are created by polymerizing the methylester or lactone derivatives of various carbohydrates (D-glucarate (D), meso-galactarate (G), D-mannarate (M), and L-tartarate (T)) with a series of oligoethyleneamine monomers (containing between 1-4 ethylenamines. A subset composed of these carbohydrates and four ethyleneamines in the polymer repeat units yielded exceptional delivery efficiency.

In one embodiment, the delivery vehicle comprises polyethyleneimine (PEI), Polyamidoamine (PAMAM), PEI-PEG, PEI-PEG-mannose, dextran-PEI, OVA conjugate, PLGA microparticles, or PLGA microparticles coated with PAMAM.

In one embodiment, the delivery vehicle comprises a cationic lipid, e.g., N-[1-(2,3-dioleoyloxy)propel]-N,N,N-trimethylammonium (DOTMA), 2,3-dioleyloxy-N-[2-spermine carboxamide] ethyl-N,N-dimethyl-1-propanammonium trifluoracetate (DOSPA, Lipofectamine); 1,2-dioleoyl-3-trimethylammonium-propane (DOTAP); N-[1-(2,3-dimyristloxy) propyl]; N,N-dimethyl-N-(2-hydroxyethyl) ammonium bromide (DMRIE), 3-β-[N—(N,N-dimethyl-aminoethane) carbamoyl] cholesterol (DC-Chol); dioctadecyl amidoglyceryl spermine (DOGS, Transfectam); or imethyldioctadeclyammonium bromide (DDAB). The positively charged hydrophilic head group of cationic lipids usually consists of monoamine such as tertiary and quaternary amines, polyamine, amidinium, or guanidinium group. A series of pyridinium lipids have been developed. In addition to pyridinium cationic lipids, other types of heterocyclic head group include imidazole, piperizine and amino acid. The main function of cationic head groups is to condense negatively charged nucleic acids by means of electrostatic interaction to slightly positively charged nanoparticles, leading to enhanced cellular uptake and endosomal escape.

Lipids having two linear fatty acid chains, such as DOTMA, DOTAP and SAINT-2, or DODAC, may be employed as a delivery vehicle, as well as tetraalkyl lipid chain surfactant, the dimer of N,N-dioleyl-N,N-dimethyl-ammonium chloride (DODAC). All the trans-orientated lipids regardless of their hydrophobic chain lengths ($C_{16:1}$, $C_{18:1}$ and $C_{20:1}$) appear to enhance the transfection efficiency compared with their cis-orientated counterparts.

The structures of cationic polymers useful as a delivery vehicle include but are not limited to linear polymers such as chitosan and linear poly(ethyleneimine), branched polymers such as branch poly(ethyleneimine) (PEI), circle-like polymers such as cyclodextrin, network (crosslinked) type polymers such as crosslinked poly(amino acid) (PAA), and dendrimers.

Dendrimers consist of a central core molecule, from which several highly branched arms ‘grow’ to form a tree-like structure with a manner of symmetry or asymmetry. Examples of dendrimers include polyamidoamine (PAMAM) and polypropylenimine (PPI) dendrimers.

DOPE and cholesterol are commonly used neutral co-lipids for preparing cationic liposomes. Branched PEI-cholesterol water-soluble lipopolymer conjugates self-assemble into cationic micelles. Pluronic (poloxamer), a non-ionic polymer and SP1017, which is the combination of Pluronics L61 and F127, may also be used.

In one embodiment, PLGA particles are employed to increase the encapsulation frequency although complex formation with PLL may also increase the encapsulation efficiency. Other cationic materials, for example, PEI, DOTMA, DC-Chol, or CTAB, may be used to make nanospheres.

In one embodiment, the particles comprise at least one polymeric material. In one embodiment, the polymeric material is biodegradable. In one embodiment, polymeric materials include: silk, elastin, chitin, chitosan, poly(α-hydroxy acids), poly(anhydrides), and poly(orthoesters). In one embodiment, the biodegradable microparticle may comprise polyethylene glycol, poly(lactic acid), poly(glycolic acid), copolymers of lactic and glycolic acid, copolymers of lactic and glycolic acid with polyethylene glycol, poly(E-caprolactone), poly(3-hydroxybutyrate), poly(p-dioxanone), polypropylene fumarate, poly(orthoesters), polyol/diketene acetals addition polymers, poly(sebacic anhydride) (PSA), poly(carboxybiscarboxyphenoxyphenoxy hexone (PCPP) poly[bis (p-carboxypheonoxy) methane] (PCPM), copolymers of SA, CPP and CPM, poly(amino acids), poly(pseudo amino acids), polyphosphazenes, derivatives of poly[(dichloro)phosphazenes] and poly[(organo) phosphazenes], poly-hydroxybutyric acid, or S-caproic acid, polylactide-co-glycolide, polylactic acid, and polyethylene glycol. Polyesters may be employed. In one embodiment, PLGA is employed, e.g., PLGA 75:25, PLGA 50:50 and PLGA 85:15.

Exemplary Particle Sizes (Diameters)

In one embodiment, the particle is a nanoparticle. In one embodiment, the particle may be about 50 nm to less than about 1000 nm, about 100 nm to about 900 nm, about 400 nm to about 800 nm, or about 500 nm to about 700 nm, in diameter. In various aspects, the nanoparticles which range in size from about 1 nm to about 250 nm in mean diameter, about 1 nm to about 240 nm in mean diameter, about 1 nm to about 230 nm in mean diameter, about 1 nm to about 220 nm in mean diameter, about 1 nm to about 210 nm in mean diameter, about 1 nm to about 200 nm in mean diameter, about 1 nm to about 190 nm in mean diameter, about 1 nm to about 180 nm in mean diameter, about 1 nm to about 170 nm in mean diameter, about 1 nm to about 160 nm in mean diameter, about 1 nm to about 150 nm in mean diameter, about 1 nm to about 140 nm in mean diameter, about 1 nm to about 130 nm in mean diameter, about 1 nm to about 120 nm in mean diameter, about 1 nm to about 110 nm in mean diameter, about 1 nm to about 100 nm in mean diameter, about 1 nm to about 90 nm in mean diameter, about 1 nm to about 80 nm in mean diameter, about 1 nm to about 70 nm in mean diameter, about 1 nm to about 60 nm in mean diameter, about 1 nm to about 50 nm in mean diameter, about 1 nm to about 40 nm in mean diameter, about 1 nm to about 30 nm in mean diameter, or about 1 nm to about 20 nm in mean diameter, about 1 nm to about 10 nm in mean diameter. In other aspects, the size of the nanoparticles is from about 5 nm to about 150 nm (mean diameter), from about 5 to about 50 nm, from about 10 to about 30 nm. The size of the nanoparticles may be from about 5 nm to about 150 nm (mean diameter), from about 30 to about 100 nm, from about 40 to about 80 nm. The size of the nanoparticles may be from about 25 nm to about 200 nm (mean diameter), from about 30 to about 150 nm, from about 50 to about 100 nm, or from about 75 nm to about 125 nm. The size of the nanoparticles may be from about 125 nm to about 250 nm (mean diameter), from about 150 to about 220 nm, from about 175 to about 250 nm, or from about 175 nm to about 225 nm.

Microparticles, in contrast to nanoparticles, for use in the composition of the invention are 1.0 μm up to about 100 μm, and in one embodiment up to about 3.0 μm.

Compositions, Formulations and Routes of Administration

The compositions of this invention are administered in a therapeutically effective amount to a subject in need of treatment. Administration of the compositions of the invention can be via any of suitable route of administration, particularly parenterally, for example, intravenously, intra-arterially, intraperitoneally, intrathecally, intraventricularly, intraurethrally, intrasternally, intracranially, intratumorally, intramuscularly, or subcutaneously. Such administration may be as a single bolus injection, multiple injections, or as a short- or long-duration infusion. Implantable devices (e.g., implantable infusion pumps) may also be employed for the periodic parenteral delivery over time of equivalent or varying dosages of the particular formulation. For such parenteral administration, the compositions may be formulated as a sterile solution in water or another suitable solvent or mixture of solvents. The solution may contain other substances such as salts, sugars (particularly glucose or mannitol), to make the solution isotonic with blood, buffering agents such as acetic, citric, and/or phosphoric acids and their sodium salts, and preservatives.

The compositions of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compositions may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it may include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, methods of preparation are vacuum drying and the freeze drying techniques, which yield a powder of the active ingredient plus any additional desired ingredient present in the previously sterile-filtered solutions.

For topical administration, the present compositions may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compositions can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

In addition, in one embodiment, the invention provides various dosage formulations for inhalation delivery. For example, formulations may be designed for aerosol use in devices such as metered-dose inhalers, dry powder inhalers and nebulizers.

Examples of useful dermatological compositions which can be used to deliver the compositions of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compositions of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the composition(s) of the invention in a liquid composition, such as a lotion, will be from about 0.1-25 wt-%, or from about 0.5-10 wt-%. The concentration in a semi-solid or solid composition such as a gel or a powder will be about 0.1-5 wt-%, or about 0.5-2.5 wt-%.

The active ingredient may be administered to achieve peak plasma concentrations of the active compound of from about 0.5 to about 75 μM, about 1 to 50 μM, or about 2 to about 30 μM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician. In general, however, a suitable dose will be in the range of from about 0.5 to about 100 mg/kg, e.g., from about 10 to about 75 mg/kg of body weight per day, such as 3 to about 50 mg per kilogram body weight of the recipient per day, in the range of 6 to 90 mg/kg/day, or in the range of 15 to 60 mg/kg/day.

The composition is conveniently administered in unit dosage form; for example, containing 5 to 1000 mg, conveniently 10 to 750 mg, most conveniently, 50 to 500 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye. The dose, and perhaps the dose frequency, will also vary according to the age, body weight, condition, and response of the individual patient. In general, the total daily dose range for a compound or compounds of formula (I) or (II), for the conditions described herein, may be from about 50 mg to about 5000 mg, in single or divided doses. A daily dose range may be about 100 mg to about 4000 mg, or about 1000-3000 mg, in single or divided doses, e.g., 750 mg every 6 hr of orally administered composition. This can achieve plasma levels of about 500-750 uM, which can be effective to kill cancer cells. In managing the patient, the therapy should be initiated at a lower dose and increased depending on the patient's global response.

As described above, compositions are useful in the treatment or prevention of a disease or disorder in, for example, humans or other mammals (e.g., bovine, canine, equine, feline, ovine, and porcine animals), and perhaps other animals as well. Depending on the particular compound, the composition will, for example, be useful for treating cancer.

The invention will be described by the following non-limiting example.

Example

Synthesis:

Scheme 1. Synthesis of benzamide derivatives

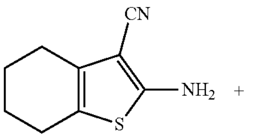

1

-continued

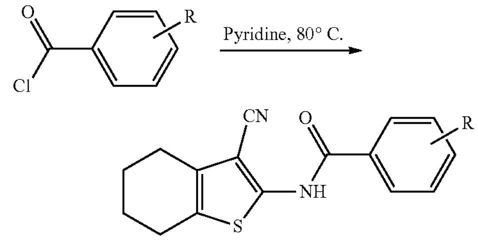

2-5

| | 2 | 3 | 4 | 5 |
|---|---|---|---|---|
| R | 2-I | 2-Br | 3-Br | 4-Br |

General Procedure for Synthesis of 2-5

Compound 1 was synthesized as previously reported in Gewald et al. (1966). Compound 1 (0.003 mol) and the corresponding acid chloride (0.003 mol) were heated at 80° C. in pyridine (10 mL) for 16-18 h. The reaction mixture was cooled and poured into 200 mL of 1M HCl, then the aqueous mixture was extracted with chloroform (75 mL×3). The combined organic layers were concentrated under reduced pressure and the crude product was purified by flash column chromatography using ethylacetate/hexanes as eluent solvents to give 2-5 as yellow to white solids.

Scheme 2. Synthesis of benzylamine derivatives

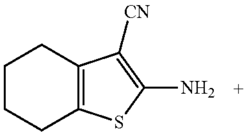

1

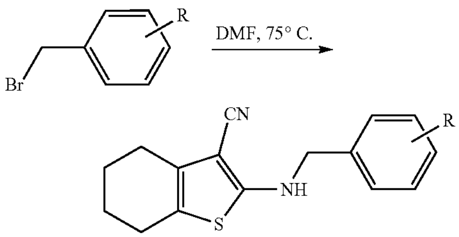

6-10

| | 6 | 7 | 8 | 9 | 10 |
|---|---|---|---|---|---|
| R | 2-F | 2-I | 2-Br | 3-Br | 4-Br |

General Procedure for Synthesis of 6-10

Compound 1 (0.003 mol) and the corresponding benzyl bromide (0.003 mol) were heated at 75° C. in DMF (10 mL) for 24 h. The reaction mixture was cooled and poured into 200 mL of brine solution, then the aqueous mixture was extracted with chloroform (75 mL×3). The combined organic layers were concentrated under reduced pressure and the crude product was purified by flash column chromatography using ethylacetate/hexanes as eluent solvents to give 6-10 as yellow solids.

Scheme 3. Synthesis of urea derivatives

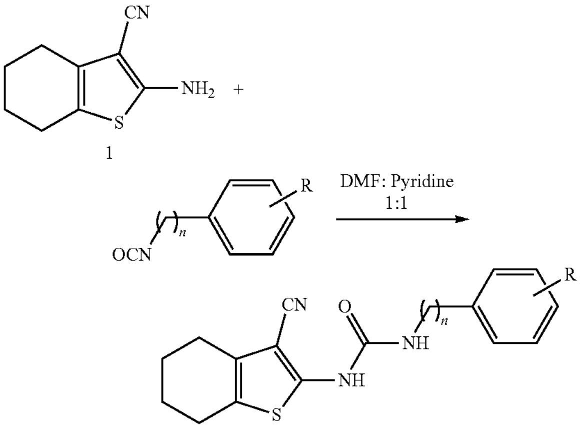

1

11-15

| | 11 | 12 | 13 | 14 | 15 |
|---|---|---|---|---|---|
| R | 4-H | 4-$CH_3$ | 4-$C_4H_9$ | 4-$OCH_3$ | 2-Br |
| n | 1 | 0 | 0 | 0 | 0 |

General Procedure for Synthesis of 11-15

Compound 1 (0.003 mol) and the corresponding isocyanate (0.003 mol) were stirred at room temperature in a mixture of DMF:pyridine (10 mL 1:1) for 24-36 h. The reaction mixture was cooled and poured into 200 mL of 1M HCl, then the aqueous mixture was extracted with chloroform (75 mL×3). The combined organic layers were concentrated under reduced pressure and the crude product was purified by flash column chromatography using ethylacetate/hexanes as eluent solvents to give 11-15 as white solids.

Biological Screening:

In Vitro Antitumor Screening:

The synthesized derivatives were tested for their antitumor activity adopting MTS assay against A549 adenocarcinoma cell line following the reported assay method In Riss et al. Results are shown in Table 2. See FIG. 25.

TABLE 2

$IC_{50}$ values of the tested compounds 2-15

| Compound | $IC_{50}$ |
|---|---|
| 2 | >75 uM |
| 3 | 61.77 uM |
| 4 | 7.6 uM |
| 5 | 53.22 uM |
| 6 | >75 uM |
| 7 | 30.7 uM |
| 8 | 84.08 uM |
| 9 | >75 uM |
| 10 | 2.7 uM |
| 11 | 1.6 uM |
| 12 | ND |
| 13 | ND |
| 14 | >75 uM |
| 15 | >75 uM |

ND Not determined

REFERENCES

K. Gewald, E. Schinke, H. Bottcher, 2-Aminothiopheneaus methlenaktiven nitriilen carbonyl verbindungen and schwefet, Chem. Ber. 99 (1966) 94-100.

T. L. Riss, and R. A. Moravec, Comparison of MTT, XTT, and a novel tetrazolium compound for MTS for in vitro proliferation and chemosensitivity assays. Mol. Biol. Cell (Suppl.) (1992) 3, 184a.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A compound of formula (I):

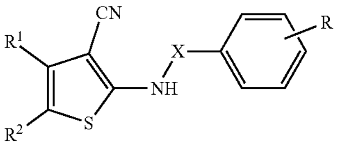

or a pharmaceutically acceptable salt thereof, wherein R is hydrogen, halo, alkyl, alkenyl, alkynyl, alkoxy, haloalkyl, substituted alkyl, carbocycle or heterocycle;

wherein X is CONH(C1-C6) alkyl; and wherein $R^1$ and $R^2$ independently are alkyl, alkenyl, alkynyl, alkoxy, or substituted alkyl or $R^1$ and $R^2$ together form a C6 or C7 ring.

2. The compound of claim 1, or a pharmaceutically acceptable salt thereof, wherein R is halo, (C1-C6)alkyl, substituted (C1-C6)alkyl, or C5-C7 carbocycle.

3. The compound of claim 1, or a pharmaceutically acceptable salt thereof, wherein $R^1$ and $R^2$ together form a C6 ring.

4. The compound of claim 1 which is:

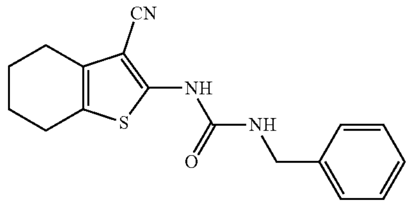 [SMILES: N#Cc1c(NC(=O)NCc2ccccc2)sc2c1CCCC2]

or a pharmaceutically acceptable salt thereof.

5. A composition having nanoparticles comprising the compound of claim 1 or a pharmaceutically acceptable salt thereof.

6. The composition of claim 5, wherein the nanoparticles comprise a polymer comprising lactic acid, glycolic acid, caproic acid, a polyanhydride, or a combination thereof.

* * * * *